US011890327B2

(12) United States Patent
Pestel et al.

(10) Patent No.: US 11,890,327 B2
(45) Date of Patent: Feb. 6, 2024

(54) TRUNCATED VON WILLEBRAND FACTOR POLYPEPTIDES FOR EXTRAVASCULAR ADMINISTRATION IN THE TREATMENT OR PROPHYLAXIS OF A BLOOD COAGULATION DISORDER

(71) Applicant: CSL BEHRING LENGNAU AG, Lengnau (CH)

(72) Inventors: Sabine Pestel, Marburg (DE); Elmar Raquet, Frankenberg (DE); Thomas Weimer, Gladenbach (DE)

(73) Assignee: CSL Behring Lengnau AG, Lengnau (CH)

( * ) Notice: Subject to any disclaimer, the term of this patent is extended or adjusted under 35 U.S.C. 154(b) by 723 days.

(21) Appl. No.: 16/349,002

(22) PCT Filed: Nov. 10, 2017

(86) PCT No.: PCT/EP2017/078840
§ 371 (c)(1),
(2) Date: May 10, 2019

(87) PCT Pub. No.: WO2018/087271
PCT Pub. Date: May 17, 2018

(65) Prior Publication Data
US 2021/0268071 A1 Sep. 2, 2021

(30) Foreign Application Priority Data
Nov. 11, 2016 (EP) .................................. 16198497

(51) Int. Cl.
A61K 38/37 (2006.01)
A61P 7/04 (2006.01)

(52) U.S. Cl.
CPC ............... A61K 38/37 (2013.01); A61P 7/04 (2018.01)

(58) Field of Classification Search
None
See application file for complete search history.

(56) References Cited

U.S. PATENT DOCUMENTS

| 4,399,216 A | 8/1983 | Axel et al. |
| 4,970,300 A | 11/1990 | Fulton et al. |
| 6,228,613 B1* | 5/2001 | Fischer ..................... A61P 7/04 435/69.1 |
| 6,403,077 B1 | 6/2002 | Strom et al. |
| 7,256,253 B2 | 8/2007 | Bridon et al. |
| 2004/0087778 A1 | 5/2004 | Feige et al. |
| 2014/0018297 A1* | 1/2014 | Bolt ......................... A61P 7/04 514/14.1 |

FOREIGN PATENT DOCUMENTS

| EP | 0117060 | 8/1984 |
| EP | 0772452 | 8/2002 |
| EP | 0710114 | 2/2003 |
| WO | WO 94/15625 | 7/1994 |
| WO | WO 97/03193 | 1/1997 |
| WO | WO 97/11957 | 4/1997 |
| WO | WO 97/40145 | 10/1997 |
| WO | WO 99/55306 | 11/1999 |
| WO | WO 02/060951 | 8/2002 |
| WO | WO 02/103024 | 12/2002 |
| WO | WO 03/076567 | 9/2003 |
| WO | WO 03/087355 | 10/2003 |
| WO | WO 03/093313 | 11/2003 |
| WO | WO 2004/067566 | 8/2004 |
| WO | WO 2004/075923 | 9/2004 |
| WO | WO 2004/101740 | 11/2004 |
| WO | WO 2005/000892 | 1/2005 |
| WO | WO 2005/001025 | 1/2005 |
| WO | WO 2005/063808 | 7/2005 |
| WO | WO 2006/000448 | 1/2006 |
| WO | WO 2006/053299 | 5/2006 |
| WO | WO 2006/071801 | 7/2006 |
| WO | WO 2006/108590 | 10/2006 |
| WO | WO 2007/090584 | 8/2007 |
| WO | WO 2007/126808 | 11/2007 |
| WO | WO 2007/144173 | 12/2007 |
| WO | WO 2008/077616 | 7/2008 |
| WO | WO 2008/151817 | 12/2008 |
| WO | WO-2008151817 A1 * | 12/2008 ............. A61K 38/27 |
| WO | WO 2009/156137 | 12/2009 |
| WO | WO 2011/060242 | 5/2011 |
| WO | WO 2013/083858 | 6/2013 |
| WO | WO 2013/093760 | 6/2013 |
| WO | WO 2013/106787 | 7/2013 |
| WO | WO 2013/120939 | 8/2013 |
| WO | WO 2013/160005 | 10/2013 |
| WO | WO 2014/011819 | 1/2014 |
| WO | WO 2014/173873 A1 | 10/2014 |
| WO | WO 2014/198699 | 12/2014 |
| WO | WO 2015/185758 | 12/2015 |
| WO | WO 2016/000039 | 1/2016 |
| WO | WO 2016/188905 | 12/2016 |

OTHER PUBLICATIONS

Yee et al., "Partial in Vivo FVIII Stabilization by VWF Fragments," Blood, vol. 120, No. 21, 2012, Abstract 15, 2 pages.
Swystun et al., "FVIII Stabilization: VWF D'D3 Will Do," Blood, vol. 124, No. 3, 2014, pp. 313-315.
Yee et al., "A von Willebrand Factor Fragment Containing the D'D3 Domains is Sufficient to Stabilize Coagulation Factor VIII in Mice," Blood, vol. 124, No. 3, 2014, pp. 445-452.

(Continued)

Primary Examiner — Thomas S Heard
(74) Attorney, Agent, or Firm — Finnegan, Henderson, Farabow, Garrett & Dunner, LLP

(57) ABSTRACT

The invention pertains to a recombinant polypeptide comprising a truncated von Willebrand Factor (VWF) for use in the treatment or prophylaxis of a blood coagulation disorder, said treatment or prophylaxis comprising administering the recombinant polypeptide and a Factor VIII protein (FVIII) extravascular to a subject having a blood coagulation disorder, wherein said recombinant polypeptide is capable of binding to said FVIII, and wherein the molar ratio of the recombinant polypeptide to be administered to the FVIII to be administered is higher than 50.

23 Claims, 14 Drawing Sheets
Specification includes a Sequence Listing.

(56) References Cited

OTHER PUBLICATIONS

Graham et al., "A New Technique for the Assay of Infectivity of Huma Adenovirus 5 DNA," Virology, 52, 1973, pp. 456-467.
Graham et al. "Characteristics of a Human Cell Line Transformed by DNA from Human Adenovirus Type 5," J. Gen. Virol., vol. 36, 1977, pp. 59-72.
Mantei et al., "Rabbit ß-globin mRNA Production in Mouse L cells transformed with cloned rabbit ß-globin chromosomal DNA," Nature, vol. 281, 1979, pp. 40-46.
Mather, "Establishment and Characterization of Two Distinct Mouse Testicular Epithelial Cell Lines," Biology of Reproduction, vol. 23, 1980, pp. 243-252.
Oslo, "Remington's Pharmaceutical Sciences," Medical Sciences, 16th Edition, 1980, 1 page.
Urlaub et al., "Isolation of Chinese Hamster Cell Mutants Deficient in Dihydrofolate Reductase Activity," Proc. Natl. Academy Science USA, vol. 77, No. 7, 1980, pp. 4216-4220.
Gething et al., "Cell-Surface Expression of Influenza Haemagglutinin From a Cloned DNA Copy of the RNA Gene," Nature, vol. 293, 1981, pp. 620-625.
Mather et al., "Culture of Testicular Cells in Hormone-Supplemented Serum-Free Medium," Annals New York Academy of Sciences, vol. 383, 1982, pp. 44-68.
Lee et al., "An Effect of Predilution on Potency Assays of Factor VII Concentrates," Thrombosis Research 30, 1983, pp. 511-519.
Collins et al., "Molecular Cloning of the Human Gene for von Willebrand Factor and Identification of the Transcription Initiation Site," Proc. Natl. Acad. Sci. USA, vol. 84, 1987, pp. 4393-4397.
Mansour et al., "Disruption of the Proto-oncogene int-2 in Mouse Embryo-derived Stem Cells: A General Strategy for Targeting Mutations to Non-Selectable Genes," Nature, vol. 336, 1988, pp. 348-352.
Kaufman et al., "Effect of von Willebrand Factor Coexpression on the Synthesis and Secretion of Factor VIII in Chinese Hamster Ovary Cells," Molecular and Cellular Biology, vol. 9, 1989, pp. 1233-1242.
Keown et al., "Methods for Introducing DNA into Mammalian Cells," Introducing DNA into Mammalian Cells, Methods in Enzymology, vol. 185, 1990, pp. 527-537.
Hawley-Nelson et al., "LipofectAMINE™ Reagent: A New, Higher Efficiency Polycationic Liposome Transfection Reagent," Focus, vol. 15, No. 3, 1993, pp. 73-79.
Fischer et al., "Structural Analysis of Recombinant von Willebrand Factor: Identification of Hetero- and Homo-Dimers," FEBS Letters, 351, 1994, pp. 345-348.
Bi et al., "Targeted Disruption of the Mouse Factor VIII Gene Produces a Model of Haemophilia A," Nature Genetics, vol. 10, 1995, pp. 119-121.
Bi et al., "Further Characterization of Factor VIII-Deficient Mice Created by Gene Targeting: RNA and Protein Studies," Blood, vol. 88, No. 9, 1996, pp. 3446-3450.
Dumont et al., "Monomeric Fc Fusions," Biodrugs, vol. 20, No. 3, 2006, pp. 151-160.
Sadler et al., "Chapter 60 von Willebrand Disease: Diagnosis, Classification, and Treatment," HemostThromb, 2006, pp. 905-921.
Schellenberger et al., "A Recombinant Polypeptide Extends the In Vivo Half-Life of Peptides and Proteins in a Tunable Manner," Nature Biotechnology, vol. 27, No. 12, 2009, pp. 1186-1190.
Zhou et al., "Sequence and Structure Relationships Within von Willebrand Factor," Blood, vol. 120, No. 2, 2012, pp. 449-458.
Haberichter et al., "Chapter 13, Structure and Function of von Willebrand Factor," Hemostasis and Thrombosis, 2013, pp. 197-207.
Lenting et al., "von Willebrand Factor Biosynthesis, Secretion, and Clearance: Connecting the Far Ends," Blood, vol. 125, No. 13, 2015, pp. 2019-2028.
International Search Report and the Written Opinion of the International Searching Authority, issued in International Application No. PCT/EP2017/078840, dated Jan. 26, 2018, 17 pages.
European Search Report and Written Opinion, issued in EP Patent Application No. 16198497.6, dated May 11, 2017, 12 pages.

* cited by examiner

TRUNCATED VON WILLEBRAND FACTOR POLYPEPTIDES FOR EXTRAVASCULAR ADMINISTRATION IN THE TREATMENT OR PROPHYLAXIS OF A BLOOD COAGULATION DISORDER

This application is the United States national stage entry under 35 U.S.C. § 371 of International Application No. PCT/EP2017/078840, filed on Nov. 10, 2017 and published as WO 2018/087271 A1, which claims priority to European Patent Application No. 16198497.6, filed on Nov. 11, 2016. The contents of these applications are each incorporated herein by reference in their entirety.

FIELD OF THE INVENTION

The present invention relates to products and methods for improving treatment of blood coagulation disorders.

BACKGROUND OF THE INVENTION

There are various bleeding disorders caused by deficiencies of blood coagulation factors. The most common disorders are hemophilia A and B, resulting from deficiencies of blood coagulation Factor VIII (FVIII) and IX, respectively. Another known bleeding disorder is von Willebrand's disease (VWD).

In plasma FVIII exists mostly as a noncovalent complex with von Willebrand Factor (VWF), and its coagulant function is to accelerate Factor IXa dependent conversion of Factor X to Xa.

Classic hemophilia or hemophilia A is an inherited bleeding disorder. It results from a chromosome X-linked deficiency of blood coagulation FVIII, and affects almost exclusively males with an incidence of between one and two individuals per 10,000. The X-chromosome defect is transmitted by female carriers who are not themselves hemophiliacs. The clinical manifestation of hemophilia A is an increased bleeding tendency.

In severe hemophilia A patients undergoing prophylactic treatment FVIII has to be administered intravenously (i.v.) about 3 times per week due to the short plasma half-life of FVIII of about 12 to 14 hours. Each i.v. administration is cumbersome, associated with pain and entails the risk of an infection especially as this is mostly done at home by the patients themselves or by the parents of children having been diagnosed for hemophilia A.

It would thus be highly desirable to increase the half-life of FVIII so that pharmaceutical compositions containing such FVIII would have to be administered less frequently.

Several attempts have been made to prolong the half-life of non-activated FVIII either by reducing its interaction with cellular receptors (WO 2003/093313 A2, WO 2002/060951 A2), by covalently attaching polymers to FVIII (WO 1994/15625 A1, WO 1997/11957 A1 and U.S. Pat. No. 4,970,300), by encapsulation of FVIII (WO 1999/55306 A1), by introduction of novel metal binding sites (WO 1997/03193 A1), by covalently attaching the A2 domain to the A3 domain either by peptidic (WO 1997/40145 A1 and WO 2003/087355 A1) or disulfide linkage (WO 2002/103024 A2) or by covalently attaching the A1 domain to the A2 domain (WO 2006/108590 A1).

Another approach to enhance the functional half-life of FVIII or VWF is by PEGylation of FVIII (WO 2007/126808 A1, WO 2006/053299 A2, WO 2004/075923 A2) or by PEGylation of VWF (WO 2006/071801 A2). The increased half-life of PEGylated VWF would indirectly also enhance the half-life of FVIII present in plasma. Also fusion proteins of FVIII have been described (WO 2004/101740 A2, WO2008/077616 A1 and WO 2009/156137 A1).

VWF, which is missing, functionally defect or only available in reduced quantity in different forms of von Willebrand disease (VWD), is a multimeric adhesive glycoprotein present in the plasma of mammals, which has multiple physiological functions. During primary hemostasis VWF acts as a mediator between specific receptors on the platelet surface and components of the extracellular matrix such as collagen. Moreover, VWF serves as a carrier and stabilizing protein for procoagulant FVIII. VWF is synthesized in endothelial cells and megakaryocytes as a 2813 amino acid precursor molecule. The amino acid sequence and the cDNA sequence of wild-type VWF are disclosed in Collins et al. 1987, Proc. Natl. Acad. Sci. USA 84:4393-4397. The precursor polypeptide, pre-pro-VWF, consists of an N-terminal 22-residue signal peptide, followed by a 741-residue pro-peptide and the 2050-residue polypeptide found in mature plasma VWF (Fischer et al., FEBS Lett. 351: 345-348, 1994). After cleavage of the signal peptide in the endoplasmatic reticulum a C-terminal disulfide bridge is formed between two monomers of VWF. During further transport through the secretory pathway 12 N-linked and 10 O-linked carbohydrate side chains are added. More important, VWF dimers are multimerized via N-terminal disulfide bridges and the propeptide of 741 amino acids length is cleaved off by the enzyme PACE/furin in the late Golgi apparatus.

Once secreted into plasma the protease ADAMTS13 can cleave high-molecular weight VWF multimers within the A1 domain of VWF. Plasma VWF therefore consists of a whole range of multimers ranging from single dimers of 500 kDa to multimers consisting of up to more than 20 dimers of a molecular weight of over 10,000 kDa. The VWF-HMWM hereby having the strongest hemostatic activity, which can be measured in ristocetin cofactor activity (VWF:RCo). The higher the ratio of VWF:RCoNWF antigen, the higher the relative amount of high molecular weight multimers.

In plasma FVIII binds with high affinity to VWF, which protects it from premature elimination and thus, plays in addition to its role in primary hemostasis a crucial role to stabilize FVIII, regulate plasma levels of FVIII and as a consequence is also a central factor to control secondary hemostasis. The half-life of non-activated FVIII bound to VWF is about 12 to 14 hours in plasma. In von Willebrand disease type 3, where no or almost no VWF is present, the half-life of FVIII is only about 2 to 6 hours, leading to symptoms of mild to moderate hemophilia A in such patients due to decreased concentrations of FVIII. The stabilizing effect of VWF on FVIII has also been used to aid recombinant expression of FVIII in CHO cells (Kaufman et al. 1989, Mol Cell Biol 9:1233-1242). Von Willebrand disease type 2N is characterized by low FVIII levels due to mutations in VWF which affect the binding of FVIII to VWF. FVIII levels in VWD type 2N patients are in a range between about 3 IU/dL and 30 IU/dL, typically below 20 IU/dL, depending on the specific mutation in VWF (Sadler J. E. and Blinder M., Von Willebrand Disease: Diagnosis, Classification, and Treatment; in: Hemostasis and Thrombosis, eds. Colman, Marder, Clowes, George, Aird, and Goldhaber, Lippincott Williams & Wilkins 2006, pp 905-921).

VWF-derived polypeptides, in particular VWF fragments, have been described to stabilize FVIII in vitro and in vivo. WO 2013/106787 A1 is directed at chimeric proteins comprising a FVIII protein and certain VWF fragments. Those chimeric hetero-dimers of FVIII and VWF-fragment do have a fixed molar ratio of VWF to FVIII of 1:1.

WO 2014/198699 A2 and WO 2013/083858 A2 describe VWF fragments and their use in the treatment of hemophilia. It was found that bioavailability of FVIIIs may be significantly improved upon extravascular co-administration with similar molar amounts of VWF fragments. High molar excess of VWF over FVIII was said to be not desirable, and in experiments with VWF fragments co-administered s.c. with FVIII it was found that the VWF dose was not critical for FVIII bioavailability. Thus molar ratios of VWF fragments over FVIII as well as VWF dose were considered to be not critical for FVIII bioavailability.

WO 2011/060242 A2 discloses fusion polypeptides comprising certain VWF fragments and an antibody Fc region proposing specific molar ratios of VWF fragment over FVIII of up to 10:1. In addition, no in vivo data are presented with regard to said Fc-fusion constructs.

Yee et al. (2014) Blood 124(3):445-452 found that a VWF fragment containing the D'D3 domains fused to the Fc portion of immunoglobulin G1 is sufficient to stabilize endogenous Factor VIII in VWF-deficient mice. However, although a VWF D'D3-Fc fusion protein exhibited markedly prolonged survival when transfused into FVIII-deficient mice, the VWF D'D3-Fc fusion protein did not prolong the survival of co-transfused FVIII.

Until today the standard treatment of hemophilia A involves frequent intravenous infusions of FVIII, either as concentrates derived from the plasmas of human donors or as pharmaceutical preparations based on recombinant FVIII. While these replacement therapies are generally effective, e.g. in severe hemophilia A patients undergoing prophylactic treatment, as mentioned above Factor VIII has to be administered intravenously (i.v.) about 3 times per week due to the short plasma half-life of Factor VIII of about 12 hours. Already if levels of above 1% of the FVIII activity in healthy non-hemophiliacs is reached, e.g. by a raise of FVIII levels above 0.01 U/mL, severe hemophilia A is turned into moderate hemophilia A. In prophylactic therapy dosing regimens are designed such that the trough levels of FVIII activity do not fall below levels of 2-3% of the FVIII activity in healthy non-hemophiliacs. Each i.v. administration is cumbersome, associated with pain and entails the risk of an infection especially as this is mostly done in home treatment by the patients themselves or by the parents of children being diagnosed for hemophilia A. In addition the frequent i.v. injections inevitably result in scar formation, interfering with future infusions. As prophylactic treatment in severe hemophilia is started early in life, with children often being less than 2 years old, it is even more difficult to inject FVIII 3 times per week into the veins of such small patients. For a limited period, implantation of port systems may offer an alternative. Despite the fact that repeated infections may occur and ports can cause inconvenience during physical exercise, they are nevertheless typically considered to be favorable as compared to intravenous injections.

Thus there is still a great medical need to obviate the need to infuse FVIII intravenously. As FVIII is a very large and labile molecule it exhibits a very low bioavailability due to insufficient absorption and severe degradation, if given subcutaneously, intramuscularly or intradermally, i.e. extravascularly.

EP 0710114 A1 discloses that FVIII formulations of a B-domain deleted FVIII in a concentration above 1000 IU/mL are suitable for subcutaneous administration, leading to a bioavailability of 5-10% after s.c. administration in monkeys measuring the area under the activity (FVIII:C)-time curve.

EP 0772452 discloses that FVIII formulations of a B-domain deleted FVIII in a concentration of at least 500 IU/mL together with an organic additive when administered subcutaneously can lead for more than 6 h to a FVIII plasma level of at least 1.5% of normal FVIII levels. Using hydrolyzed gelatin or soybean oil emulsion as the organic additive and a B-domain deleted FVIII in a concentration of 1100 IU/mL and a dose of 10000 IU/kg, more than 50% bioavailability as measured as the area under the activity (FVIII:C)-time curve was seen in cynomolgus monkeys. This is however not an appropriate clinical scenario for treatment of a patient having a blood coagulation disorder.

WO 1997/11957 A1 discloses a bioavailability of 5.3% when a B-domain deleted FVIII (specific activity 15000 UI/mg; dose 2500 IU/kg) was administered subcutaneously, whereas an mPEGylated conjugate of FVIII achieved bioavailabilities of 22% or 19% in cynomolgus monkeys.

According to WO 2015/185758 A2 a composition is presented comprising a non-covalent complex of Factor VIII and one or more von Willebrand Factor peptides, wherein the von Willebrand Factor peptides comprise at least the amino acids 764 to 1035 and 1691 to 1905. The molecular ratio of FVIII:VWF is between 1:1 to 1:20. In WO 2015/185758 A2 haemophilia A dogs were subjected to s.c. and subsequent i.v. injection of recombinant B-domain-deleted FVIII alone or in combination with five-fold molar excess of a VWF fragment yielded by digestion of pdVWF with *S. aureus* V-8 protease. Samples were analyzed for whole blood clotting time (WBCT) and activity in chromogenic FVIII activity assay. The subcutaneous administration of a VWF Fragment in complex with FVIII resulted in 1.4-fold increase in time required to exceed a clotting time for a normal dog comparing with s.c. administration of FVIII alone. The administration of VWF Fragment with FVIII resulted also in increased FVIII activity in dog plasma over time and in nearly doubled area under the curve (AUC) values for both, s.c. and i.v. application compared to administration of FVIII alone.

In WO 2008/151817 A1 it was shown that VWF can be taken up into the blood stream when administered extravascularly without any stabilizing covalent modifications, which can entail an increased risk of immune responses, and that VWF can be used to enhance the uptake of FVIII when co-administered with FVIII non-intravenously. The VWF was applied without any half-life extending modification. The ratio of VWF antigen over FVIII activity was larger than 2:1. Only multimer and monomer products comprising a full length VWF have been considered. By applying full length VWF, however, high ratios of VWF over FVIII may result in an elevated thrombogenic risk. In addition, when using full length VWF the protein amounts required for increasing the ratio would not be acceptable for administration. Further, multimeric and monomeric.

There is a medical need for alternatives to the intravenous administration of FVIII to patients. In addition, there is an ongoing need for methods providing Factor VIII absorption when administered extravascularly as well as for compounds or compositions suitable for such methods.

SUMMARY OF THE INVENTION

A first object of present invention was to provide an improved Factor VIII (FVIII) protein based treatment or prophylaxis of a blood coagulation disorder.

According to a second object, said treatment should allow for alternative routes of administration of FVIII to a subject in need thereof. In particular, subcutaneous administration of FVIII should be enabled.

According to a third object, said treatment should provide at least with regard to the administered FVIII pharmacokinetic parameters sufficient to treat a subject having a blood coagulation disorder.

According to a fourth object, said treatment should provide in particular for a half-life of FVIII which is sufficiently high to allow for a tolerable or improved administration frequency.

It has been surprisingly found by the inventors that a Factor VIII (FVIII) protein can be successfully administered via an extravascular route for treatment or prophylaxis of a blood coagulation disorder, provided that the FVIII is co-administered with a recombinant polypeptide comprising a truncated von Willebrand Factor (VWF). Said recombinant polypeptide is capable of binding to said co-administered FVIII. The molar ratio of the recombinant polypeptide to be administered to the FVIII to be administered is preferably higher than 50. The recombinant polypeptide comprising a truncated VWF preferably comprises a half-life extending moiety (HLEM). Without wishing to be bound to any theory, it is believed that it is important to achieve a high excess of the administered recombinant polypeptide comprising a truncated VWF to minimize the binding of the co-administered FVIII to endogenous VWF which has a larger molecular structure probably leading to an increased catabolism as compared to the truncated VWF. By use of the herewith presented co-administration of FVIII and said recombinant polypeptide, it is demonstrated for the first time that extravascular route for application of FVIII is not only possible, but even achieved clinically relevant amounts of FVIII into circulation.

The invention further demonstrates that extravascular administration of the recombinant polypeptide provides for or increases bioavailability of a co-administered FVIII. In addition, subcutaneous administration of the recombinant polypeptide together with FVIII allows for extravascular administration of a FVIII associated with relevant absorption of FVIII into the bloodstream resulting in FVIII activity levels not only significantly above the detection limit, but furthermore suitable for therapeutic application. The recombinant polypeptide when co-administered with FVIII not only has a sufficiently long half-life, increases maintenance of FVIII in plasma once it reached this compartment, but also provides bioavailability of FVIII suitable for therapeutic application.

In addition, the invention further demonstrates that extravascular administration of the recombinant polypeptide may allow for a treatment option comprising an FVIII administration via a different route of administration than used for the recombinant polypeptide. In particular, benefits arising from a combination of an intravenously administered FVIII and a subcutaneously administered recombinant polypeptide are demonstrated.

The present invention therefore relates particularly to the following embodiments [1] to [73]:

[1] A recombinant polypeptide comprising a truncated von Willebrand Factor (VWF) for use in the treatment or prophylaxis of a blood coagulation disorder, said treatment or prophylaxis comprising administering the recombinant polypeptide and a Factor VIII protein (FVIII) extravascular to a subject having a blood coagulation disorder, wherein said recombinant polypeptide is capable of binding to said FVIII, and wherein the molar ratio of the recombinant polypeptide to be administered to the FVIII to be administered is higher than 50.

[2] A recombinant polypeptide comprising a truncated von Willebrand Factor (VWF) for use in the treatment or prophylaxis of a blood coagulation disorder, said treatment or prophylaxis comprising administering the recombinant polypeptide extravascular and a Factor VIII protein (FVIII) to a subject having a blood coagulation disorder, wherein said recombinant polypeptide is capable of binding to said FVIII, and wherein the molar ratio of the recombinant polypeptide to be administered to the FVIII to be administered is higher than 50.

[3] The recombinant polypeptide for use according to embodiment [1] or [2], wherein said polypeptide comprises a half-life extending moiety (HLEM).

[4] The recombinant polypeptide for use according to any one of the preceding embodiments, wherein the subject is a human subject.

[5] The recombinant polypeptide for use according to any one of the preceding embodiments, wherein the truncated VWF is a human truncated VWF.

[6] The recombinant polypeptide for use according to any one of the preceding embodiments, wherein said polypeptide is administered either subcutaneously, intradermally or intramuscularly.

[7] The recombinant polypeptide for use according to any one of the preceding embodiments, wherein the FVIII is administered either subcutaneously, intradermally or intramuscularly. Preferably, both FVIII and said polypeptide are administered subcutaneously.

[8] The recombinant polypeptide for use according to embodiments [2] to [6], wherein the FVIII is administered via a different route of administration than the recombinant polypeptide, preferably FVIII is administered intravenously; more preferred the recombinant polypeptide is administered subcutaneously and the FVIII is administered intravenously.

[9] The recombinant polypeptide for use according to any one of the preceding embodiments, wherein the truncated VWF comprises an amino acid sequence having a sequence identity of at least 90% to amino acids 776 to 805 of SEQ ID NO:4, preferably comprises an amino acid sequence having a sequence identity of at least 90% to amino acids 764 to 1242 of SEQ ID NO:4.

[10] The recombinant polypeptide for use according to any one of the preceding embodiments, wherein the truncated VWF lacks amino acids 1243 to 2813 of SEQ ID NO:4.

[11] The recombinant polypeptide for use according to any one of the preceding embodiments, wherein the truncated VWF consists either of (a) amino acids 764 to 1242 of SEQ ID NO:4, of (b) an amino acid sequence having a sequence identity of at least 90% to amino acids 764 to 1242 of SEQ ID NO:4, or of (c) a fragment of (a) or (b).

[12] The recombinant polypeptide for use according to any one of the embodiments [3] to [11], wherein the HLEM is a heterologous amino acid sequence fused to the truncated VWF.

[13] The recombinant polypeptide for use according to embodiment [12], wherein said heterologous amino acid sequence comprises or consists of a polypeptide selected from the group consisting of transferrin and fragments thereof, the C-terminal peptide of human chorionic gonadotropin, an XTEN sequence, homo-amino acid repeats (HAP), proline-alanine-serine repeats (PAS), albumin, afamin, alpha-fetoprotein, Vitamin D binding protein, polypeptides capable of binding under physiological conditions to albumin or immunoglobulin constant regions, polypeptides capable of binding to the neonatal Fc receptor (FcRn), particularly immunoglobulin constant regions and portions thereof, preferably the Fc portion of immunoglobulin, and combinations thereof. The immunoglobulin constant region or portions thereof is preferably an Fc fragment of immunoglobulin G1, an Fc fragment of immunoglobulin G2 or an Fc fragment of immunoglobulin A.

[14] The recombinant polypeptide for use according to any one of embodiments [3] to [11], wherein the HLEM is conjugated to the recombinant polypeptide.

[15] The recombinant polypeptide for use according to embodiment [14], wherein said HLEM is selected from the group consisting of hydroxyethyl starch (HES), polyethylene glycol (PEG), polysialic acids (PSAs), elastin-like polypeptides, heparosan polymers, hyaluronic acid and albumin binding ligands, e.g. fatty acid chains, and combinations thereof.

[16] The recombinant polypeptide for use according to any one of embodiments [3] to [13], wherein the recombinant polypeptide does not comprise any HLEM conjugated to the recombinant polypeptide.

[17] The recombinant polypeptide for use according to any one of the preceding embodiments, wherein said polypeptide is a glycoprotein comprising N-glycans, and wherein preferably at least 75%, preferably at least 85% of said N-glycans comprise, on average, at least one sialic acid moiety.

[18] The recombinant polypeptide for use according to any one of the preceding embodiments, wherein said recombinant polypeptide is present as a dimer or at least has a high proportion of dimers.

[19] The recombinant polypeptide for use according to embodiment [18], wherein said recombinant polypeptide is a homodimer preferably comprising two polypeptides as defined in one of the herein disclosed embodiments, and the two monomers forming the dimer are covalently linked to each other via at least one or more disulfide bridges formed by cysteine residues within the truncated VWF.

[20] The recombinant polypeptide for use according to embodiment [19], wherein the cysteine residues forming the one or more disulfide bridges is/are selected from the group consisting of Cys-1099, Cys-1142, Cys-1222, Cys-1225, Cys-1227 and combinations thereof, preferably Cys-1099 and Cys-1142, wherein the amino acid numbering refers to SEQ ID NO:4.

[21] The recombinant polypeptide for use according to any one of embodiments [18] to [20], wherein the affinity of said dimer to FVIII is greater than the affinity of a monomeric polypeptide to FVIII, said monomeric polypeptide having the same amino acid sequence as a monomeric subunit of the dimeric polypeptide.

[22] The recombinant polypeptide for use according to any one of embodiments [18] to [21], wherein the ratio dimer:monomer of the polypeptide of the invention is at least 1.5, preferably at least 2, more preferably at least 2.5 or at least 3. Preferably, the recombinant polypeptide of the invention does not comprise monomer and/or multimer forms of the polypeptide or at least is essentially free of monomer and/or multimer forms of the polypeptide. Most preferably all polypeptides of the invention are present as dimers.

[23] The recombinant polypeptide for use according to any one of embodiments [18] to [22], wherein the dimeric polypeptide has a FVIII binding affinity characterized by a dissociation constant $K_D$ of less than 1 nM, preferably less than 500 pM, less than 200 pM, less than 100 pM, less than 90 pM or less than 80 pM.

[24] The recombinant polypeptide for use according to embodiment [23], wherein the $K_D$ ranges from 0.1 pM to 500 pM, from 0.5 pM to 200 pM, from 0.75 pM to 100 pM or most preferred from 1 pM to 80 pM.

[25] The recombinant polypeptide for use according to any one of embodiments [18] to [24], wherein the polypeptide has a FVIII binding affinity characterized by a dissociation constant $K_D$ and said dissociation constant $K_D$ of the dimeric polypeptide is reduced compared to the dissociation constant $K_D$ of a monomeric polypeptide, preferably by a factor of at least 10, by a factor of at least 100, by a factor of at least 500 or by a factor of at least 1000.

[26] The recombinant polypeptide for use according to any one of the preceding embodiments, wherein said polypeptide comprises at least one amino acid substitution as compared to the amino acid sequence of the wild-type VWF, wherein the binding affinity of such a modified polypeptide to FVIII is preferably being further increased by introduction of said at least one substitution compared to the binding affinity of a reference polypeptide which has the same amino acid sequence except for said modifications.

[27] The recombinant polypeptide for use according to embodiment [26], wherein said substitutions within the truncated VWF have the capacity to further increase the half-life of co-administered FVIII following administration. Thereby, the treatment may also provide in particular an in vivo half-life of FVIII which is further increased to allow for a tolerable or improved administration frequency.

[28] The recombinant polypeptide for use according to embodiments [26] or [27], wherein the substitutions are selected from the group of combinations consisting of S764G/S766Y, S764P/S766I, S764P/S766M, S764V/S766Y, S764E/S766Y, S764Y/S766Y, S764 L/S766Y, S764P/S766W, S766W/S806A, S766Y/P769K, S766Y/P769N, S766Y/P769R, S764P/S766 L, and S764E/S766Y/V1083A, referring to the sequence of SEQ ID NO:4 with regard to the amino acid numbering.

[29] The recombinant polypeptide for use according to embodiment [28], wherein said substitution is the either the combination S764E/S766Y or S764E/S766Y/V1083A.

[30] The recombinant polypeptide for use according to any one of the preceding embodiments, wherein the mean residence time (MRT) of the administered FVIII is increased by the co-administration of the recombinant polypeptide, preferably by a factor of at least 1.5, at least 2, at least 3, at least 4 or at least 5, as compared to a reference treatment, wherein said reference treatment is identical to said treatment, except that the recombinant polypeptide to be administered does not comprise a HLEM and/or except that the molar ratio of the recombinant polypeptide to be administered to the FVIII to be administered is below a molar ratio according to the invention and/or except that no recombinant polypeptide has been administered.

[31] The recombinant polypeptide for use according to any one of the preceding embodiments, wherein the MRT of the administered FVIII is at least 10 h, preferably at least 15 h, at least 20 h or at least 25 h.

[32] The recombinant polypeptide for use according to any one of the preceding embodiments, wherein the MRT of the administered recombinant polypeptide is increased, preferably by a factor of at least 1.5, at least 2 or at least 3, as compared to a reference treatment, wherein said reference treatment is identical to said treatment, except that the recombinant polypeptide to be administered does not comprise a HLEM and/or except that the molar ratio of the recombinant polypeptide to be administered to the FVIII to be administered is below a molar ratio according to the invention, in particular below 50.

[33] The recombinant polypeptide for use according to any one of the preceding embodiments, wherein the terminal half-life of the administered FVIII is increased by the co-administration of the recombinant polypeptide, preferably by a factor of at least 1.2, at least 1.5, at least 2, at least 2.5, or at least 3, as compared to a reference treatment, wherein said reference treatment is identical to said treatment, except that the recombinant polypeptide to be administered does not comprise a HLEM and/or except that the molar ratio of the recombinant polypeptide to be administered to the FVIII to be administered is below a molar ratio according to the invention and/or except that no recombinant polypeptide has been administered. Thereby, the treatment may provide in particular an in vivo half-life of FVIII which is sufficiently high to allow for a tolerable or improved administration frequency.

[34] The recombinant polypeptide for use according to any one of the preceding embodiments, wherein the time period for reaching a 1% trough level of the FVIII co-administered with said polypeptide having a HLEM is prolonged compared to a reference treatment, wherein said reference treatment is identical to said treatment, except the FVIII is administered with a recombinant polypeptide without having said HLEM and/or except that no recombinant polypeptide has been administered.

[35] The recombinant polypeptide for use according to any one of the preceding embodiments, wherein the time period either
 (i) for reaching the 1% trough level of the FVIII co-administered with said polypeptide is at least about 30 h, at least about 35 h, at least about 38 h, at least about 40 h, or at least about 50 h; or
 (ii) for reaching the 5% trough level of the FVIII co-administered with said polypeptide is at least about 20 h, at least about 22 h, at least about 29 h, at least about 34 h, or at least about 43 h; or
 (iii) for reaching the 10% trough level of the FVIII co-administered with said polypeptide is at least about 5 h, at least about 6 h, at least about 10 h, at least about 18 h, or at least about 20 h.

[36] The recombinant polypeptide for use according to any one of the preceding embodiments, wherein the plasma half-life of the polypeptide is increased compared to that of endogenous VWF and/or compared to that of VWF of normal human plasma (NHP), wherein the plasma half-life of the polypeptide is preferably at least 100%, at least 200% or preferably at least 400% higher than that of the endogenous VWF and/or compared to that of VWF of normal human plasma (NHP).

[37] The recombinant polypeptide for use according to any one of the preceding embodiments, wherein the blood coagulation disorder is hemophilia A or von-Willebrand disease.

[38] The recombinant polypeptide for use according to embodiment [37], wherein the blood coagulation disorder is hemophilia A and is either mild hemophilia A, typically associated with an endogenous FVIII activity level that is 5% to 40% of the endogenous FVIII activity level in normal human plasma (NHP), or moderate hemophilia A, typically associated with an endogenous FVIII activity level that is 1% to 5% of the endogenous FVIII activity level in NHP, or severe hemophilia A, typically associated with an endogenous FVIII activity level that is below 1% of the endogenous FVIII activity in NHP.

[39] The recombinant polypeptide for use according to any one of the preceding embodiments, wherein the polypeptide is used for (i) on-demand treatment and control of bleeding episodes, (ii) routine prophylaxis, particularly to reduce the frequency of bleeding episodes, or (iii) perioperative management of bleeding.

[40] The recombinant polypeptide for use according to embodiment [39], wherein the polypeptide is used for routine prophylaxis to reduce the frequency of bleeding episodes of a patient with hemophilia A.

[41] The recombinant polypeptide for use according to any one of the preceding embodiments, wherein co-administration of the recombinant polypeptide and the FVIII protein is achieved either
 (i) by administration together in a single composition comprising the recombinant polypeptide and the FVIII protein, or
 (ii) by administration of the recombinant polypeptide (first compound) and the FVIII protein (second compound) each provided in separate compositions, optionally as part of a combined therapy, wherein the first compound is administered before, after or concurrently with the second compound. Any suitable timing interval may be applied for administration of the first compound and the second compound when the first compound is administered before or after the second compound. In particular, for the purpose of routine prophylaxis, administration of the first compound and administration the second compound may be provided according to independent or coordinated dosing schedules.

[42] The recombinant polypeptide for use according to embodiment [41], wherein in case of (i) co-administration of the recombinant polypeptide and the FVIII protein is achieved either
 by providing a combination product comprising the recombinant polypeptide and the FVIII blended in a single composition or
 by providing a set or kit of at least two separate products arranged to be mixed before administration, whereby a first product comprises the recombinant polypeptide and a second product comprises the FVIII.

[43] The recombinant polypeptide for use according to embodiment [41], wherein in case of (ii) the recombinant polypeptide and the FVIII protein, in particular when administered concurrently and/or in particular when administered both extravascularly, are administered in close proximity, preferably, the injection sites are separated not more than 50 mm, not more than 40 mm, not more than 30 mm, in particular not more than 20 mm.

[44] The recombinant polypeptide for use according to embodiment [41] or [43], wherein in case of (ii) the recombinant polypeptide and the FVIII protein may be co-administered within 1 month, within three weeks, within two weeks, within one week, within one day, within about one hour, within 30 min, within 15 min or within 5 min.

[45] The recombinant polypeptide for use according to embodiment [41], [43] or [44], wherein in case of (ii) the recombinant polypeptide and the FVIII protein may be co-administered within a timing interval of no more than 1 month, no more than three weeks, no more than two weeks, no more than one week, no more than one day, no more than about one hour, preferably within 30 min, more preferably within 15 min and most preferably within 5 min.

[46] The recombinant polypeptide for use according to any one of the preceding embodiments, wherein the recombinant polypeptide does not comprise a FVIII protein and/or does not comprise a polypeptide having a FVIII activity.

[47] The recombinant polypeptide for use according to any one of the preceding embodiments, wherein the FVIII is a plasma derived FVIII protein or a recombinant FVIII protein, preferably a human FVIII protein.

[48] The recombinant polypeptide for use according to any one of the preceding embodiments, wherein the FVIII is a recombinant FVIII protein.

[49] The recombinant polypeptide for use according to any embodiment [48], wherein the recombinant FVIII has the natural B domain intact or has the B domain deleted, truncated or modified. Optionally, the recombinant FVIII protein may comprise at least one half-life extending moiety (HLEM). Suitable HLEMs are disclosed herein.

[50] The recombinant polypeptide for use according to embodiment [48], wherein the FVIII protein is a recombinant single-chain Factor VIII, preferably comprising or consisting of the amino acid sequence SEQ ID NO:5 or fragments thereof provided such fragments have FVIII activity.

[51] The recombinant polypeptide for use according to embodiment [48], wherein the recombinant FVIII has the B domain deleted or truncated provided that said deleted or truncated B domain comprises a heterologous insertion of at least one linker peptide and/or a half-life enhancing polypeptide.

[52] The recombinant polypeptide for use according to any one of the preceding embodiments, wherein, when FVIII is administered extravascularly, the bioavailability of the administered FVIII following co-administration with the recombinant polypeptide is increased by the recombinant polypeptide when compared to a reference treatment wherein said reference treatment is identical to said treatment, except the FVIII is administered without said recombinant polypeptide. Thereby, extravascular administration of the recombinant polypeptide provides for or increases bioavailability of the administered FVIII. Preferably, subcutaneous co-administration of the recombinant polypeptide together with FVIII allows for extravascular administration of a FVIII associated with relevant absorption of FVIII into the bloodstream resulting in FVIII activity levels not only significantly above the detection limit, but furthermore suitable for therapeutic application. Preferably, the recombinant polypeptide when co-administered with FVIII not only has a sufficiently long half-life, increases maintenance of FVIII in plasma once it reached this compartment, but also provides bioavailability of FVIII suitable for therapeutic application.

[53] The recombinant polypeptide for use according to any one of the preceding embodiments, wherein the bioavailability of extravascular administered FVIII following co-administration with the recombinant polypeptide is at least 2%, at least 3%, at least 5%, preferably at least 7%, at least 10%, at least 15%, at least 20%, at least 25%, at least 30%, at least 35% or at least 40%.

[54] The recombinant polypeptide for use according to any one of the preceding embodiments, wherein the bioavailability of the recombinant polypeptide is at least 30%, preferably at least 35%, more preferably at least 40%, at least 45%, at least 50%, at least 55%, at least 60%, at least 65%, at least 70%, or at least 80%.

[55] The recombinant polypeptide for use according to any one of the preceding embodiments, wherein the dosage of co-administered FVIII protein does not exceed 2500 IU/kg, preferably does not exceed 2000 IU/kg, does not exceed 1500 IU/kg, does not exceed 1000 IU/kg, does not exceed 600 IU/kg, does not exceed 500 IU/kg or does not exceed 400 IU/kg.

[56] The recombinant polypeptide for use according to any one of the preceding embodiments, wherein following co-administration of said recombinant polypeptide with FVIII the maximal concentration ($C_{max}$) for FVIII is at 10 mIU/mL, at least 25 mIU/mL, at least 50 mIU/mL, at least 100 mIU/mL, at least 200 mIU/mL, at least 300 mIU/mL or at least 400 mIU/mL FVIII activity, preferably chromogenic FVIII activity.

[57] The recombinant polypeptide for use according to any one of the preceding embodiments, wherein following co-administration of said recombinant polypeptide with FVIII the maximal concentration ($C_{max}$) for the recombinant polypeptide is at least 20 nmol/kg, at least 40 nmol/kg, at least 60 nmol/kg, at least 80 nmol/kg or at least 160 nmol/kg. Preferably, following co-administration of said recombinant polypeptide with FVIII the maximal concentration ($C_{max}$) for the recombinant polypeptide is at least 5 µg HLEM/mL, at least 10 µg HLEM/mL, at least 15 µg HLEM/mL, or at least 20 µg HLEM/mL, whereby the values are based on a calculation for the HLEM, preferably, the values are based on a quantitation using a HLEM specific assay such as an immunoassay, preferably specific for human albumin. A further preferred embodiment pertains to the recombinant polypeptide for use according to any one of the preceding embodiments, wherein following co-administration of said recombinant polypeptide with FVIII the maximal concentration ($C_{max}$) for the recombinant polypeptide is at least 3 fold higher as compared to a reference treatment, wherein said reference treatment is identical to said treatment, except that the recombinant polypeptide to be administered does not comprise a HLEM and/or except that the molar ratio of the recombinant polypeptide to be administered to the FVIII to be administered is below a molar ratio according to the invention.

[58] The recombinant polypeptide for use according to any one of the preceding embodiments, wherein following co-administration of said recombinant polypeptide with FVIII the area under the concentration over time curve from t=0 to t=∞ ($AUC_{0-inf}$) for the co-administered FVIII is at least 1,000 mIU*h/mL, at least 2,000 mIU*h/mL, at least 3,000 mIU*h/mL, at least 5,000 mIU*h/mL, at least 10,000 mIU*h/mL or at least 20,000 mIU*h/mL FVIII activity, preferably chromogenic FVIII activity.

[59] The recombinant polypeptide for use according to any one of the preceding embodiments, wherein following co-administration of said recombinant polypeptide with FVIII the area under the concentration over time curve from t=0 to t=∞ ($AUC_{0-inf}$) for the co-administered recombinant polypeptide is at least 2 nmol*h/mL, at least 3 nmol*h/mL, at least 4 nmol*h/mL, at least 20 nmol*h/mL, at least 40 nmol*h/mL, or at least 80 nmol*h/mL. Preferably, following co-administration of said recombinant polypeptide with FVIII the area under the concentration over time curve from t=0 to t=∞ ($AUC_{0-inf}$) for the co-administered recombinant polypeptide is at least 500 µg HLEM*h/mL, at least 750 µg HLEM*h/mL, at least 1,000 µg HLEM*h/mL at least 5,000 µg HLEM*h/mL, or at least 10,000 µg HLEM*h/mL, whereby the values are based on a calculation for the HLEM, preferably, the values are based on a quantitation using a HLEM specific assay such as an immunoassay, preferably specific for human albumin. A further preferred embodiment pertains to the recombinant polypeptide for use according to any one of the preceding embodiments, wherein following co-administration of said recombinant polypeptide with FVIII the area under the concentration over time curve from t=0 to t=∞ ($AUC_{0-inf}$) for the co-administered recombinant polypeptide is at least 5, is at least 10 or is at least 15 fold higher as compared to a reference treatment, wherein said reference treatment is identical to said treatment, except that the recombinant polypeptide to be administered does not comprise a HLEM and/or except that the molar ratio of the recombinant polypeptide to be administered to the FVIII to be administered is below a molar ratio according to the invention.

[60] The recombinant polypeptide for use according to any one of the preceding embodiments, wherein following co-administration of said recombinant polypeptide with FVIII the clearance (CL) value of the recombinant polypeptide amounts to a range between 1.0 to 2.5 mL/kg/h, or between 1.1 to 2.2 mL/kg/h or between 1.2 to 2.1 mUkg/h.

[61] The recombinant polypeptide for use according to any one of the preceding embodiments, wherein following co-administration of said recombinant polypeptide with FVIII the clearance (CL) value for the recombinant polypeptide is reduced by a factor of at least 2, at least 5, or at least 10, as compared to a reference treatment, wherein said reference treatment is identical to said treatment, except that the recombinant polypeptide to be administered does not comprise a HLEM and/or except that the molar ratio of the recombinant polypeptide to be administered to the FVIII to be administered is below a molar ratio according to the invention.

[62] The recombinant polypeptide for use according to any one of the preceding embodiments, wherein following co-administration of said recombinant polypeptide with FVIII the clearance (CL) value of the administered FVIII is reduced compared to a reference treatment, preferably by a factor of at least 1.5, at least 2, at least 3, at least 5, at least 7.5 or at least 10, wherein said reference treatment is identical to said treatment, except that the recombinant polypeptide to be administered does not comprise a HLEM and/or except that the molar ratio of the recombinant polypeptide to be administered to the FVIII to be administered is below a molar ratio according to the invention.

[63] The recombinant polypeptide for use according to any one of the preceding embodiments, wherein following co-administration of said recombinant polypeptide with FVIII the clearance (CL) value of the administered FVIII is below 135 mUkg/h, below 80 mL/kg/h, below 45 mL/kg/h, below 40 mL/kg/h, below 35 mL/kg/h, below 30 mL/kg/h or below 25 mL/kg/h. The clearance (CL) value of the administered FVIII is preferably lower than that of a reference treatment, wherein said reference treatment is identical to said treatment, except that the recombinant polypeptide to be administered does not comprise a HLEM and/or except that the molar ratio of the recombinant polypeptide to be administered to the FVIII to be administered is lower below a molar ratio according to the invention.

[64] The recombinant polypeptide for use according to any one of the preceding embodiments, wherein the molar ratio of the recombinant polypeptide to the FVIII to be administered is at least 75, at least 100, at least 200, at least 300, at least 400, at least 500 or at least 1000.

[65] The recombinant polypeptide for use according to any one of the preceding embodiments, wherein the recombinant polypeptide is administered at an amount of at least 0.01 mg/kg, at least 0.1 mg/kg, at least 0.2 mg/kg, at least 0.5 mg/kg, at least 1 mg/kg or at least 3 mg/kg recombinant polypeptide.

[66] The recombinant polypeptide for use according to any one of the preceding embodiments, wherein the recombinant polypeptide is administered with an amount not exceeding 20 mg/kg, not exceeding 15 mg/kg, not exceeding 10 mg/kg, or not exceeding 5 mg/kg of the recombinant polypeptide.

[67] A pharmaceutical composition for use in the treatment or prophylaxis of a blood coagulation disorder as defined in any one of embodiments [1] to [66], the composition comprising
(i) a recombinant polypeptide comprising a truncated von Willebrand Factor (VWF) according to any one of embodiments [1] to [7] or any one of embodiments [9] to [66] provided that the recombinant polypeptide and the FVIII are to be administered via the same route of administration, and
(ii) a Factor VIII protein (FVIII),
wherein the molar ratio of the recombinant polypeptide to the FVIII within the composition is greater than 50.

[68] A pharmaceutical composition for use according to embodiment [67], wherein said treatment comprising administering the composition extravascular to a subject with a blood coagulation disorder, and
said pharmaceutical composition is formulated suitable for extravascular co-administration. Preferably, at least portions of said recombinant polypeptide are bound to FVIII. According to a further preferred embodiment of the pharmaceutical composition, said recombinant polypeptide is non-covalently bound to FVIII. Preferably, the pharmaceutical composition comprises a high proportion of dimers of said polypeptide. Further preferred is that the pharmaceutical composition does not comprise monomer and/or multimer forms of the polypeptide or at least is essentially free of monomer and/or multimer forms of the polypeptide.

[69] A pharmaceutical kit comprising (i) a first composition comprising a Factor VIII protein (FVIII) and (ii) a second composition comprising a recombinant polypeptide comprising a truncated von Willebrand Factor (VWF) for use according to any one of embodiments [1] to [66] for use in the treatment or prophylaxis of a blood coagulation disorder, said treatment comprising administering the recombinant polypeptide and the FVIII protein, preferably extravascular, to a subject having the blood coagulation disorder, wherein said FVIII and said recombinant polypeptide are provided within the kit. Preferably, said FVIII and said recombinant polypeptide are provided within the kit in order to allow prior to administration for at least a proportion of said recombinant polypeptide to bind to said FVIII, and provided that the molar ratio of the recombinant polypeptide to be administered to the FVIII to be administered is higher than 50. Preferably, the second composition comprises a high proportion of dimers of said polypeptide. Further preferred is that the second composition does not comprise monomer and/or multimer forms of the polypeptide or at least is essentially free of monomer and/or multimer forms of the polypeptide.

[70] A method of treatment or prophylaxis of a blood coagulation disorder, the method comprising co-administering an effective amount of a recombinant polypeptide comprising a truncated von Willebrand Factor (VWF) and a Factor VIII protein (FVIII) to a subject having the blood coagulation disorder, wherein said recombinant polypeptide is capable of binding to said FVIII, and wherein the molar ratio of the recombinant polypeptide to be administered to the FVIII to be administered is higher than 50. The recombinant polypeptide within this method may preferably be provided according to any one of embodiments [1] to [66]. Said polypeptide may be administered subcutaneously, intradermally or intramuscularly. The FVIII may be also administered subcutaneously, intradermally or intramuscularly. Preferably, both FVIII and said polypeptide are administered subcutaneously. According to another variation of the method, the FVIII is administered via a different route of administration than the recombinant polypeptide, preferably FVIII is then administered intravenously, more specifically the recombinant polypeptide is administered subcutaneously and the FVIII is administered intravenously.

[71] A method of treatment or prophylaxis of a blood coagulation disorder, the method comprising administering an effective amount of a recombinant polypeptide comprising a truncated von Willebrand Factor (VWF) and a Factor VIII protein (FVIII) via different routes of administration to a subject having the blood coagulation disorder, wherein said recombinant polypeptide is capable of binding to FVIII. The recombinant polypeptide within this method may be provided according to any one of embodiments [2] to [66]. Within this embodiment, the determination of the molar ratio of the recombinant polypeptide to the FVIII is not obligatory before administration of the recombinant polypeptide. Preferably, the FVIII is administered intravenously, more preferred the recombinant polypeptide is administered subcutaneously and the FVIII is administered intravenously.

[72] The use of a recombinant polypeptide as defined in any one of embodiments [1] to [66] for the treatment or prophylaxis of a blood coagulation disorder, said recombinant polypeptide comprising a truncated von Willebrand Factor (VWF), said treatment or prophylaxis comprising administering the polypeptide and a Factor VIII (FVIII) protein, preferably extravascular, to a subject, wherein said recombinant polypeptide is capable of binding to said FVIII. The molar ratio of the recombinant polypeptide to be administered to the FVIII to be administered is preferably higher than 50.

[73] Use of a recombinant polypeptide comprising a truncated von Willebrand Factor (VWF) for the manufacture of a medicament for the treatment or prophylaxis of a blood coagulation disorder, said treatment or prophylaxis comprising administering the recombinant polypeptide and a Factor VIII (FVIII) protein, preferably extravascular, to a subject, wherein said recombinant polypeptide is capable of binding to said FVIII, and wherein the molar ratio of the recombinant polypeptide to be administered to the FVIII to be administered is higher than 50 provided that said recombinant polypeptide is defined according to any one of embodiments [1] to [66].

DETAILED DESCRIPTION

Figure 1:
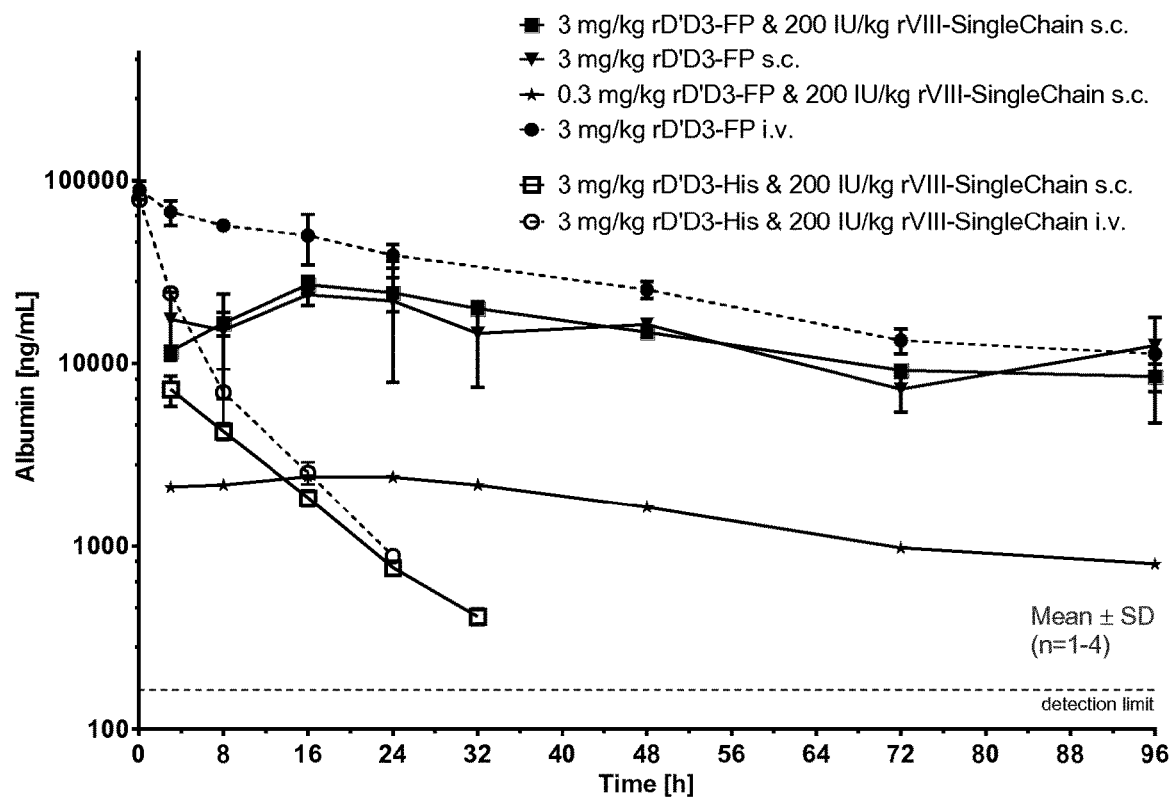
FIG. 1 shows levels of the recombinant polypeptide comprising a truncated von Willebrand Factor (VWF) (hereinafter also: recombinant polypeptide) after subcutaneous or intravenous administration of rD'D3-FP or rD'D3-His with or without recombinant FVIII in FVIII ko mice. rD'D3-FP was quantified via its albumin component, and rD'D3-His data are calculated to equimolar concentrations. Data is given as mean±SD for n=1-4 mice per timepoint. Solid lines represent s.c. and dotted lines i.v. treatment. Abbreviation: s.c.: subcutaneous; i.v.: intravenous.

In a first aspect, the present invention relates to a recombinant polypeptide comprising a truncated von Willebrand Factor (VWF) for use in the treatment or prophylaxis of a blood coagulation disorder, said treatment comprising administering the recombinant polypeptide and a Factor VIII (FVIII) protein extravascular to a subject having a blood coagulation disorder, wherein said recombinant polypeptide is capable of binding to said FVIII, and wherein the molar ratio of the recombinant polypeptide to be administered to the FVIII to be administered is higher than 50.

In a second aspect, the present invention pertains to a pharmaceutical composition for use in the treatment or prophylaxis of a blood coagulation disorder, the composition comprising
(i) the recombinant polypeptide of the invention comprising a truncated von Willebrand Factor (VWF), and
(ii) a Factor VIII protein (FVIII),
wherein the molar ratio of the recombinant polypeptide to the FVIII protein within the pharmaceutical composition is greater than 50 and wherein said recombinant polypeptide is capable of binding to said FVIII, said treatment comprising administering the pharmaceutical composition extravascular to a subject having a blood coagulation disorder, and said pharmaceutical composition is formulated for extravascular co-administration.

In a third aspect, the present invention pertains to a pharmaceutical kit comprising (i) a first composition comprising a Factor VIII (FVIII) protein and (ii) a second composition comprising the recombinant polypeptide of the invention comprising a truncated von Willebrand Factor (VWF) for use in the treatment or prophylaxis of a blood coagulation disorder as presented herein, said treatment comprising administering the recombinant polypeptide and the FVIII protein extravascular to a subject, wherein said FVIII and said recombinant polypeptide are provided within the kit in order to allow prior to administration for at least a proportion of said recombinant polypeptide to bind to said FVIII, and provided that the molar ratio of the recombinant polypeptide to be administered to the FVIII to be administered is higher than 50.

According to a fourth aspect, the present invention pertains to a method of treatment or prophylaxis of a blood coagulation disorder, the method comprising co-administering an effective amount of the recombinant polypeptide of the invention comprising a truncated von Willebrand Factor (VWF) and a Factor VIII (FVIII) protein extravascular to a subject, wherein said recombinant polypeptide is capable of binding to said FVIII, and wherein the molar ratio of the recombinant polypeptide to be administered to the FVIII to be administered is higher than 50.

In a fifth aspect, the present invention relates to the use of the recombinant polypeptide according to the invention for the treatment or prophylaxis of a blood coagulation disorder, said recombinant polypeptide comprising a truncated von Willebrand Factor (VWF), said treatment comprising administering the polypeptide and a Factor VIII (FVIII) protein extravascular to a subject, wherein said recombinant polypeptide is capable of binding to said FVIII, and wherein the molar ratio of the recombinant polypeptide to be administered to the FVIII to be administered is higher than 50.

According to a further aspect, the present invention pertains to the use of the recombinant polypeptide comprising a truncated von Willebrand Factor (VWF) for the manufacture of a medicament for the treatment or prophylaxis of a blood coagulation disorder, said treatment comprising administering the polypeptide and a Factor VIII (FVIII) protein extravascular to a subject, wherein said recombinant polypeptide is capable of binding to said FVIII, and wherein the molar ratio of the recombinant polypeptide to be administered to the FVIII to be administered is higher than 50.

The polypeptide comprising a truncated von Willebrand Factor (VWF) will be referred to herein as "polypeptide of the invention" or "recombinant polypeptide". The polypeptide of the invention preferably comprises a half-life extending moiety (HELM).

Ratios

As described in more detail below, the polypeptide of the invention may be a monomer, a dimer, or a mixture thereof. Any molar ratios according to the invention refer to a ratio of the molar concentration of the monomeric subunit of the polypeptide of the invention, whether actually present as monomer or dimer. Ratios are formed over the molar concentration of the co-administered FVIII. Any ratios of the polypeptide of the invention over FVIII in this application refer to the amount of monomers comprised in the polypeptide of the invention, which is preferably present as a dimer, to be administered (in mole) divided by the amount of FVIII to be administered (in mole), unless indicated otherwise. By way of non-limiting example the co-administration of 100 µM of a monomeric polypeptide of the invention with 1 µM of FVIII means a ratio of 100. The same ratio of 100 is obtained if 50 µM of a dimeric polypeptide of the invention are co-administered with 1 µM of FVIII.

The molar ratio of the polypeptide of the invention to be administered to FVIII to be administered is above 50, more preferably the ratio is greater than 60, or at least 75, at least 100, or greater than 100, or at least 200, most preferably at least 300, or at least 400, or at least 500, or at least 600, or at least 700, or at least 800, or at least 900, or at least 1,000, or at least 1,100, or at least 1,200, or at least 1,300, or at least 1,400, or at least 1,500, or at least 1,600, or at least 1,700, or at least 1,800, or at least 1,900, or at least 2,000, or at least 2,500, or at least 3,000 or at least 5,000, or at least 8,000 or up to 10,000. The molar ratio of the polypeptide of the invention to be administered to FVIII to be administered may according to certain embodiments not exceed a ratio of 10,000, a ratio of 5,000, a ratio of 2,500 or a ratio of 2,000.

The molar ratio of the polypeptide of the invention to be administered to FVIII to be administered may range from above 50 to 10,000, or from above 50 to 5,000, or from above 50 to 4,000, or from above 50 to 3,000, or from above 50 to 2,000, or from above 50 to 1,000. Preferably, the molar ratio of the polypeptide of the invention to be administered to FVIII to be administered ranges from 60 to 2,500, or from 110 to 2,000, or from 150 to 1,500, or from 200 to 1,000.

Normal human plasma (NHP) contains VWF in a concentration of 1 U/mL or 100% by definition. This corresponds to a protein concentration of approximately 10 µg/mL (Haberichter S. L. and Montgomery R. R., Structure and function of von Willebrand factor; in: Hemostasis and Thrombosis, eds. Marder, Aird, Bennett, Schulman and White, Lippincott Williams & Wilkins 2013, pp 197-207). Based on this VWF concentration in NHP and a molecular weight of the mature VWF monomer of approximately 267,500 Da including 18-19% of glycosylation a molar plasma concentration of the VWF monomer unit of approximately $37 \times 10^{-9}$ Mol/L can be calculated for NHP. The half-life of endogenous VWF in human plasma is about 16 h (Lenting P J, Christophe O D, Denis C V. von Willebrand factor biosynthesis, secretion, and clearance: connecting the far ends. Blood. 2015.125(13):2019-28).

Further details of the treatment in accordance with the invention are described further below.

The Truncated VWF

The term "von Willebrand Factor" (VWF) as used herein includes naturally occurring (native) VWF, but also variants thereof retaining at least the FVIII binding activity of naturally occurring VWF, e.g. sequence variants where one or more residues have been inserted, deleted or substituted. The FVIII binding activity is determined by a FVIII-VWF binding assay as described in Example 2.

A preferred VWF in accordance with this invention is human VWF represented by the amino acid sequence shown in SEQ ID NO:4. The cDNA encoding SEQ ID NO:4 is shown in SEQ ID NO:3.

The gene encoding human native VWF is transcribed into a 9 kb mRNA which is translated into a pre-propolypeptide of 2813 amino acids with an estimated molecular weight of 310,000 Da. The pre-propolypeptide contains an N-terminal 22 amino acids signal peptide, followed by a 741 amino acid pro-polypeptide (amino acids 23-763 of SEQ ID NO:4) and the mature subunit (amino acids 764-2813 of SEQ ID NO:4). Cleavage of the 741 amino acids propolypeptide from the N-terminus results in mature VWF consisting of 2050 amino acids. The amino acid sequence of the human native VWF pre-propolypeptide is shown in SEQ ID NO:4. Unless indicated otherwise, the amino acid numbering of VWF residues in this application refers to SEQ ID NO:4, even if the VWF molecule, in particular a truncated VWF, does not comprise all residues of SEQ ID NO:4.

The propolypeptide of native VWF comprises multiple domains. Different domain annotations can be found in the literature (see, e.g. Zhou et al. (2012) Blood 120(2): 449-458). The following domain annotation of native pre-propolypeptide of VWF is applied in this application:

D1-D2-D'-D3-A1-A2-A3-D4-C1-C2-C3-C4-C5-C6-CK

With reference to SEQ ID NO:4, the D' domain consists of amino acids 764-865; and the D3 domain consists of amino acids 866-1242.

The feature "truncated" in terms of present invention means that the polypeptide does not comprise the entire amino acid sequence of mature VWF (amino acids 764-2813 of SEQ ID NO:4). Typically, the truncated VWF does not comprise all amino acids 764-2813 of SEQ ID NO:4 but only a fragment thereof. A truncated VWF may also be referred to as a VWF fragment, or in the plural as VWF fragments.

Typically, the truncated VWF is capable of binding to a Factor VIII. Preferably, the truncated VWF is capable of binding to the mature form of human native Factor VIII. In another embodiment, the truncated VWF is capable of binding to a recombinant FVIII, preferably to a FVIII as described herein, further preferred to a the single-chain Factor VIII consisting of the amino acid sequence SEQ ID NO:5. Binding of the truncated VWF to Factor VIII can be determined by a FVIII-VWF binding assay as described in Example 2.

The truncated VWF of the present invention preferably comprises or consists of an amino acid sequence having a sequence identity of at least 90% to amino acids 776 to 805 of SEQ ID NO:4 and is capable of binding to FVIII. In preferred embodiments the truncated VWF comprises or consists of an amino acid sequence having a sequence identity of at least 95%, at least 96%, at least 97%, at least 98%, or at least 99%, to amino acids 776 to 805 of SEQ ID NO:4 and is capable of binding to FVIII. Most preferably, the truncated VWF comprises or consists of amino acids 776 to 805 of SEQ ID NO:4. Unless indicated otherwise herein, sequence identities are determined over the entire length of the reference sequence (e.g. amino acids 776 to 805 of SEQ ID NO:4).

The truncated VWF of the present invention preferably comprises or consists of an amino acid sequence having a sequence identity of at least 90% to amino acids 766 to 864 of SEQ ID NO:4 and is capable of binding to FVIII. In preferred embodiments the truncated VWF comprises or consists of an amino acid sequence having a sequence identity of at least 95%, at least 96%, at least 97%, at least 98%, or at least 99%, to amino acids 766 to 864 of SEQ ID NO:4 and is capable of binding to FVIII. Most preferably, the truncated VWF comprises or consists of amino acids 766 to 864 of SEQ ID NO:4.

In another preferred embodiment, the truncated VWF consists of (a) an amino acid sequence having a sequence identity of at least 90% to amino acids 764 to 1242 of SEQ ID NO:4, or (b) a fragment thereof, provided that the truncated VWF is still capable of binding to FVIII. More preferably, the truncated VWF consists of (a) an amino acid sequence having a sequence identity of at least 95%, at least 96%, at least 97%, at least 98%, or at least 99%, to amino acids 764 to 1242 of SEQ ID NO:4, or (b) a fragment thereof, provided that the truncated VWF is still capable of binding to FVIII. Most preferably, the truncated VWF consists of (a) amino acids 764 to 1242 of SEQ ID NO:4, or (b) a fragment thereof, provided that the truncated VWF is still capable of binding to FVIII.

As described in more detail below, the polypeptide of the invention may be prepared by a method which uses cells comprising a nucleic acid encoding the polypeptide comprising the truncated VWF. The nucleic acid is introduced into suitable host cells by techniques that are known per se.

In a preferred embodiment, the nucleic acid in the host cell encodes (a) an amino acid sequence having a sequence identity of at least 90% to amino acids 1 to 1242 of SEQ ID NO:4, or (b) a fragment thereof, provided that the truncated mature VWF is still capable of binding to FVIII. More preferably, the nucleic acid encodes (a) an amino acid sequence having a sequence identity of at least 95%, at least 96%, at least 97%, at least 98%, or at least 99%, to amino acids 1 to 1242 of SEQ ID NO:4, or (b) a fragment thereof, provided that the truncated VWF is still capable of binding to FVIII. Most preferably, the nucleic acid encodes (a) amino acids 1 to 1242 of SEQ ID NO:4, or (b) a fragment thereof, provided that the truncated VWF is still capable of binding to FVIII. Especially if the polypeptide in accordance with this invention is a dimer, the nucleic acid will comprise a sequence encoding amino acids 1 to 763 of VWF (e.g. SEQ ID NO:4), even if the truncated VWF in the polypeptide does not comprise amino acids 1 to 763 of VWF (e.g. SEQ ID NO:4).

The truncated VWF of the recombinant polypeptide of the invention according to a preferred embodiment may not comprise amino acid sequence 1 to 763 of VWF of SEQ ID NO:4.

According to further preferred embodiments, the truncated VWF comprises or consists of one of the following amino acid sequences, each referring to SEQ ID NO:4: 776-805; 766-805; 764-805; 776-810; 766-810; 764-810; 776-815; 766-815; 764-815; 776-820; 766-820; 764-820; 776-825; 766-825; 764-825; 776-830; 766-830; 764-830; 776-835; 766-835; 764-835; 776-840; 766-840; 764-840; 776-845; 766-845; 764-845; 776-850; 766-850; 764-850; 776-855; 766-855; 764-855; 776-860; 766-860; 764-860; 776-864; 766-864; 764-864; 776-865; 766-865; 764-865; 776-870; 766-870; 764-870; 776-875; 766-875; 764-875; 776-880; 766-880; 764-880; 776-885; 766-885; 764-885; 776-890; 766-890; 764-890; 776-895; 766-895; 764-895; 776-900; 766-900; 764-900; 776-905; 766-905; 764-905; 776-910; 766-910; 764-910; 776-915; 766-915; 764-915; 776-920; 766-920; 764-920; 776-925; 766-925; 764-925; 776-930; 766-930; 764-930; 776-935; 766-935; 764-935; 776-940; 766-940; 764-940; 776-945; 766-945; 764-945; 776-950; 766-950; 764-950; 776-955; 766-955; 764-955; 776-960; 766-960; 764-960; 776-965; 766-965; 764-965; 776-970; 766-970; 764-970; 776-975; 766-975; 764-975; 776-980; 766-980; 764-980; 776-985; 766-985; 764-985; 776-990; 766-990; 764-990; 776-995; 766-995; 764-995; 776-1000; 766-1000; 764-1000; 776-1005; 766-1005; 764-1005; 776-1010; 766-1010; 764-1010; 776-1015; 766-1015; 764-1015; 776-1020; 766-1020; 764-1020; 776-1025; 766-1025; 764-1025; 776-1030; 766-1030; 764-1030; 776-1035; 766-1035; 764-1035; 776-1040; 766-1040; 764-1040; 776-1045; 766-1045; 764-1045; 776-1050; 766-1050; 764-1050; 776-1055; 766-1055; 764-1055; 776-1060; 766-1060; 764-1060; 776-1065; 766-1065; 764-1065; 776-1070; 766-1070; 764-1070; 776-1075; 766-1075; 764-1075; 776-1080; 766-1080; 764-1080; 776-1085; 766-1085; 764-1085; 776-1090; 766-1090; 764-1090; 776-1095; 766-1095; 764-1095; 776-1100; 766-1100; 764-1100; 776-1105; 766-1105; 764-1105; 776-1110; 766-1110; 764-1110; 776-1115; 766-1115; 764-1115; 776-1120; 766-1120; 764-1120; 776-1125; 766-1125; 764-1125; 776-1130; 766-1130; 764-1130; 776-1135; 766-1135; 764-1135; 776-1140; 766-1140; 764-1140; 776-1145; 766-1145; 764-1145; 776-1150; 766-1150; 764-1150; 776-1155; 766-1155; 764-1155; 776-1160; 766-1160; 764-1160; 776-1165; 766-1165; 764-1165; 776-1170; 766-1170; 764-1170; 776-1175; 766-1175; 764-1175; 776-1180; 766-1180; 764-1180; 776-1185; 766-1185; 764-1185; 776-1190; 766-1190; 764-1190; 776-1195; 766-1195; 764-1195; 776-1200; 766-1200; 764-1200; 776-1205; 766-1205; 764-1205; 776-1210; 766-1210; 764-1210; 776-1215; 766-1215; 764-1215; 776-1220; 766-1220; 764-1220; 776-1225; 766-1225; 764-1225; 776-1230; 766-1230; 764-1230; 776-1235; 766-1235; 764-1235; 776-1240; 766-1240; 764-1240; 776-1242; 766-1242; 764-1242; 764-1464; 764-1250; 764-1041; 764-828; 764-865; 764-1045; 764-1035; 764-1128; 764-1198; 764-1268; 764-1261; 764-1264; 764-1459; 764-1463; 764-1464; 764-1683; 764-1873; 764-1482; 764-1479; 764-1672; and 764-1874.

In certain embodiments the truncated VWF has an internal deletion relative to mature wild type VWF. For example, the A1, A2, A3, D4, C1, C2, C3, C4, C5, C6, CK domains or combinations thereof may be deleted, and the D' domain and/or the D3 domain is retained. According to further embodiments, the truncated VWF lacks one or more of the domains A1, A2, A3, D4, C1, C2, C3, C4, C5, C6 or CK. According to further embodiments, the truncated VWF lacks amino acids 1243 to 2813 of SEQ ID NO:4, i.e. the domains A1-A2-A3-D4-C1-C2-C3-C4-C5-C6-CK.

In further embodiments the truncated VWF does not comprise the binding sites for platelet glycoprotein Ibα (GPIbα), collagen and/or integrin αIIbβIII (RGDS sequence within the C1 domain). In other embodiments, the truncated VWF does not comprise the cleavage site (Tyr1605-Met1606) for ADAMTS13 which is located at the central A2 domain of VWF. In yet another embodiment, the truncated VWF does not comprise the binding sites for GPIbα, and/or does not comprise the binding site for collagen, and/or does not comprise the binding site for integrin αIIbβIII, and/or it does not comprise the cleavage site (Tyr1605-Met1606) for ADAMTS13 which is located at the central A2 domain of VWF.

In other embodiments the truncated VWF comprises or consists of an amino acid sequence that has a sequence identity of at least 90%, or at least 91%, or at least 92%, or at least 93%, or at least 94%, or at least 95%, or at least 96%, or at least 97%, or at least 98%, or at least 99%, to one of the amino acid sequences recited in the preceding paragraph, provided that the truncated VWF is capable of binding to FVIII.

A polypeptide of the invention is termed a "dimer" in the present invention if two monomers of the polypeptide of the invention are linked covalently. Preferably, the covalent bond is located within the truncated VWF portion of the polypeptide of the invention. Preferably, the two monomeric subunits are covalently linked via at least one disulfide bridge, e.g. by one, two, three or four disulfide bridges. The cysteine residues forming the at least one disulfide bridge are preferably located within the truncated VWF portion of the polypeptide of the invention. In one embodiment, these cysteine residues are Cys-1099, Cys-1142, Cys-1222, Cys-1225, or Cys-1227 or combinations thereof. Preferably, the dimeric polypeptide of the invention does not comprise any further covalent bond linking the monomers in addition to said covalent bond located within the truncated VWF portion of the polypeptide, in particular does not comprise any further covalent bond located within the HLEM or HLEP portion of the polypeptide. According to alternative embodiments, however, the dimeric polypeptide of the invention may comprise a covalent bond located in the HLEM or HLEP portion of the polypeptide linking the monomers.

The dimer is preferably a homo-dimer, whereby each monomer comprises preferably a HLEM as disclosed herein. If the polypeptide of the invention is a dimer, the truncated VWF preferably comprises or consists of two polypeptides each with an amino acid sequence having a sequence identity of at least 90% to amino acids 764 to 1099, amino acids 764 to 1142, amino acids 764 to 1222, amino acids 764 to 1225, or amino acids 764 to 1227 of SEQ ID NO:4 and is capable of binding to FVIII. In preferred embodiments the truncated VWF comprises or consists of an amino acid sequence having a sequence identity of at least 95%, at least 96%, at least 97%, at least 98%, or at least 99%, to amino acids 764 to 1099, amino acids 764 to 1142, amino acids 764 to 1222, amino acids 764 to 1225, or amino acids 764 to 1227 of SEQ ID NO:4 and is capable of binding to FVIII. Most preferably, the truncated VWF comprises or consists of amino acids 764 to 1099, amino acids 764 to 1142, amino acids 764 to 1222, amino acids 764 to 1225, amino acids 764 to 1227 or amino acids 764 to 1242 of SEQ ID NO:4.

The truncated VWF may be any one of the VWF fragments disclosed in WO 2013/106787 A1, WO 2014/198699 A2, WO 2011/060242 A2 or WO 2013/093760 A2, the disclosure of which is incorporated herein by reference.

According to further preferred embodiments the truncated VWF as disclosed above may comprise at least one of the amino acid substitutions as disclosed in WO 2016/000039 A1. Those modified versions of the truncated VWF comprise at least one amino acid substitution within its D' domain, as compared to the amino acid sequence of the D' domain of wild-type VWF according to SEQ ID NO: 4. The amino acid sequence of the modified versions of the truncated VWF can have one or more amino acid substitutions relative to the respective wild type sequence. The amino acid sequence of the D' domain of the modified truncated VWF preferably has one or 2 amino acid substitutions relative to the D' domain of SEQ ID NO:4. It is preferred that S at position 764 of SEQ ID NO:4, corresponding to position 1 of SEQ ID NO:2, is substituted with an amino acid selected from the group consisting of G, P, V, E, Y, A and L. It is also preferred that S at position 766 of SEQ ID NO:4, corresponding to position 3 of SEQ ID NO:2 is substituted with an amino acid selected from the group consisting of Y, I, M, V, F, H, R and W. Preferred combinations of substitutions include S764G/S766Y, S764P/S766I, S764P/S766M, S764V/S766Y, S764E/S766Y, S764Y/S766Y, S764 L/S766Y, S764P/S766W, S766W/S806A, S766Y/P769K, S766Y/P769N, S766Y/P769R and S764P/S766 L, referring to the sequence of SEQ ID NO:4. The binding affinity of the polypeptide of the present invention to FVIII may be further increased by introduction of said substitutions compared to the binding affinity of a reference polypeptide which has the same amino acid sequence except for said modifications. Said substitutions within the truncated VWF may contribute to increase the half-life of co-administered FVIII.

The term "endogenous VWF" as used herein refers to monomeric subunits of VWF, independent of its degree of multimerization.

Half-Life Extending Moiety (HLEM)

In addition to the truncated VWF, the polypeptide of the invention may in certain preferred embodiments further comprise a half-life extending moiety. The half-life-extending moiety may be a heterologous amino acid sequence fused to the truncated VWF. Alternatively, the half-life-extending moiety may be chemically conjugated to the polypeptide comprising the truncated VWF by a covalent bond different from a peptide bond.

In certain embodiments of the invention, the half-life of the polypeptide of the invention is extended by chemical modification, e.g. attachment of a half-life extending moiety such as polyethylene glycol (PEGylation), glycosylated PEG, hydroxyl ethyl starch (HESylation), polysialic acids, elastin-like polypeptides, heparosan polymers or hyaluronic acid. In another embodiment, the polypeptide of the invention is conjugated to a HLEM such as albumin via a chemical linker. The principle of this conjugation technology has been described in an exemplary manner by Conjuchem LLC (see, e.g., U.S. Pat. No. 7,256,253).

In other embodiments, the half-life-extending moiety is a half-life enhancing protein (HLEP). Preferably, the HLEP is an albumin or a fragment thereof. The N-terminus of the albumin may be fused to the C-terminus of the truncated VWF. Alternatively, the C-terminus of the albumin may be fused to the N-terminus of the truncated VWF. One or more HLEPs may be fused to the N- or C-terminal part of VWF provided that they do not to interfere with or abolish the binding capability of the truncated VWF to FVIII.

The recombinant polypeptide further comprises preferably a chemical bond or a linker sequence positioned between the truncated VWF and the HLEM.

Said linker sequence may be a peptidic linker consisting of one or more amino acids, in particular of 1 to 50, 1 to 30, 1 to 20, 1 to 15, 1 to 10, 1 to 5 or 1 to 3 (e.g. 1, 2 or 3) amino acids and which may be equal or different from each other. Preferably, the linker sequence is not present at the corresponding position in the wild-type VWF. Preferred amino acids present in said linker sequence include Gly and Ser. The linker sequence should be non-immunogenic. Preferred linkers may be comprised of alternating glycine and serine residues. Suitable linkers are described for example in WO2007/090584.

In another embodiment of the invention the peptidic linker between the truncated VWF moiety and the HLEM consists of peptide sequences, which serve as natural interdomain linkers in human proteins. Preferably such peptide sequences in their natural environment are located close to the protein surface and are accessible to the immune system so that one can assume a natural tolerance against this sequence. Examples are given in WO 2007/090584. Cleavable linker sequences are described, e.g., in WO 2013/120939 A1.

In a preferred embodiment of the recombinant polypeptide the linker between the truncated VWF and the HLEM is a glycine/serine peptidic linker having or consisting of amino acid sequence 480-510 of SEQ ID NO:2.

In one embodiment the polypeptide has the following structure:

tVWF-L1-H, [formula 1]

Wherein tVWF is the truncated VWF, L1 is a chemical bond or a linker sequence, and H is a HLEM, in particular a HLEP.

L1 may be a chemical bond or a linker sequence consisting of one or more amino acids, e.g. of 1 to 50, 1 to 30, 1 to 20, 1 to 15, 1 to 10, 1 to 5 or 1 to 3 (e.g. 1, 2 or 3) amino acids and which may be equal or different from each other. Usually, the linker sequences are not present at the corresponding position in the wild-type VWF. Examples of suitable amino acids present in L1 include Gly and Ser. The linker should be non-immunogenic and may be a non-cleavable or cleavable linker. Non-cleavable linkers may be comprised of alternating glycine and serine residues as exemplified in WO 2007/090584 A1. In another embodiment of the invention the peptidic linker between the truncated VWF moiety and the albumin moiety consists of peptide sequences, which serve as natural interdomain linkers in human proteins. Preferably such peptide sequences in their natural environment are located close to the protein surface and are accessible to the immune system so that one can assume a natural tolerance against this sequence. Examples are given in WO2007/090584. Cleavable linker sequences are described, e.g., in WO 2013/120939 A1.

Preferred HLEP sequences are described infra. Likewise encompassed by the invention are fusions to the exact "N-terminal amino acid" or to the exact "C-terminal amino acid" of the respective HLEP, or fusions to the "N-terminal part" or "C-terminal part" of the respective HLEP, which includes N-terminal deletions of one or more amino acids of the HLEP. The polypeptide may comprise more than one HLEP sequence, e.g. two or three HLEP sequences. These multiple HLEP sequences may be fused to the C-terminal part of VWF in tandem, e.g. as successive repeats.

Half-Life Enhancing Polypeptides (HLEPs)

Preferably, the half-life extending moiety is a half-life extending polypeptide (HLEP). More preferably the HLEP is selected from the group consisting of albumin, a member of the albumin-family or fragments thereof, solvated random chains with large hydrodynamic volume (e.g. XTEN (Schellenberger et al. 2009; Nature Biotechnol. 27:1186-1190), homo-amino acid repeats (HAP) or proline-alanine-serine repeats (PAS), afamin, alpha-fetoprotein, Vitamin D binding protein, transferrin or variants or fragments thereof, carboxyl-terminal peptide (CTP) of human chorionic gonadotropin-β subunit, a polypeptide capable of binding to the neonatal Fc receptor (FcRn), in particular an immunoglobulin constant region and portions thereof, e.g. the Fc fragment, polypeptides or lipids capable of binding under physiological conditions to albumin, to a member of the albumin-family or to fragments thereof or to an immunoglobulin constant region or portions thereof. The immunoglobulin constant region or portions thereof is preferably an Fc fragment of immunoglobulin G1, an Fc fragment of immunoglobulin G2 or an Fc fragment of immunoglobulin A.

A half-life enhancing polypeptide as used herein may be a full-length half-life-enhancing protein described herein or one or more fragments thereof that are capable of stabilizing or prolonging the therapeutic activity or the biological activity of the coagulation factor, in particular of increasing the in vivo half-life of the polypeptide of the invention. Such fragments may be of 10 or more amino acids in length or may include at least about 15, at least about 20, at least about 25, at least about 30, at least about 50, at least about 100, or more contiguous amino acids from the HLEP sequence or may include part or all of specific domains of the respective HLEP, as long as the HLEP fragment provides a functional half-life extension of at least 25% compared to the respective polypeptide without the HLEP.

The HLEP portion of the polypeptide of the invention may be a variant of a wild type HLEP. The term "variants" includes insertions, deletions and substitutions, either conservative or non-conservative, where such changes do not substantially alter the FVIII-binding activity of the truncated VWF.

In particular, the proposed truncated VWF-HLEP fusion constructs of the invention may include naturally occurring polymorphic variants of HLEPs and fragments of HLEPs. The HLEP may be derived from any vertebrate, especially any mammal, for example human, monkey, cow, sheep, or pig. Non-mammalian HLEPs include, but are not limited to, hen and salmon.

According to certain embodiments of present disclosure the HLEM, in particular a HLEP, portion of the recombinant polypeptide of the invention may be specified with the alternative term "FP". Preferably, the term "FP" represents a human albumin.

According to certain preferred embodiments, the recombinant polypeptide is a fusion protein. A fusion protein in terms of present invention is a protein created by in-frame joining of at least two DNA sequences encoding the truncated VWF as well as the HLEP. The skilled person understands that translation of the fusion protein DNA sequence will result in a single protein sequence. As a result of an in frame insertion of a DNA sequence encoding a peptidic linker according to a further preferred embodiment, a fusion protein comprising the truncated VWF, a suitable linker and the HELP may be obtained.

According to some embodiments, the co-administered FVIII does neither comprise any of the herein described HLEM or HLEP structures. According to certain other embodiments, the co-administered FVIII may comprise at least one of the herein described HLEM or HLEP structures.

Albumin as HLEP

The terms, "human serum albumin" (HSA) and "human albumin" (HA) and "albumin" (ALB) are used interchangeably in this application. The terms "albumin" and "serum albumin" are broader, and encompass human serum albumin (and fragments and variants thereof) as well as albumin from other species (and fragments and variants thereof).

As used herein, "albumin" refers collectively to albumin polypeptide or amino acid sequence, or an albumin fragment or variant, having one or more functional activities (e.g., biological activities) of albumin. In particular, "albumin" refers to human albumin or fragments thereof, especially the mature form of human albumin as shown in SEQ ID NO:6 herein or albumin from other vertebrates or fragments thereof, or analogs or variants of these molecules or fragments thereof.

According to certain embodiments of present disclosure the alternative term "FP" is used to identify the HLEP, in particular to define albumin as HLEP.

In particular, the proposed polypeptides of the invention may include naturally occurring polymorphic variants of human albumin and fragments of human albumin. Generally speaking, an albumin fragment or variant will be at least 10, preferably at least 40, most preferably more than 70 amino acids long.

Preferred embodiments of the invention include albumin variants used as a HLEP of the polypeptide of the invention with enhanced binding to the FcRn receptor. Such albumin variants may lead to a longer plasma half-life of a truncated VWF albumin variant fusion protein as compared to a truncated VWF fusion with a wild-type albumin.

The albumin portion of the polypeptides of the invention may comprise at least one subdomain or domain of HA or conservative modifications thereof.

Immunoglobulins as HLEPs

Immunoglobulin G (IgG) constant regions (Fc) are known in the art to increase the half-life of therapeutic proteins (Dumont J A et al. 2006. BioDrugs 20:151-160). The IgG constant region of the heavy chain consists of 3 domains (CH1-CH3) and a hinge region. The immunoglobulin sequence may be derived from any mammal, or from subclasses IgG1, IgG2, IgG3 or IgG4, respectively. IgG and IgG fragments without an antigen-binding domain may also be used as HLEPs. The therapeutic polypeptide portion is connected to the IgG or the IgG fragments preferably via the hinge region of the antibody or a peptidic linker, which may even be cleavable. Several patents and patent applications describe the fusion of therapeutic proteins to immunoglobulin constant regions to enhance the therapeutic proteins' in vivo half-lives. US 2004/0087778 and WO 2005/001025 describe fusion proteins of Fc domains or at least portions of immunoglobulin constant regions with biologically active peptides that increase the half-life of the peptide, which otherwise would be quickly eliminated in vivo. Fc-IFN-β fusion proteins were described that achieved enhanced biological activity, prolonged circulating half-life and greater solubility (WO 2006/000448 A2). Fc-EPO proteins with a prolonged serum half-life and increased in vivo potency were disclosed (WO 2005/063808 A1) as well as Fc fusions with G-CSF (WO 2003/076567 A2), glucagon-like peptide-1 (WO 2005/000892 A2), clotting factors (WO 2004/101740 A2) and interleukin-10 (U.S. Pat. No. 6,403,077), all with half-life enhancing properties.

Various HLEPs which can be used in accordance with this invention are described in detail in WO 2013/120939 A1.

N-Glycans and Sialylation of the Polypeptide of the Invention

The polypeptide of the invention preferably comprises N-glycans, and at least 75%, preferably at least 85%, more preferably at least 90% of said N-glycans comprise, on average, at least one sialic acid moiety. In preferred embodiments, at least 91%, at least 92%, at least 93%, at least 94%, at least 95%, at least 96%, at least 97%, at least 98%, or at least 99%, of said N-glycans comprise, on average, at least one sialic acid moiety. The inventors found that polypeptides comprising highly sialylated VWF fragments not only may have a further prolonged half-life themselves, but may also be capable to extend the half-life of co-administered FVIII further. In other words, administration of the polypeptide of the invention leads to an extended half-life and/or to a reduced clearance of co-administered FVIII.

The polypeptide of the invention preferably comprises N-glycans, and at least 50% of the sialyl groups of the N-glycans of the glycoproteins are α-2,6-linked sialyl groups. In general, terminal sialyl groups can be attached to the galactose groups via a α-2,3- or via a α-2,6-linkage.

Typically, N-glycans of the polypeptide of the invention comprise more α-2,6-linked sialyl groups than α-2,3-linked sialyl groups. Preferably, at least 60%, or at least 70%, or at least 80%, or at least 90% of the sialyl groups of the N-glycans are α-2,6-linked sialyl groups. These embodiments can be obtained by, e.g., co-expressing human α-2,6-sialyltransferase in mammalian cells.

Suitable methods of producing such glycoproteins are described in pending PCT/EP2016/061440. Accordingly, a method of producing a glycoprotein comprising N-glycans with increased sialylation is described therein, which method comprises (i) providing cells comprising a nucleic acid encoding a polypeptide comprising a truncated von Willebrand Factor (VWF), and (ii) culturing said cells at a temperature of less than 36.0° C. In addition, a method of producing a dimer of a glycoprotein comprising a truncated von Willebrand Factor (VWF), or for increasing the dimerization of said glycoprotein is described, which method comprises (i) providing cells comprising a nucleic acid encoding the amino acid sequence of the glycoprotein, and (ii) culturing said cells at a temperature of less than 36.0° C. Further, a method of producing a glycoprotein comprising N-glycans with increased sialylation is described therein, which comprises (i) providing cells comprising a nucleic acid encoding a polypeptide comprising a truncated von Willebrand Factor (VWF) and a recombinant nucleic acid encoding an α-2,6-sialyltransferase, and (ii) culturing the cells under conditions that allow expression of the glycoprotein and of the α-2,6-sialyltransferase.

In one embodiment, at least 85%, at least 90%, at least 95%, at least 96%, at least 97%, at least 98%, or at least 99%, of the N-glycans of the polypeptide of the invention comprise at least one sialic acid group. In another embodiment, at least 90%, at least 95%, at least 96%, at least 97%, at least 98%, or at least 99%, of the N-glycans of the polypeptide of the invention comprise at least one sialic acid group.

In another embodiment, less than 15%, less than 12%, less than 10%, or less than 8%, or less than 6%, or less than 5%, or less than 4%, or less than 3%, or less than 2% or even less than 1% of the N-glycans of the polypeptide of the invention are asialo-N-glycans, i.e. they are N-glycans lacking a sialic acid group. In another embodiment, less than 15%, less than 12%, less than 10%, or less than 8%, or less than 6%, or less than 5%, or less than 4%, or less than 3%, or less than 2% or even less than 1% of the N-glycans of the polypeptide of the invention are asialo-N-glycans, i.e. they do not have a sialic acid group.

Other embodiments of the invention comprise a truncated von Willebrand Factor (VWF), wherein said truncated VWF is capable of binding to a Factor VIII (FVIII), and wherein said glycoprotein comprises N-glycans, wherein less than 35%, preferably less than 34%, preferably less than 33%, preferably less than 32%, preferably less than 31%, preferably less than 30%, preferably less than 29%, preferably less than 28%, preferably less than 27% preferably less than 26%, preferably less than 25%, preferably less than 24%, preferably less than 23%, preferably less than 22%, preferably less than 21%, preferably less than 20%, preferably less than 19%, preferably less than 18%, preferably less than 17%, preferably less than 16%, preferably less than 15%, preferably less than 14%, preferably less than 13%, preferably less than 12%, preferably less than 11%, preferably less than 10%, preferably less than 9%, preferably less than 8%, preferably less than 7%, preferably less than 6% and preferably less than 5% of said N-glycans comprise, on average, two or more terminal and non-sialylated galactose residues.

Still other embodiments of the invention comprise a truncated von Willebrand Factor (VWF), wherein said truncated VWF is capable of binding to a Factor VIII (FVIII), and wherein said truncated VWF comprises N-glycans, wherein less than 6%, preferably less than 5%, preferably less than 4%, preferably less than 3%, preferably less than 2%, and preferably less than 1% of said N-glycans comprise, on average, three or more terminal and non-sialylated galactose residues.

The above-described embodiments can be combined with each other. Any percentages of N-glycans mentioned above, or any indications of the degree of sialylation, are to be understood as average percentages or degrees, i.e. they refer to a population of molecules, not to a single molecule. It is clear that the glycosylation or sialylation of the individual glycoprotein molecules within a population of glycoproteins will show some heterogeneity.

Dimers

The polypeptides of this invention have a high proportion of dimers. The polypeptide of the invention is therefore preferably present as dimer. In one embodiment, at least 50%, or at least 60%, or at least 70%, or at least 80%, or at least 90%, or at least 95% or about 100% of the polypeptides are present as dimers. In another embodiment, the ratio dimer:monomer of the polypeptide of the invention is at least 1.5, preferably at least 2, more preferably at least 2.5 or at least 3. Most preferably all polypeptides of the invention are present as dimers. Further preferred is that the polypeptide of the invention does not comprise multimeric forms. The use of dimers is favorable, as the dimer has an improved affinity to Factor VIII as compared to the monomer. The dimer content and the ratio of dimer to monomer of the polypeptide of the invention can be determined as described in Example 2.

In one embodiment, the affinity of the polypeptide of the invention to Factor VIII is greater than that of human native VWF to the same Factor VIII molecule. The Factor VIII affinity of the polypeptide may refer to human native, either plasma-derived or recombinant, Factor VIII, in particular to a recombinant Factor VIII molecule having a truncated o deleted B-domain, preferably a Factor VIII molecule as characterized by SEQ ID NO:5.

It has been found that preparations of the polypeptide of this invention with a high proportion of dimers do have an increased affinity to Factor VIII. Such increased affinity to Factor VIII does lead to an enhanced stabilization of Factor VIII by the polypeptides of the present invention. Alternatively to or in combination with an increased dimer proportion also polypeptides in accordance with the invention with mutations within the Factor VIII binding domain which do increase the affinity to Factor VIII are preferred embodiments of the invention. Suitable mutations are disclosed, e.g., in WO 2013/120939 A1.

Preparation of the Polypeptide

The nucleic acid encoding the polypeptide of the invention can be prepared according to methods known in the art. Based on the cDNA sequence of pre-pro form of human native VWF (SEQ ID NO:3), recombinant DNA encoding the above-mentioned truncated VWF constructs or polypeptides of the invention can be designed and generated.

Even if the polypeptide which is secreted by the host cells does not comprise amino acids 1 to 763 of pre-pro form of human native VWF, it is preferred that the nucleic acid (e.g. the DNA) encoding the intracellular precursor of the polypeptide comprises a nucleotide sequence encoding an amino acid sequence having a sequence identity of at least 95%, at least 96%, at least 97%, at least 98%, or at least 99%, to amino acids 23 to 763 or preferably to amino acids 1 to 763 of SEQ ID NO:4. Most preferably, the nucleic acid (e.g. the DNA) encoding the intracellular precursor of the polypeptide comprises a nucleotide sequence encoding amino acids 23 to 763 of SEQ ID NO:4, or amino acids 1 to 763 of SEQ ID NO:4.

Constructs in which the DNA contains the entire open reading frame inserted in the correct orientation into an expression plasmid may be used for protein expression. Typical expression vectors contain promoters that direct the synthesis of large amounts of mRNA corresponding to the inserted nucleic acid in the plasmid-bearing cells. They may also include an origin of replication sequence allowing for their autonomous replication within the host organism, and sequences that increase the efficiency with which the synthesized mRNA is translated. Stable long-term vectors may be maintained as freely replicating entities by using regulatory elements of, for example, viruses (e.g., the OriP sequences from the Epstein Barr Virus genome). Cell lines may also be produced that have integrated the vector into the genomic DNA, and in this manner the gene product is produced on a continuous basis.

Typically, the cells to be provided are obtained by introducing the nucleic acid encoding a polypeptide of the invention into mammalian host cells.

Any host cell susceptible to cell culture, and to expression of glycoproteins, may be utilized in accordance with the present invention. In certain embodiments, a host cell is mammalian. Non-limiting examples of mammalian cells that may be used in accordance with the present invention include BALB/c mouse myeloma line (NSO/1, ECACC No: 85110503); human retinoblasts (PER.C6 (CruCell, Leiden, The Netherlands)); monkey kidney CV1 line transformed by SV40 (COS-7, ATCC CRL 1651); human embryonic kidney line (293 or 293 cells subcloned for growth in suspension culture, Graham et al., J. Gen Virol., 36:59, 1977); baby hamster kidney cells (BHK, ATCC CCL10); Chinese hamster ovary cells +/−DHFR (CHO, Urlaub and Chasin, Proc. Natl. Acad. Sci. USA, 77:4216, 1980); mouse sertoli cells (TM4, Mather, Biol. Reprod., 23:243 251, 1980); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (HepG2, HB 8065); mouse mammary tumor (MMT 060562, ATCC CCL51); TRI cells (Mather et al., Annals NY. Acad. Sci., 383:44-68, 1982); MRC 5 cells; PS4 cells; human amniocyte cells (CAP); and a human hepatoma line (Hep G2). Preferably, the cell line is a rodent cell line, especially a hamster cell line such as CHO or BHK.

Methods suitable for introducing nucleic acids sufficient to achieve expression of a glycoprotein of interest into mammalian host cells are known in the art. See, for example, Gething et al., Nature, 293:620-625, 1981; Mantei et al., Nature, 281:40-46, 1979; Levinson et al. EP 117,060; and EP 117,058. For mammalian cells, common methods of introducing genetic material into mammalian cells include the calcium phosphate precipitation method of Graham and van der Erb (Virology, 52:456-457, 1978) or the lipofectamine™ (Gibco BRL) Method of Hawley-Nelson (Focus 15:73, 1993). General aspects of mammalian cell host system transformations have been described by Axel in U.S. Pat. No. 4,399,216. For various techniques for introducing genetic material into mammalian cells, see Keown et al., Methods in Enzymology, 185:527-537, 1990, and Mansour et al., Nature, 336:348-352, 1988.

The cells are cultured under conditions that allow expression of the polypeptide. The polypeptide can be recovered and purified using methods that are known to the skilled artisan.

Maximal Concentration, Area Under the Time-Concentration Curve, Terminal Half-Life, MRT, Clearance and Bioavailability Another aspect of the invention is the use of a polypeptide comprising a truncated VWF as defined hereinabove for providing or increasing bioavailability of FVIII after extravascular administration. Additionally, an aspect of the invention is its use for increasing the $C_{max}$, AUC, terminal half-life and/or mean residence time (MRT) and/or reducing the clearance of Factor VIII as compared to a reference treatment being identical to said treatment, except that the recombinant polypeptide to be administered does not comprise a HLEM and/or except that the molar ratio of the recombinant polypeptide to be administered to the FVIII to be administered is below a molar ratio according to the invention, in particular below a molar ratio of 50, below 60, below 75, below 100, below 200, below 300, below 400 or below 1000.

For evaluation of the pharmacokinetic data a two-compartment model (biphasic pharmacokinetic profile) was applied.

The maximal concentration ($C_{max}$) is the highest plasma concentration given by the model. Following co-administration of said recombinant polypeptide with FVIII the maximal concentration ($C_{max}$) for FVIII may be at least 10 IU/mL, at least 25 mIU/mL, at least 50 mIU/mL, at least 100 mIU/mL, at least 200 mIU/mL, at least 300 mIU/mL or at least 400 mIU/mL FVIII activity, preferably chromogenic FVIII activity.

Following co-administration of the recombinant polypeptide with FVIII the maximal concentration ($C_{max}$) for the recombinant polypeptide is according to certain embodiments at least 20 nmol/kg, at least 40 nmol/kg, at least 60 nmol/kg, at least 80 nmol/kg or at least 160 nmol/kg. Preferably, following co-administration of said recombinant polypeptide with FVIII the maximal concentration ($C_{max}$) for the recombinant polypeptide is at least 5 μg HLEM/mL, 10 μg HLEM/mL, at least 15 μg HLEM/mL, or at least 20 μg HLEM/mL, whereby the values are based on a calculation for the HLEM, preferably, the values are based on a quantitation using a HLEM specific assay such as an immunoassay, preferably specific for human albumin. The maximal concentration ($C_{max}$) for the recombinant polypeptide may be at least 3 fold higher as compared to a reference treatment, wherein said reference treatment is identical to the treatment according to the invention, except that the recombinant polypeptide to be administered does not comprise a HLEM and/or except that the ratio of the recombinant polypeptide to be administered to the FVIII to be administered is below a molar ratio according to the invention.

The $AUC_{0-inf}$ is the area under the plasma concentration-time curve from zero to infinity. Following co-administration of the recombinant polypeptide with FVIII the area under the concentration over time curve from t=0 to t=∞ ($AUC_{0-inf}$) for the co-administered FVIII may be at least 1000 mIU*h/mL, at least 2000 mIU*h/mL, at least 3000 mIU*h/mL, at least 5000 mIU*h/mL, at least 10000 mIU*h/mL or at least 20000 mIU*h/mL FVIII activity, preferably chromogenic FVIII activity.

Following co-administration of the recombinant polypeptide with FVIII the area under the concentration over time curve from t=0 to t=∞ ($AUC_{0-inf}$) for the co-administered recombinant polypeptide is at least 2 nmol*h/mL, at least 3 nmol*h/mL, at least 4 nmol*h/mL, at least 20 nmol*h/mL, at least 40 nmol*h/mL or at least 80 nmol*h/mL. Preferably, following co-administration of the recombinant polypeptide with FVIII the area under the concentration over time curve from t=0 to t=∞ ($AUC_{0-inf}$) for the co-administered recombinant polypeptide may be at least 500 μg HLEM*h/mL, at least 750 μg HLEM*h/mL, at least 1000 μg HLEM*h/mL at least 5000 μg HLEM*h/mL, or at least 10000 μg HLEM*h/m, whereby the values are based on a calculation for the HLEM, preferably, the values are based on a quantitation using a HLEM specific assay such as an immunoassay, preferably specific for human albumin.

Following co-administration of the recombinant polypeptide with FVIII the area under the concentration over time curve from t=0 to t=∞ ($AUC_{0-inf}$) for the co-administered recombinant polypeptide may be at least 5, is at least 10 or is at least 15 fold higher as compared to a reference treatment, wherein said reference treatment is identical to a treatment according to the invention, except that the recombinant polypeptide to be administered does not comprise a HLEM and/or except that the ratio of the recombinant polypeptide to be administered to the FVIII to be administered is below a molar ratio according to the invention.

The "half-life" $T\frac{1}{2}(t)$ at a certain time t is the time it takes to halve the plasma concentration C(t) that is present at time t. The "terminal half-life" (in the latter text abbreviated as $t_{1/2}$) is the limit of $T\frac{1}{2}(t)$ when t tends to infinity. It is calculated by dividing the natural logarithm of 2 by the terminal elimination constant.

The terminal half-life of the administered FVIII may be increased by the co-administration of the recombinant polypeptide, preferably by a factor of at least 1.2, at least 1.5, at least 2, at least 2.5, or at least 3, as compared to a reference treatment, wherein said reference treatment is identical to the treatment according to the invention, except that the recombinant polypeptide to be administered does not comprise a HLEM and/or except that the ratio of the recombinant polypeptide to be administered to the FVIII to be administered is below a molar ratio according to the invention. Preferably, the terminal half-life of the co-administered FVIII is increased as compared to a reference treatment, wherein said reference treatment is identical to the treatment according to the invention, except that the recombinant polypeptide to be administered does not comprise a HLEM and/or except that the ratio of the recombinant polypeptide to be administered to the FVIII to be administered is below a molar ratio according to the invention.

The terminal half-life of the administered FVIII followed by co-administration of the recombinant polypeptide, may amount to at least 5 h, at least 6 h, at least 7 h, at least 9 h, at least 10 h or at least 15 h.

The plasma half-life of the polypeptide of the invention may be increased compared to that of endogenous VWF, wherein the plasma half-life of the polypeptide is preferably at least 100%, at least 200% or preferably at least 400% higher than that of the endogenous VWF.

The terminal half-life of the recombinant polypeptide followed by co-administration with FVIII, may amount to at least 10 h, at least, 15 h, at least 20 h, at least 25 h, at least 30 h or at least 35 h. The terminal half-life of the recombinant polypeptide may be increased as compared to a reference treatment, wherein said reference treatment is identical to the treatment according to the invention, except that the recombinant polypeptide to be administered does not comprise a HLEM and/or except that the ratio of the recombinant polypeptide to be administered to the FVIII to be administered is below a molar ratio according to the invention.

The term "MRT", as used herein, means the average time a drug molecule (e.g. the polypeptide of the invention or a FVIII) resides in the body. In a pharmacokinetic system with constant clearance MRT can be calculated as the area under the first moment curve ($AUMC_{0-inf}$) divided by the $AUC_{0-inf}$. The first moment curve is time multiplied by plasma concentration at that time. $AUMC_{0-inf}$ is calculated analog to $AUC_{0-inf}$.

The mean residence time (MRT) of the administered FVIII is increased by the co-administration of the recombinant polypeptide, preferably by a factor of at least 1.5, at least 2, at least 3, at least 4 or at least 5, as compared to a reference treatment, wherein said reference treatment is identical to the treatment according to the invention, except that the recombinant polypeptide to be administered does not comprise a HLEM and/or except that the ratio of the recombinant polypeptide to be administered to the FVIII to be administered is below a molar ratio according to the invention.

The MRT of the administered FVIII may amount to at least 10 h, preferably at least 15 h, at least 20 h or at least 25 h.

The MRT of the administered recombinant polypeptide may be increased, preferably by a factor of at least 1.5, at least 2 or at least 3, as compared to a reference treatment, wherein said reference treatment is identical to a treatment of the invention, except that the recombinant polypeptide to be administered does not comprise a HLEM and/or except that the ratio of the recombinant polypeptide to be administered to the FVIII to be administered is below a molar ratio according to the invention.

The term "clearance", as used herein, refers to the rate at which plasma is cleared of drug. Specifically, it is the current elimination rate of a drug divided by its current plasma concentration. In a pharmacokinetic system after a single intravenous administration the clearance can be calculated as the ratio of dose over the $AUC_{0-inf}$, provided the clearance is constant. The lower the clearance the longer it takes until the plasma is cleared of the drug.

Following co-administration of the recombinant polypeptide with FVIII the clearance (CL) value of the administered FVIII is reduced compared to a reference treatment, preferably by a factor of at least 1.5, at least 2, at least 3, at least 5, at least 7.5 or at least 10, wherein said reference treatment is identical to a treatment of the invention, except that the recombinant polypeptide to be administered does not comprise a HLEM and/or except that the ratio of the recombinant polypeptide to be administered to the FVIII to be administered is below a molar ratio according to the invention.

Preferably, following co-administration of the recombinant polypeptide with FVIII the clearance (CL) value of the administered FVIII is below 135 mUkg/h, below 80 mL/kg/h, below 45 mL/kg/h, below 40 mL/kg/h, below 35 mUkg/h, below 30 mUkg/h or below 25 mL/kg/h. The clearance (CL) value of the administered FVIII is preferably lower than that of a reference treatment, wherein said reference treatment is identical to the treatment, except that the recombinant polypeptide to be administered does not comprise a HLEM and/or except that the molar ratio of the recombinant polypeptide to be administered to the FVIII to be administered is below a molar ratio according to the invention.

Following co-administration of the recombinant polypeptide with FVIII the clearance (CL) value of the recombinant polypeptide may amount to a range between 1.0 to 2.5 mL/kg/h, or between 1.1 to 2.2 mL/kg/h or between 1.2 to 2.1 mUkg/h.

Following co-administration of said recombinant polypeptide with FVIII the clearance (CL) value for the recombinant polypeptide is reduced by a factor of at least 2, at least 5, or at least 10, as compared to a reference treatment, wherein said reference treatment is identical to the treatment according to the invention, except that the recombinant polypeptide to be administered does not comprise a HLEM and/or except that the molar ratio of the recombinant polypeptide to be administered to the FVIII to be administered is below a molar ratio according to the invention.

The term bioavailability, as used herein, is defined as the percentage of the $AUC_{0-inf}$ of the polypeptide of the invention, for example rD'D3-FP, after s.c. administration, in relation to the $AUC_{0-inf}$ of the polypeptide of the invention, for example rD'D3-FP, after i.v. administration.

The invention further relates to the use of a polypeptide as defined hereinabove, e.g. but not limited to embodiments [1] to [66] above, for enabling subcutaneous FVIII administration. The invention in particular further relates to the use of a polypeptide as defined hereinabove for providing or increasing the bioavailability of FVIII.

The bioavailability of the administered FVIII may be increased following co-administration with the recombinant polypeptide by a factor of at least 2, at least 3, at least, 4, at least 5 or at least 10, as compared to a reference treatment, wherein said reference treatment is identical to the treatment according to the invention, except that the recombinant polypeptide to be administered does not comprise a HLEM and/or except that the molar ratio of the recombinant polypeptide to be administered to the FVIII to be administered is below a molar ratio according to the invention.

The bioavailability of the administered FVIII following co-administration with the recombinant polypeptide is preferably at least 2%, at least 3%, at least 5%, preferably at least 7%, at least 10%, at least 15%, at least 30%, at least 35% or at least 40%. Further preferred ranges for bioavailability of the administered FVIII following co-administration with the recombinant polypeptide are 5-80%, 5-70%, 5-60%, 5-50%, 5-40%, 5-30%, 5-25%, 10-25%, 10-15%, or 5-15%.

The bioavailability of the recombinant polypeptide following co-administration with the FVIII is at least 30%, preferably at least 35%, more preferably at least 40%, at least 45%, at least 50%, at least 55%, at least 60%, at least 65%, at least 70% or at least 80%.

A further aspect of this invention is a method of treating a blood coagulation disorder, comprising administering to a patient in need thereof an effective amount of a polypeptide as defined hereinabove.

A further aspect is the use of a polypeptide as defined hereinabove, e.g. by any of but not limited to embodiments [1] to [66] above, for reducing the frequency of administration of FVIII in a treatment of hemophilia A. The frequency of subcutaneous administration of FVIII may be reduced to twice per week. Alternatively, the frequency of subcutaneous administration of FVIII may be reduced to once per week, or even lower, e.g. to once per 10 days or once per 14 days. The FVIII may be administered twice weekly, every 5 days, once weekly, every 10 days, every two weeks, every three weeks, every four weeks or once a month, or in any range between any two of the foregoing values, for example from every four days to every month, from every 10 days to every two weeks, etc.

The term "trough level" is used herein to define the plasma FVIII concentration at which in a prophylactic setting the next dose of FVIII would be applied. Currently, for patients with severe haemophilia A the recommended trough levels (i.e. the lowest level of coagulation factor present in the body) are set at 1%. Time to 1, 5 and 10% trough levels is calculated by setting the model equation equal to 0.01, 0.05 or 0.1 IU/mL and solving for time.

Preferably, the time period for reaching a 1%, 5% or 10% trough level of the FVIII co-administered together with the polypeptide having a HLEM is prolonged compared to a reference treatment, wherein said reference treatment is identical to the treatment according to the invention, except the FVIII is administered with a recombinant polypeptide without having said HLEM.

The time period either for reaching the 1% trough level of the FVIII co-administered together with the polypeptide is at least about 30 h, at least about 35 h, at least about 38 h, at least about 40 h, or at least about 50 h; or for reaching the 5% trough level of the FVIII co-administered together with said polypeptide is at least about 20 h, at least about 22 h, at least about 29 h, at least about 34 h, or at least about 43 h; or for reaching the 10% trough level of the FVIII co-administered together with said polypeptide is at least about 5 h, at least about 6 h, at least about 10 h, at least about 18 h, or at least about 20 h.

Treatment of Coagulation Disorder

The polypeptides of the invention are useful for treating coagulation disorders including hemophilia A and von-Willebrand disease. The term "hemophilia A" refers to a deficiency in functional coagulation FVIII, which is usually inherited. The von-Willebrand disease according to some preferred embodiments is selected from the group consisting of von-Willebrand disease type 2N, von-Willebrand disease type 3 and von-Willebrand disease type 1.

In one embodiment, the blood coagulation disorder is moderate hemophilia A. Moderate hemophilia A is preferably characterized by an endogenous FVIII activity level which is from about 1% to about 5% of the endogenous FVIII activity level in NHP. Typically, subjects having moderate hemophilia A have an endogenous FVIII activity level from 0.01 to 0.05 IU/mL in plasma.

In another embodiment, the blood coagulation disorder is mild hemophilia A. Mild hemophilia A is preferably characterized by an endogenous FVIII activity level which is from about 5% to about 40% of the endogenous FVIII activity level in NHP. Typically, subjects having mild hemophilia A have an endogenous FVIII activity level from 0.05 to 0.4 IU/mL in plasma.

In another embodiment, the blood coagulation disorder is severe hemophilia A, preferably associated with an endogenous FVIII activity level that is below 1% of the endogenous FVIII activity level in NHP.

In another embodiment, the blood coagulation disorder is von-Willebrand disease type 2N. von-Willebrand disease type 2N is preferably characterized by an endogenous FVIII activity level which is from about 3 IU/dL to about 30 IU/dL FVIII activity level corresponding to 3% to about 30% of the endogenous FVIII activity level in NHP. Most of the patients have an endogenous FVIII activity level below 20 IU/dL, thus a level below 20% of the endogenous FVIII activity level in NHP. Thus, subjects having von-Willebrand disease type 2N have an endogenous FVIII activity level from 0.03 IU/mL to 0.3 IU/mL in plasma, typically below 0.2 IU/mL.

In another embodiment, the blood coagulation disorder is von-Willebrand disease type 3, preferably characterized by an endogenous FVIII activity level before treatment which is usually in a range between about 1 IU/dL and about 20 IU/dL FVIII activity level, corresponding to about 1% to about 20% of the endogenous FVIII activity level in NHP. Most of the patients have an endogenous FVIII activity level below 10 IU/dL, thus a level below 10% of the endogenous FVIII activity level in NHP.

According to another embodiment, the blood coagulation disorder is von-Willebrand disease type 1, characterized by an endogenous FVIII activity level before treatment which is reduced compared to the endogenous FVIII activity level in NHP.

Treatment of a disease encompasses the treatment of patients already diagnosed as having any form of the disease at any clinical stage or manifestation; the delay of the onset or evolution or aggravation or deterioration of the symptoms or signs of the disease; and/or preventing and/or reducing the severity of the disease.

A "subject" or "patient" to whom a polypeptide of the invention is administered preferably is a human. In certain aspects, the human is a pediatric patient. In other aspects, the human is an adult patient.

Compositions comprising a polypeptide of the invention and, optionally FVIII, are described herein. The compositions typically are supplied as part of a sterile, pharmaceutical composition that includes a pharmaceutically acceptable carrier. This composition can be in any suitable form (depending upon the desired method of administering it to a patient).

The term "Factor VIII" and "FVIII" or "Factor VIII protein" are used interchangeably herein and encompass both plasma derived FVIII and recombinant FVIII. Recombinant FVIII encompasses without limitation full-length FVIII as well as two-chain B-domain deleted or truncated variants as well as single-chain B-domain deleted or truncated variants for example those described in WO 2004/067566 A1 and other FVIII variants with mutations outside the B-domain but having the biological activity of FVIII.

The polypeptide of the invention can be administered to a patient by a variety of extravascular routes such as subcutaneously, intradermally or intramuscularly. The most suitable route for administration in any given case will depend on the particular polypeptide, the subject, and the nature and severity of the disease and the physical condition of the subject. Preferably, a polypeptide of the invention will be administered subcutaneously.

The polypeptide and the FVIII are preferably co-administered subcutaneously.

Determination of the total number of doses and length of treatment with a polypeptide of the invention and FVIII is well within the capabilities of those skilled in the art. The dosage of the polypeptide of the invention as well as FVIII to be administered depends on the concentrations of the FVIII to be administered, the concentration of endogenous VWF in the patient to be treated, or both. An effective dosage based on the ratios defined by the inventors of this application can be determined by the skilled person, taking into account the molecular weight of the polypeptide of the invention as well as the molecular weight of the FVIII to be administered. The degree of severity of the blood coagulation disorder may also be considered to determine the appropriate dosage of the polypeptide of the invention as well as of FVIII to be administered. Typical dosages for FVIII may range from about 20 UI/kg body weight to about 1000 UI/kg body weight, preferably from about 20 UI/kg body weight to about 500 UI/kg body weight, further preferred from about 20 UI/kg body weight to about 400 UI/kg body weight, more preferred from about 20 UI/kg body weight to about 300 UI/kg body weight.

In accordance with this invention, the patient being treated with the polypeptide of the invention is also treated with blood coagulation Factor VIII. The polypeptide of the invention and the Factor VIII may preferably be administered simultaneously, i.e. together, although an administration in a sequential fashion could in principle also be performed, both modes of administration being encompassed by the term "combination therapy" and "co-administration". The polypeptide of the invention and the Factor VIII may be administered as a mixture, i.e. within the same composition, or separately, i.e. as separate compositions. Co-administration of the recombinant polypeptide and the FVIII protein is preferably achieved by administration together in a single composition comprising the recombinant polypeptide and the FVIII protein. According to further preferred embodiments, co-administration of the recombinant polypeptide and the FVIII protein is achieved by providing a combination product comprising the recombinant polypeptide and the FVIII blended in a single composition or by providing a set or kit of at least two separate products arranged to be mixed before administration, whereby a first product comprises the recombinant polypeptide and a second product comprises the FVIII.

In particular, in case that the recombinant polypeptide and the FVIII protein are provided in separate compositions or products to be mixed prior to co-administration, the mixture may be treated before administration in such a manner to allow prior to administration for at least a proportion of said recombinant polypeptide to bind to said FVIII. For example, the mixture could be incubated for a certain time. Such incubation could be conducted in less than 1 min, or less than 5 min at either ambient temperature or, if appropriate, at elevated temperature, however, preferably at a temperature below 40° C. Such a quick incubation step may also be appropriate during reconstitution for a combination product comprising the recombinant polypeptide and the FVIII blended in a single composition.

The concentration of Factor VIII in the composition used is typically in the range of 10-10,000 IU/mL. In different embodiments, the concentration of FVIII in the compositions of the invention is in the range of 10-8,000 IU/mL, or 10-5,000 IU/mL, or 20-3,000 IU/mL, or 50-1,500 IU/mL, or 3,000 IU/mL, or 2,500 IU/mL, or 2,000 IU/mL, or 1,500 IU/mL, or 1,200 IU/mL, or 1,000 IU/mL, or 800 IU/mL, or 750 IU/mL, or 600 IU/mL, or 500 IU/mL, or 400 IU/mL, or 300 IU/mL, or 250 IU/mL, or 200 IU/mL, or 150 IU/mL, or 125 IU/mL, or 100 IU/mL, or 62.5 IU/mL, or 50 IU/mL, provided the requirements regarding the ratio with respect to the VWF polypeptide of the invention as defined herein are fulfilled.

"International Unit," or "IU," is a unit of measurement of the blood coagulation activity (potency) of FVIII as measured by a FVIII activity assay such as a one stage clotting assay or a chromogenic substrate FVIII activity assay using a standard calibrated in "IU" against an international standard preparation. One stage clotting assays are known to the art, such as that described in N Lee, Martin L, et al., An Effect of Predilution on Potency Assays of FVIII Concentrates, Thrombosis Research (Pergamon Press Ltd.) 30, 511 519 (1983). Principle of the one stage assay: The test is executed as a modified version of the activated Partial Thromboplastin Time (aPTT)-assay: Incubation of plasma with phospholipids and a surface activator leads to the activation of factors of the intrinsic coagulation system. Addition of calcium ions triggers the coagulation cascade. The time to formation of a measurable fibrin clot is determined. The assay is executed in the presence of Factor VIII deficient plasma. The coagulation capability of the deficient plasma is restored by Coagulation Factor VIII included in the sample to be tested. The shortening of coagulation time is proportional to the amount of Factor VIII present in the sample. The activity of Coagulation Factor VIII is quantified by direct comparison to a standard preparation with a known activity of Factor VIII in International Units.

Another standard assay is a chromogenic substrate assay. Chromogenic substrate assays may be purchased commercially, such as the Coamatic® FVIII test kit (Chromogenix-Instrumentation Laboratory SpA V. le Monza 338-20128 Milano, Italy). Principle of the chromogenic assay: In the presence of calcium and phospholipid, Factor X is activated by Factor IXa to Factor Xa. This reaction is stimulated by Factor VIIIa as cofactor. FVIIIa is formed by low amounts of thrombin in the reaction mixture from FVIII in the sample to be measured. When using the optimum concentrations of Ca2+, phospholipid and Factor IXa and an excess quantity of Factor X, activation of Factor X is proportional to the potency of Factor VIII. Activated Factor X releases the chromophore pNA from the chromogenic substrate S-2765. The release of pNA, measured at 405 nm, is therefore proportional to the amount of FXa formed, and, therefore, also to the Factor VIII activity of the sample.

Pharmaceutical Compositions

Therapeutic formulations of the polypeptide of the invention suitable in the methods described herein can be prepared for storage as lyophilized formulations or aqueous solutions by mixing the polypeptide having the desired degree of purity with optional pharmaceutically-acceptable carriers, excipients or stabilizers typically employed in the art (all of which are referred to herein as "carriers"), i.e., buffering agents, stabilizing agents, preservatives, isotonifiers, non-ionic detergents, antioxidants, and other miscellaneous additives. See, Remington's Pharmaceutical Sciences, 16th edition (Osol, ed. 1980). Such additives must be nontoxic to the recipients at the dosages and concentrations employed.

Buffering agents help to maintain the pH in the range which approximates physiological conditions. They can present at concentration ranging from about 2 mM to about 50 mM. Suitable buffering agents include both organic and inorganic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium gluconate mixture, etc.), oxalate buffer (e.g., oxalic acid-sodium oxalate mixture, oxalic acid-sodium hydroxide mixture, oxalic acid-potassium oxalate mixture, etc), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additionally, phosphate buffers, histidine buffers and trimethylamine salts such as Tris can be used.

Preservatives can be added to retard microbial growth, and can be added in amounts ranging from 0.2%-1% (w/v).

Suitable preservatives include phenol, benzyl alcohol, metacresol, methyl paraben, propyl paraben, octadecyldimethylbenzyl ammonium chloride, benzalconium halides (e.g., chloride, bromide, and iodide), hexamethonium chloride, and alkyl parabens such as methyl or propyl paraben, catechol, resorcinol, cyclohexanol, and 3-pentanol. Isotonicifiers sometimes known as "stabilizers" can be added to ensure isotonicity of liquid compositions and include polhydric sugar alcohols, preferably trihydric or higher sugar alcohols, such as glycerin, erythritol, arabitol, xylitol, sorbitol and mannitol. Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, α-monothioglycerol and sodium thio sulfate; low molecular weight polypeptides (e.g., peptides of 10 residues or fewer); proteins such as human serum albumin, bovine serum albumin, gelatin or immunoglobulins; hydrophylic polymers, such as polyvinylpyrrolidone monosaccharides, such as xylose, mannose, fructose, glucose; disaccharides such as lactose, maltose, sucrose and trisaccacharides such as raffinose; and polysaccharides such as dextran. Stabilizers can be present in the range from 0.1 to 10,000 weights per part of weight active protein.

Non-ionic surfactants or detergents (also known as "wetting agents") can be added to help solubilize the therapeutic agent as well as to protect the therapeutic protein against agitation-induced aggregation, which also permits the formulation to be exposed to shear surface stressed without causing denaturation of the protein. Suitable non-ionic surfactants include polysorbates (20, 80, etc.), polyoxamers (184, 188 etc.), Pluronic polyols, polyoxyethylene sorbitan monoethers (TWEEN®-20, TWEEN®-80, etc.). Non-ionic surfactants can be present in a range of about 0.05 mg/ml to about 1.0 mg/ml, or in a range of about 0.07 mg/ml to about 0.2 mg/ml.

Additional miscellaneous excipients include bulking agents (e.g., starch), chelating agents (e.g., EDTA), antioxidants (e.g., ascorbic acid, methionine, vitamin E), and cosolvents.

The formulation herein can also contain a second therapeutic agent in addition to a polypeptide of the invention. Examples of suitable second therapeutic agents are provided below.

The dosing schedule can vary from once a month to daily depending on a number of clinical factors, including the type of disease, severity of disease, and the patients sensitivity to the polypeptide of the invention. In specific embodiments, a polypeptide of the invention is administered, twice weekly, every 5 days, once weekly, every 10 days, every two weeks, every three weeks, every four weeks or once a month, or in any range between any two of the foregoing values, for example from every four weeks to every month, from every 10 days to every two weeks, etc.

The dosage of a polypeptide of the invention to be administered will vary according to the particular polypeptide, the subject, and the nature and severity of the disease, the physical condition of the subject, the therapeutic regimen (e.g., whether a second therapeutic agent is used), and the selected route of administration; the appropriate dosage can be readily determined by a person skilled in the art.

It will be recognized by one of skill in the art that the optimal quantity and spacing of individual dosages of a polypeptide of the invention will be determined by the nature and extent of the condition being treated, the form, route and site of administration, and the age and condition of the particular subject being treated, and that a physician will ultimately determine appropriate dosages to be used. This dosage can be repeated as often as appropriate. If side effects develop the amount and/or frequency of the dosage can be altered or reduced, in accordance with normal clinical practice.

The pharmaceutical composition is preferably formulated to be administered extravascularly, preferably to be administered subcutaneously.

Those skilled in the art will appreciate that the invention described herein is susceptible to variations and modifications other than those specifically described. It is to be understood that the invention includes all such variations and modifications which fall within the spirit and scope. The invention also includes all of the features, compositions, steps, and compounds referred to or indicated in this specification, individually or collectively and any and all combinations of any two or more of said features, compositions, steps, and compounds.

The nucleotide and amino acid sequences shown in the sequence listing are summarized in the Table 1.

TABLE 1

| SEQ ID NO: | Remarks |
|---|---|
| 1 | DNA sequence encoding a polypeptide comprising acids 1 to 1242 of human VWF, a glycine/serine linker and human albumin; nucleotide positions (nt): nt 1-6: EcoRI restriction enzyme cleavage site nt 32-3757: coding sequence for VWF amino acids 1 to 1242 nt 3758-3850: coding sequence for glycine/serine linker nt 3851-5608: coding sequence for human albumin nt 5609-5616: NotI restriction enzyme cleavage site |
| 2 | Amino acid sequence encoded by SEQ ID NO :1 (mature form): amino acid positions (aa): aa 1-479: VWF D'D3 region (VWF amino acids 764-1242) aa 480-510: glycine/serine linker aa 511-1095: human albumin |
| 3 | DNA sequence encoding the pre-pro form of human native VWF |
| 4 | Amino acid sequence encoded by SEQ ID NO: 3 |

TABLE 1-continued

| SEQ ID NO: | Remarks |
|---|---|
| 5 | Amino acid sequence of a single chain Factor VIII molecule |
| 6 | Amino acid sequence of mature human serum albumin |
| 7 | Amino acid sequence of D'D3-His<br>aa 1-479: VWF D'D3 region (VWF amino acids 764-1242)<br>aa 480-511: glycine/serine linker<br>aa 512-519: polyhistidine tag |
| 8 | Amino acid sequence of D'D3-CTP<br>aa 1-479: VWF D'D3 region (VWF amino acids 764-1242)<br>aa 480-511: glycine/serine linker<br>aa 512-576: C-terminal peptide of human chorionic gonadotropin-β subunit<br>aa 577-584: polyhistidine tag |

Certain embodiments of the invention will now be described with reference to the following examples which are intended for the purpose of illustration only and are not intended to limit the scope of the generality hereinbefore described.

EXAMPLES

Material and Methods
Generation of D'D3 Albumin Fusion Protein (D'D3-FP):

The expression cassette for D'D3-FP consisting of cDNA encoding VWF amino acids 1 to 1242, a glycine/serine linker and the cDNA of human albumin was prepared by custom gene synthesis (Eurofins Genomics, Ebersberg, Germany). Through flanking restriction sites (EcoRI, NotI) the expression cassette was excised from the cloning vector supplied and inserted into a pIRESneo3 vector (BD Biosciences, Franklin Lakes, N.J., USA) linearized with EcoRI and NotI. The resulting expression plasmid contained nucleotide sequences encoding the VWF propeptide, D' and D3 (VWF amino acids 1 to 1242 of SEQ ID NO:4) fused to the albumin coding sequence through a short linker coding sequence under CMV promoter control. The nucleotide sequence of the coding sequence is displayed as SEQ ID NO:1, the amino acid sequence of the mature D'D3-FP is shown as SEQ ID NO:2. The presence of the D1 D2 VWF propeptide (741 amino acids) during expression is crucial for dimerization of the synthesized polypeptide.

A similar approach was used to generate an expression plasmid for a His-tagged D'D3 protein (D'D3 and His8 linked by a glycine/serine linker) and a D'D3 fusion protein to the C-terminal peptide of human chorionic gonadotropin-β subunit, also linked via a glycine/serine linker and tagged by 8 histidines at the C-terminus of the fusion protein. The amino acid sequence of the mature D'D3-His is shown as SEQ ID NO: 7 and the amino acid sequence of the mature D'D3-CTP is shown as SEQ ID NO: 8.

The expression plasmids as described above were grown up in XL10 Gold (Agilent Technologies) and purified using standard protocols (Qiagen, Hilden, Germany).

CHO K1 cells were transfected using the Lipofectamine 2000 reagent (Invitrogen) and grown up in serum-free medium (CD-CHO, Invitrogen) in the presence of 500-1000 µg/ml Geneticin. An expression plasmid encoding PACE/furin (pFu-797) as described in WO 2007/144173 A1 was cotransfected to maximize propeptide cleavage efficacy. Single cell derived clones were grown up and selected according to their D'D3-FP expression yield as quantified by an albumin specific enzyme immunoassay (see below). The cell line finally selected for D'D3-FP fermentation was called T2050-CL3.

Production of D'D3-FP was carried out in bioreactors applying a fermentation process in perfusion mode. The fermentation process for the production of D'D3-containing polypeptides started with the thaw of cell line T2050-CL3 followed by cell expansion in shake flasks and finally a fermentation process in perfusion mode using the Sartorius BioStat B-DCU 5 L bioreactor and the BioStat STR 50 L single-use bioreactors. The BioSeps 10 L or 200 L (Applikon), respectively, were used as cell retention devices. Cell culture media were either PowerCHO3 (Lonza BESP1204) with 8 mM L-glutamine and 1 µM $CuSO_4$ or ProCHO5 (Lonza BESP1072) with 10 mM L-glutamine and 1 µM $CuSO_4$.

The seed trains in shake flasks were performed at 37° C., 7.5% $CO_2$ at a shaker speed of 160 rpm.

The 5 L bioreactor was inoculated with a target VCD of $2.5 \times 10^5$ cells/mL. The cells were cultivated in PowerCHO3 with 8 mM L-glutamine and 1 µM $CuSO_4$ at a temperature of +37.0° C., a pH of 7.00, and at 30% oxygen saturation. A temperature shift to +34.0° C. (evaluated range +31° C. to +35° C.) was performed after initial harvests from the bioreactor run at +37° C. had been taken. The pH was controlled using $CO_2$ sparged as acid and $NaHCO_3$ as base. The overlay air flow rate was set to 0.5 L/min. A ring sparger was used as a sparging unit. The agitation rate was 150 rpm with a 2 fold pitch blade impeller in down pull mode.

The 50 L bioreactor was inoculated with a target VCD of $3.0 \times 10^5$ cells/mL. The cells were cultivated in ProCHO5 medium with 10 mM L-glutamine and 1 µM $CuSO_4$ at a temperature of +37.0° C., a pH of 6.90, and at 30% oxygen saturation. A temperature shift to +34.0° C. was performed after the initial one or two harvests. PH control as above, the overlay air flow rate was set to 2 L/min. A micro sparger was used as a sparging unit. The agitation rate was 90 rpm with a 2 fold pitch blade impeller in down pull mode.

The perfusion was initiated when the VCD in the bioreactor was $1.0 \times 10^6$ cells/mL. The perfusion rate was set to 1.0 volume/volume/day. The BioSep was operated in back flush mode with 5 (10) minutes runtime and 10 seconds back flush at a power input of 7 (30) W (numbers in brackets refer to the 50 L bioreactor). The perfusate and the bleed were filtered inline and collected in bags over 48 hours at +2 to +8° C. The VCD was controlled by active bleeding using a turbidity probe using glucose consumption as parameter with a target of 2 g/L glucose. Harvest and bleed were filtered inline, the harvest system consisting of a disposable filter and disposable bag was changed every second day.

To prepare material for the PK analyses described below D'D3 albumin fusion protein harvests were purified by affinity and size exclusion chromatography. Briefly, the cell-free harvest from the bioreactor was concentrated 30-fold using a TFF system (e.g. Pall Centramate 500 S) with a 30 kD membrane (e.g Pall Centramate OS030T12). That concentrate was spiked with NaCl and EDTA to a final concentration of 0.75 M NaCl and 5 mM EDTA and loaded overnight on a CaptureSelect Human Albumin column (Life Technologies) which was pre-equilibrated with 20 mM Tris buffer pH 7.4. After washing the column with equilibration buffer D'D3-FP was eluted with elution buffer (20 mM Tris, 2 M $MgCl_2$, pH 7.4). The eluate was then 10-fold concentrated and dialyzed against 50 mM Tris, 150 mM NaCl, pH 7.4 using Ultra Centrifugal Filters with a 30 kD cut-off (e.g. Amicon. UFC903024). To separate the D'D3-FP dimer from the monomer portion that material was loaded on a Superdex 200 pg column (GE Healthcare Code: 17-1069-01) pre-equilibrated with 50 mM Tris, 150 mM NaCl, pH 7.4 and the peak fractions containing the D'D3-FP dimer were pooled. The area under the curve for the dimer and monomer peak fractions was used to calculate dimer to monomer ratio. Dimer preparations of said D'D3 albumin fusion protein were used for the pharmacokinetic experiments. Such dimer preparations are referred to as D'D3-FP in the following, if not indicated otherwise.

The rD'D3-FP EYA variant has been generated by equivalent method steps.

His-tagged D'D3 proteins were purified by Ni-chelate affinity and size exclusion chromatography. Briefly, TFF concentrated cell-free bioreactor harvest (see above for details) was loaded on a preequilibrated (20 mM sodium phosphate/500 mM NaCl, pH 7.4) Ni-Sepharose column (HisTrap™, GE Healthcare) over night. After washing the column with 20 mM sodium phosphate/500 mM NaCl/30 mM Imidazol, pH 7.4 the protein was eluted with 20 mM sodium phosphate+500 mM NaCl+500 mM Imidazol, pH 7.4. The eluate was then concentrated and dialysed (TBS, pH7.4) using an Amicon Ultra Centrifugal Filter (see above). The final product was then loaded onto a SEC column (see above), the peak fractions containing the dimer were pooled and concentrated to about 7 mg/mL $OD_{280-320}$. Dimer preparations of His-tagged D'D3 proteins were used for the pharmacokinetic experiments. Such dimer preparations are referred to as rD'D3-His in the following, if not indicated otherwise.

Example 1: Subcutaneous Bioavailability of a Recombinant FVIII in the Presence of rD'D3-FP or Variants Thereof To assess, whether extravascular injections might be an option for an improved therapy with FVIII, a typical representative for an extravascular therapy, i.e. subcutaneous (s.c.) injection, was chosen. We aimed at characterizing the impact of a recombinant polypeptide comprising a truncated VWF on the subcutaneous bioavailability of FVIII in different approaches:

Example 1.1: Investigation of rD'D3-FP and rVIII-SingleChain given both subcutaneously in a hemophilia A model, i.e. in FVIII ko mice.

Example 1.2: Investigation of rD'D3-FP and rVIII-SingleChain given both subcutaneously in a model with physiological endogenous FVIII, i.e. in pigs.

Example 1.3: Investigation of the effect of rD'D3-FP on different FVIII products, each given subcutaneously in a hemophilia A model, i.e. in FVIII ko mice.

Example 1.4: Investigation of the effect of a rD'D3-FP affinity variant, a rD'D3 molecule with non-albumin HELP and rVIII-SingleChain given both subcutaneously in a mouse hemophilia A model, i.e. in FVIII ko mice.

Therefore, we investigated the impact of a recombinant polypeptide comprising the D' and D3 domains of VWF fused to albumin via a linker peptide when subcutaneously co-administered with a recombinant FVIII.

For the Examples, a polypeptide comprising a truncated VWF having an amino acid sequence as defined in SEQ ID NO:2 was used. This particular fusion protein consists of an N-terminal amino acid sequence from 1-479 representing the VWF D'D3 region (amino acids 764-1242 of human native VWF), followed by a 31 amino acid glycine/serine linker peptide and a C-terminal human albumin amino acid sequence from 511-1095. This fusion protein having a sequence as defined in SEQ ID NO:2 is referred to as rD'D3-FP or rD'D3-FP WT in the following.

For the purpose of the examples, a recombinant B-Domain-deleted single chain FVIII, i.e. rVIII-SingleChain, having an amino acid sequence as defined in SEQ ID NO:5 was used. In Example 1.3 different recombinant FVIII products have been tested.

Further, we investigated the impact of different ratios of rD'D3-FP to the rVIII-SingleChain.

The impact of the albumin fusion as a potential mediator for subcutaneous availability was investigated by comparing bioavailability of rD'D3-FP to that of a His-tagged rD'D3 (rD'D3-His). The amino acid sequence of the mature D'D3-His is shown as SEQ ID NO: 7 whereby D'D3 and His8 are being joined by a glycine/serine linker.

As an alternative for the albumin as half-life extending polypeptide (HLEP), in some Examples a rD'D3-FP variant is used having instead of albumin a CTP (C-terminal peptide of human chorionic gonadotropin-β subunit) fused to rD'D3 via a glycine/serine linker which is referred to as rD'D3-CTP hereinafter. The fusion protein rD'D3-CTP has a sequence as defined in SEQ ID NO:8.

In certain Examples a high affinity variant of rD'D3-FP was used. This particular variant fusion protein consists of an N-terminal amino acid sequence from 1-479 representing the VWF D'D3 region (amino acids 764-1242 of human native VWF), followed by a 31 amino acid glycine/serine linker peptide and a C-terminal human albumin amino acid sequence from 511-1095, provided that within the D'D3 domain of said polypeptide three amino acid substitutions are present, i.e. S764E, S766Y and V1083A. This fusion protein consists of a sequence as defined in SEQ ID NO:2 having said three substitutions S764E, S766Y, and V1083A within the D'D3 region. Said variant is referred to as rD'D3-FP EYA hereinafter.

Material and Methods

Background Information

For calculating ratios of the different rDD3-FP:rVIII-SingleChain combinations, the following assumptions were made:

The drugs are diluted in 40 mL plasma per kg body weight after their administration Molecular weight of the polypeptide of the invention used: rD'D3-FP molecular weight of monomeric subunit (including glycosylation): 127,000 Da (HLEM=human albumin); the monomeric weight was used in the calculated ratios Molecular weight of rD'D3-His: rD'D3-His molecular weight of monomeric subunit (including glycosylation): 64,000 Da; the monomeric weight was used in the calculated ratios Molecular weight of rD'D3-FP EYA variant: rD'D3-FP molecular weight of monomeric subunit (including glycosylation): 127,000 Da; the monomeric weight was used in the calculated ratios Molecular weight of rD'D3-CTP: rD'D3-CTP molecular weight of monomeric subunit (including glycosylation): 69,800 Da; the monomeric weight was used in the calculated ratios Molecular weight of FVIII used: rVIII-SingleChain molecular weight (with glycosylation): 180,000 Da and specific activity: 11,000 UI/mg Molecular weight of other FVIII products used:
- Beriate®: molecular weight: 285,000 Da and specific activity: 5,000 IU/mg
- Advate®: molecular weight: 280,000 Da and specific activity: 7,000 IU/mg
- ReFacto AF®: molecular weight: 170,000 Da and specific activity: 10,700 UI/mg Beriate® is a plasma-derived human FVIII product from CSL Behring.

Advate® was purchased from Baxter AG, Vienna, Austria and is a recombinant full-length factor VIII preparation.

ReFacto AF® was purchased from Pfizer Limited, Kent, United Kingdom and is a recombinant factor VIII preparation having a deleted B-domain.

Analytics rD'D3-FP (wildtype as well as the EYA variant) was applied at dose levels quantified by a human albumin ELISA, thereby measuring the albumin part of the protein. This rD'D3-FP ELISA was used for plasma samples as well.

The human albumin ELISA used a polyclonal goat anti-human albumin capture antibody from Bethyl Laboratories, Inc. (Montgomery, USA). The detection solution consists of a polyclonal peroxidase labelled anti-human albumin detection antibody preparation (Bethyl Laboratories Inc., Montgomery, USA). A chromogenic readout, i.e. TMB from Siemens Healthcare (Eschborn, Germany) was used for quantification in a microplate reader at 450/650 nm (ELx808, BioTek, USA) directly after stopping. As a standard, the drug formulation containing rD'D3-FP was used. rD'D3-FP amounts are given in mg albumin, i.e. no adjustment was done for the D'D3 part of the molecule.

The dose levels of the rD'D3-His and rD'D3-CTP construct were measured at $OD_{280}$, and the protein amount was adjusted to an equimolar concentration to the rD'D3-FP amount for rD'D3-His. Thereby, the unit for rD'D3-His is the same as for rD'D3-FP, i.e. it is plotted in the graphs as theoretical mg albumin. rD'D3-CTP was dosed in a similar molar ratio as rD'D3-FP (EYA variant) and the unit is not transferred to albumin but given as rD'D3-CTP. The plasma samples of the PK containing rD'D3-His and rD'D3-CTP were measured in an anti-D'D3 ELISA. This D'D3 ELISA used a monoclonal anti-human D'D3 capture antibody (in house research preparation). The detection solution consists of another monoclonal peroxidase labelled anti-human D'D3 detection antibody (in house research preparation). A chromogenic readout, i.e. TMB from Siemens Healthcare (Eschborn, Germany) was used for quantification in a microplate reader at 450/650 nm (ELx808, BioTek, Vermont, USA) directly after stopping. As a standard, the drug formulation containing rD'D3-His and rD'D3-CTP was used, and as before for rD'D3-His calculated to an equimolar concentration as compared to rD'D3-FP, i.e. again amounts are given as theoretical mg albumin. rD'D3-CTP amounts are given as rD'D3-CTP concentrations.

FVIII chromogenic activity plasma levels were detected by the COAMATIC® FVIII assay (FVIII:C chromogenic assay, Chromogenix, Instrumentation Laboratory SpA, Milan, Italy) according to the test instruction manual of the manufacturer. FVIII chromogenic activity is abbreviated as FVIII:C.

Human FVIII:Ag plasma levels were determined with the FVIII Asserachrom ELISA test kit from Stago, S.A.S., France according to the test instruction manual. The Asserachrom testkit contained all reagents with exception of the stop solution, which was obtained from Siemens Healthcare (Eschborn, Germany). As a standard, the drug formulation containing rVIII-SingleChain was used.

Animals

FVIII Ko Mice

FVIII knock-out (ko) mice (representing a hemophilia A phenotype) were chosen, since they lack exons 16 and 17 of the FVIII gene, and thus have no plasma factor VIII activity (Bi L. et al, Nature genetics, 1995, Vol 10(1), 119-121; Bi L. et al, Blood, 1996, Vol 88(9), 3446-3450). This allows the analysis of FVIII activity levels following treatment with FVIII by quantification of FVIII activity in the plasma of these mice.

Male and female FVIII ko mice in a weight range of 17-35 g were breed at Charles River Laboratories (Sulzfeld, Germany). In house, the animals were kept at standard housing conditions, i.e. at 20-24° C. under a 12 h/12 h light-darkness cycle. Animals were fed ad libitum with standard rat diet (Ssniff-Versuchsdiäten, Soest, Germany). Tap water was supplied ad libitum. Animal husbandry and study procedures complied with the German Animal Welfare law and European Union regulations.

The group size was n=12, divided in 3 or 4 cohorts. Thus, n=3-4 animals per time-point were used.

Pigs

Pigs were chosen, since they represent a good model for subcutaneous bioavailability with respect to its predictivity for men.

Male pigs in a weight range of 23-27 kg were breed at Schlosser (Schwalmtal, Germany). In house, the animals were kept in a stable on straw at 18-21° C. Animals were fed with bruised grain. Tap water was supplied ad libitum. Animal husbandry and study procedures complied with the German Animal Welfare law and European Union regulations.

The group size was 2 (intravenous) or 3 (subcutaneous).

Example 1.1: Investigation of rD'D3-FP and rVIII-SingleChain Given Both Subcutaneously in a Hemophilia a Model, i.e. in FVIII Ko Mice Experimental Details The test articles were administered s.c. in the neck or i.v. into the lateral tail vein by a single injection, at a total volume of 5 mL/kg. Administered dose levels and routes are given in Table 2.

TABLE 2

Treatment groups

| rD'D3-FP or rD'D3-His [mg albumin/kg] | rVIII-SingleChain [IU FVIII:C/kg] | Route and duration of observation | Ratio rD'D3-FP:FFVIII |
|---|---|---|---|
| — | 400 | sc (72h) | — |
| 10 | 400 | sc (72h) | 745 |
| 3 | 400 | sc (96h) | 223 |
| 3 | 200 | sc (96h) | 447 |
| 3 | 100 | sc (96h) | 894 |

TABLE 2-continued

| Treatment groups | | | |
|---|---|---|---|
| rD'D3-FP or rD'D3-His [mg albumin/kg] | rVIII-SingleChain [IU FVIII:C/kg] | Route and duration of observation | Ratio rD'D3-FP:FFVIII |
| 3 | 100 | iv (96h) | 894 |
| 3 | 50 | sc (96h) | 1787 |
| 3 | — | sc (96h) | — |
| 3 | — | iv (96h) | — |
| 1 | 400 | sc (96h) | 74 |
| 1 | 100 | sc (96h) | 298 |
| 1 | 100 | iv (96h) | 298 |
| 1 | 50 | sc (96h) | 596 |
| 0.3 | 200 | sc (96h) | 45 |
| 3 (rD'D3-His) | 200 | sc (96h) | 447 |
| 3 (rD'D3-His) | 200 | iv (96h) | 447 | rD'D3-FP was applied in a dose range from 0.3 to 10 mg/kg based on human albumin values, rVIII-SingleChain doses ranged from 50 to 400 IU/kg chromogenic FVIII activity. rVIII-SingleChain was reconstituted with water for injection, and rD'D3-FP as well as rD'D3-His was thawed in a water bath. For co-administration, the compounds were incubated together for approximately 30 minutes at +37° C. In every case, a dose volume of 5 mL/kg was administered, with dilution buffer for FVIII being used for dissolution of the compounds if necessary.

Blood samples were taken retrobulbary under short term anaesthesia using an alternating sampling scheme. Timepoints in the s.c. groups were 3, 8, 16, 24, 48, 72, and 96 h p.a. (except for the 400 UI/kg rVIII-SingleChain and the 10 mg/kg rD'D3-FP+400 IU/kg rVIII-SingleChain group), and in the i.v. groups 5 min, 3, 8, 24, 48, 72, and 96 h p.a. The PK profile was taken from 3 or 4 cohorts of mice per group, and n=3-4 animals per timepoint. Blood samples were anticoagulated using sodium citrate (1 parts sodium citrate 3.13%+9 parts blood), processed to plasma and stored at −70° C. for the determination of FVIII activity, FVIII antigen, albumin and/or rD'D3-His.

rD'D3-FP exposure was determined by measurement of the albumin part of the construct using a human albumin ELISA. Further, FVIII chromogenic activity and in selected groups FVIII antigen was measured.

Biostatistics

Estimation of the maximal concentration ($C_{max}$), the area under the concentration over time curve from t=0 to t=∞ ($AUC_{0-inf}$), mean residence time (MRT), clearance (CL) and terminal half-life ($t_{1/2}$) was done by two-compartmental modelling in the i.v. calculations, and by two-compartmental-resorption modelling in the s.c. calculations. For parameter estimation, a weighted least-squares cost function was applied. Bioavailability was calculated as the percentage of the $AUC_{0-inf}$ after s.c. administration as compared to i.v. administration. Time to 1, 5 and 10% trough levels was calculated by setting the model equation equal to 0.01, 0.05 or 0.1 IU/mL and solving for time.

Results

Evaluation of D'D3 Data

Both constructs of D'D3 (rD'D3-FP and rD'D3-His, with and without albumin fusion, respectively) were absorbed after s.c. administration. rD'D3-FP could be quantified over the whole period of observation of 96 h, even at the lowest dose of 0.3 mg/kg; i.e. it remained above the detection limit of 23.4 ng/mL (FIG. 1). However, rD'D3-FP could be detected at a significantly higher levels compared to rD'D3-His, in particular at the later time points.

It needs to be mentioned that some of the curves showed high similarity in the last two measurement points, which led to a "flattening out" of the plasma concentration curve in the terminal phase. Thereby estimation of clearance, MRT, $t_{1/2}$ and $AUC_{0-inf}$ was estimated extremely long when including the last point. A second calculation was done without the last timepoint in order to avoid an overestimation of bioavailability; a comparison of the data is given in Table 3 and shows good agreement of the data without the last timepoint with the other data.

Therefore, in the tables and graphs (except for FIG. 1), the second dataset without the 96 h datapoint was used, which may underestimate bioavailability of rD'D3-FP.

Figure 2:
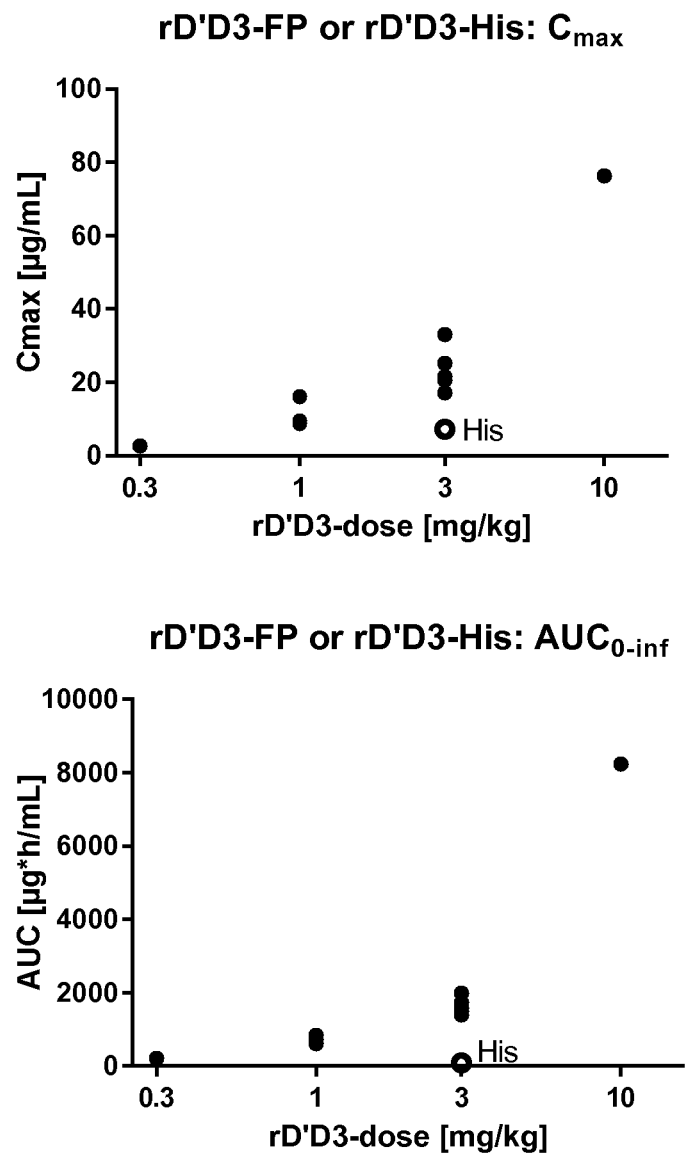
FIG. 2 shows maximal concentration and AUC of the recombinant polypeptide plasma levels after subcutaneous administration of rD'D3-FP or rD'D3-His with or without recombinant FVIII in FVIII ko mice. rD'D3-FP was quantified via its albumin component, and rD'D3-His data are calculated to equimolar concentrations. Data is given as mean±SD for n=1-4 mice per timepoint. Estimation of $C_{max}$ and $AUC_{0-inf}$ was done by two-compartmental-resorption modelling.

$C_{max}$ and $AUC_{0-inf}$ showed dose-dependency in the tested range of 0.3-10 mg/kg rD'D3-FP and 0-400 UI/kg rVIII-SingleChain, independent of the added rFVIII (Table 3, FIG. 2). Related to the lower exposure, both, $C_{max}$ as well as $AUC_{0-inf}$ of rD'D3-His, were relevantly lower than that for comparable rD'D3-FP doses. In detail, for s.c. administration, $C_{max}$ was >3-fold and $AUC_{0-inf}$ was >16-fold lower.

Clearance, MRT and $t_{1/2}$ did not show a dose dependency for rD'D3-FP. The high variability in the s.c. estimates is prone to the difficulties with fitting the correct curves for the flat exposure over time curves. Clearance values were in the range of 1.2-2.1 mL/kg/h after s.c., and slightly lower (0.8-0.9 mL/kg/h) after i.v. administration. In line with this the MRT ($t_{112}$) range was 41-117 h (15-90 h) for s.c. and 55-83 h (39-69 h) for i.v. administration. In contrast, elimination of rD'D3-His was much quicker, i.e. clearance was 34.8 mUkg/h after s.c. and 11.8 mL/kg/h after i.v. administration (>13 fold difference), MRT was 11 h after s.c. and 5 h after i.v. administration (>3 fold difference) and $t_{1/2}$ was 7 h after s.c. and 6 h after i.v. administration (>2 fold difference).

Figure 3:
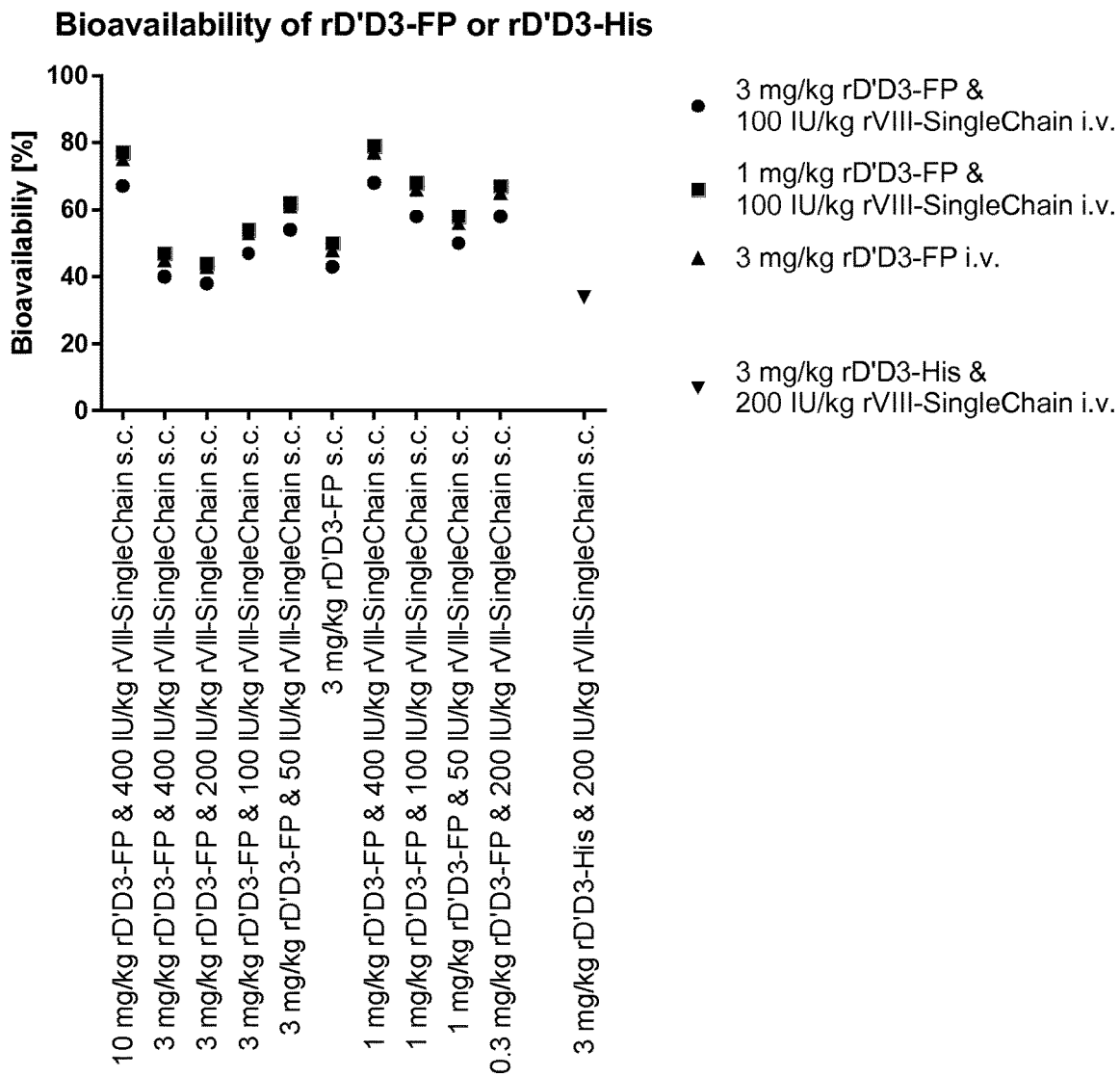
FIG. 3 shows bioavailability of rD'D3-FP or rD'D3-His after subcutaneous administration of rD'D3-FP or rD'D3-His with or without recombinant FVIII in FVIII ko mice. rD'D3-FP was quantified via its albumin component, and rD'D3-His data are calculated to equimolar concentrations. Data was calculated from the mean $AUC_{0-inf}$ calculated from n=1-4 mice per timepoint. Estimation of $AUC_{0-inf}$ was done by two-compartmental-resorption modelling. Bioavailability was calculated as the percentage of the $AUC_{0-inf}$ after s.c. administration as compared to i.v. administration, in case of rD'D3-FP for the three different i.v. groups using rD'D3-FP at different doses with or without rFVIII.

Importantly, bioavailability of rD'D3-FP after subcutaneous administration ranges from 40-79%, again with quite a high variability of the different groups within the experiment (Table 4, FIG. 3). Nevertheless, this bioavailability is independent of the rVIII-SingleChain or rD'D3-FP dose used in this experiment. rD'D3-His showed a lower bioavailability of 34%.

TABLE 3

Pharmacokinetic parameters of rD'D3-FP or rD'D3-His after s.c. or i.v. administration of rD'D3-FP or rD'D3-His and rVIII-SingleChain in FVIII ko mice

| Treatment | $C_{max}$, extrap. [μg/mL] | Clearance Albumin [mL/kg/h] | MRT [h] | Half-life, terminal [h] | $AUC_{0-inf}$ [μg * h/mL] |
|---|---|---|---|---|---|
| 3 mg/kg rD'D3-FP s.c. | 21.5 | 1.9 | 65 | 42 | 1590 |
| 10 mg/kg rD'D3-FP & 400 IU/kg rVIII-SingleChain s.c. | 76.3 | 1.2 | 98 | 63 | 8234 |
| 3 mg/kg rD'D3-FP & 400 IU/kg rVIII-SingleChain s.c. | 17.1 | 2.0 | 78 | 46 | 1492 |
| 3 mg/kg rD'D3-FP & 200 IU/kg rVIII-SingleChain s.c. | (24.6)* 25.2 | (0.0)* 2.1 | (99726) 41 | (69193)* 15 | (734488)* 1398 |
| 3 mg/kg rD'D3-FP & 100 IU/kg rVIII-SingleChain s.c. | 20.6 | 1.7 | 71 | 44 | 1739 |

TABLE 3-continued

Pharmacokinetic parameters of rD'D3-FP or rD'D3-His after s.c. or i.v. administration of rD'D3-FP or rD'D3-His and rVIII-SingleChain in FVIII ko mice

| Treatment | $C_{max}$, extrap. [µg/mL] | Clearance Albumin [mL/kg/h] | MRT [h] | Half-life, terminal [h] | $AUC_{0-inf}$ [µg * h/mL] |
|---|---|---|---|---|---|
| 3 mg/kg rD'D3-FP & 50 IU/kg rVIII-SingleChain s.c. | (33.3)* 33.0 | (0.0)* 1.5 | (99835)* 49 | (69273)* 29 | (919779)* 1989 |
| 1 mg/kg rD'D3-FP & 400 IU/kg rVIII-SingleChain s.c. | 16.1 | 1.2 | 117 | 90 | 844 |
| 1 mg/kg rD'D3-FP & 100 IU/kg rVIII-SingleChain s.c. | 8.8 | 1.4 | 73 | 48 | 719 |
| 1 mg/kg rD'D3-FP & 50 IU/kg rVIII-SingleChain s.c. | (9.6)* 9.5 | (0.0)* 1.6 | (81484)* 55 | (56588)* 34 | (177600) 613 |
| 0.3 mg/kg rD'D3-FP & 200 IU/kg rVIII-SingleChain s.c. | 2.6 | 1.4 | 77 | 52 | 215 |
| 3 mg/kg rD'D3-His & 200 IU/kg rVIII-SingleChain s.c. | 7.2 | 34.8 | 11 | 7 | 86 |
| 3 mg/kg rD'D3-FP i.v. | 90.0 | 0.9 | 48 | 34 | 3286 |
| 3 mg/kg rD'D3-FP & 100 IU/kg rVIII-SingleChain i.v. | 71.0 | 0.8 | 83 | 69 | 3702 |
| 1 mg/kg rD'D3-FP & 100 IU/kg rVIII-SingleChain i.v. | 27.1 | 0.9 | 55 | 39 | 1064 |
| 3 mg/kg rD'D3-His & 200 IU/kg rVIII-SingleChain i.v. | 81.6 | 11.7 | 5 | 6 | 257 |

*High similarity in the last two measurement points leads to an artificial "flattening out" of the plasma concentration curve in the terminal phase; thereby estimation of clearance, MRT, $t_{1/2}$ and $AUC_{0-inf}$ was estimated extremely long when including the last point. Therefore, an additional calculation was done without the last timepoint in order to avoid an overestimation of bioavailability.

TABLE 4

Bioavailability of rD'D3-FP or rD'D3-His after s.c. administration in FVIII ko mice calculated against i.v. reference treatments

| S.c. treatment | Bioavailability [%] to i.v. reference treatments[§] | | | |
|---|---|---|---|---|
| | 3 mg/kg rD'D3-FP & 100 IU/kg rVIII-SingleChain i.v. | 1 mg/kg rD'D3-FP & 100 IU/kg rVIII-SingleChain i.v. | 3 mg/kg rD'D3-FP i.v. | 3 mg/kg rD'D3-His & 200 IU/kg rVIII-SingleChain i.v. |
| 3 mg/kg rD'D3-FP s.c. | 43 | 50 | 48 | n.a. |
| 10 mg/kg rD'D3-FP & 400 IU/kg rVIII-SingleChain s.c. | 67 | 77 | 75 | n.a. |
| 3 mg/kg rD'D3-FP & 400 IU/kg rVIII-SingleChain s.c. | 40 | 47 | 45 | n.a. |
| 3 mg/kg rD'D3-FP & 200 IU/kg rVIII-SingleChain s.c. | 38* | 44* | 43* | n.a. |
| 3 mg/kg rD'D3-FP & 100 IU/kg rVIII-SingleChain s.c. | 47 | 54 | 53 | 1.a. |
| 3 mg/kg rD'D3-FP & 50 IU/kg rVIII-SingleChain s.c. | 54* | 62* | 61* | n.a. |
| 1 mg/kg rD'D3-FP & 400 IU/kg rVIII-SingleChain s.c. | 68 | 79 | 77 | n.a. |
| 1 mg/kg rD'D3-FP & 100 IU/kg rVIII-SingleChain s.c. | 58 | 68 | 66 | n.a. |
| 1 mg/kg rD'D3-FP & 50 IU/kg rVIII-SingleChain s.c. | 50* | 58* | 56* | n.a. |
| 0.3 mg/kg rD'D3-FP & 200 IU/kg rVIII-SingleChain s.c. | 58 | 67 | 65 | n.a. |
| 3 mg/kg rD'D3-His & 200 IU/kg rVIII-SingleChain s.c. | n.a. | n.a. | n.a. | 34 | n.a.—not applicable;
*lower confidence in AUC estimate of s.c. data (see above)
[§]reference group with same treatment is given in bold Evaluation of FVIII Data rVIII-SingleChain administered without any polypeptide of the invention, i.e. without any D'D3-FP construct, was not relevantly absorbed when administered s.c., at least no FVIII activity above the detection limit could be measured. Surprisingly however, FVIII was absorbed when co-administered s.c. with either of the two D'D3 constructs (rD'D3-FP and rD'D3-His, with and without albumin fusion, respectively); and FVIII activity endured the absorption process (FIG. 3).

It needs to be mentioned that also for FVIII activity one curve showed high similarity in the last two measurement points, which led to a "flattening out" of the plasma concentration curve in the terminal phase. Thereby estimation of clearance, MRT, $t_{1/2}$ and $AUC_{0-inf}$ was estimated extremely long when including the last point. A second calculation was done without the last timepoint in order to avoid an overestimation of bioavailability; a comparison of the data is given in Table 5. Therefore, in the tables and graphs (except for FIG. 4), the second dataset without the last datapoint was used, which may underestimate bioavailability of rD'D3-His.

Figure 4:
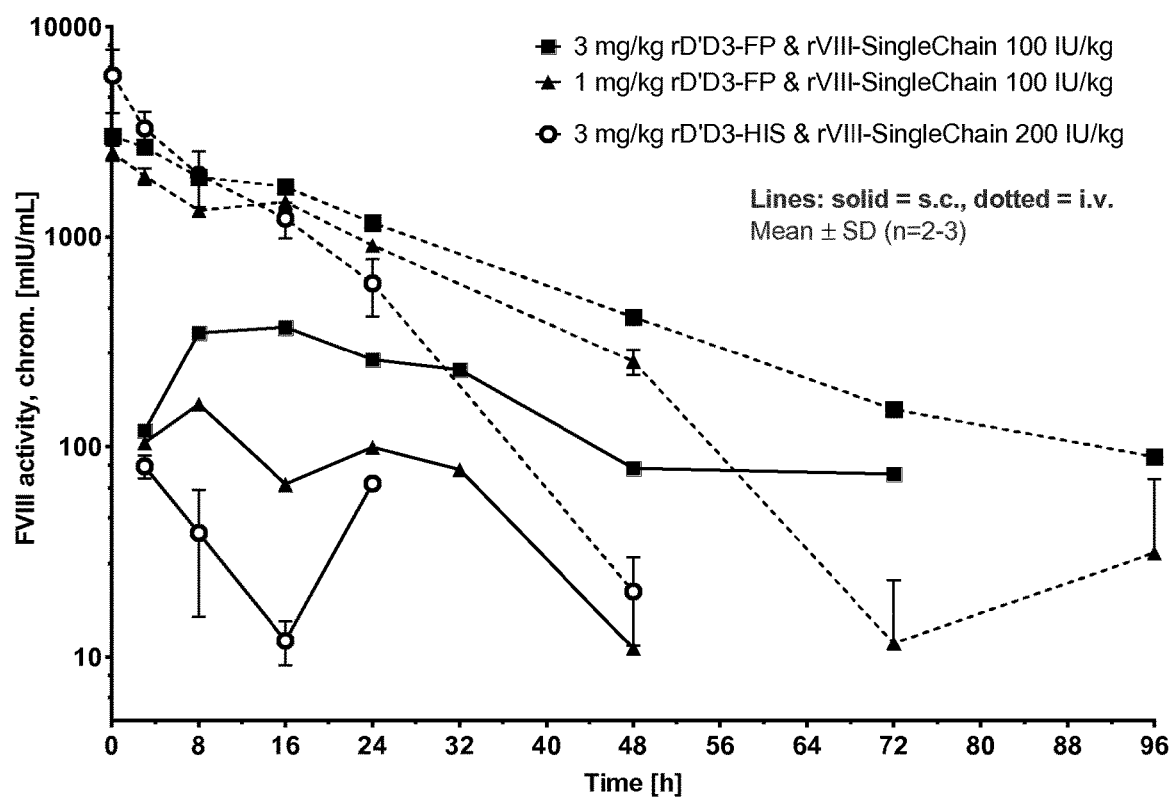
FIG. 4 shows FVIII activity plasma levels after subcutaneous or intravenous administration of rD'D3-FP or rD'D3-His with or without recombinant FVIII in FVIII ko mice. FVIII was quantified as chromogenic FVIII activity. Data is given as mean±SD for n=2-3 mice per timepoint. Solid lines represent s.c. and dotted lines i.v. treatment; Abbreviation: s.c.: subcutaneous; i.v.: intravenous.

Dependent on the FVIII dose, FVIII activity was quantified for at least 32 h (1 mg/kg rD'D3-FP & 50 IU/kg rVIII-SingleChain) and up to the last timepoint of 96 h (e.g. any dose with 400 IU/kg rVIII-SingleChain and 1-10 mg/kg rD'D3-FP); i.e. it remained over the detection limit of 3 or 10 mIU/mL (FIG. 4). As example, FIG. 4 represents FVIII plasma exposure after s.c. or i.v. administration of 1 or 3 mg/kg rD'D3-FP with 100 IU/kg rVIII-SingleChain compared with 3 mg/kg rD'D3-His with 200 IU/kg rVIII-SingleChain (the higher dose was administered to be able to monitor exposure). When no D'D3 construct was administered, rVIII-SingleChain remained below the detection limit, even at a s.c. dose of 400 IU/kg (data not shown).

Figure 5:
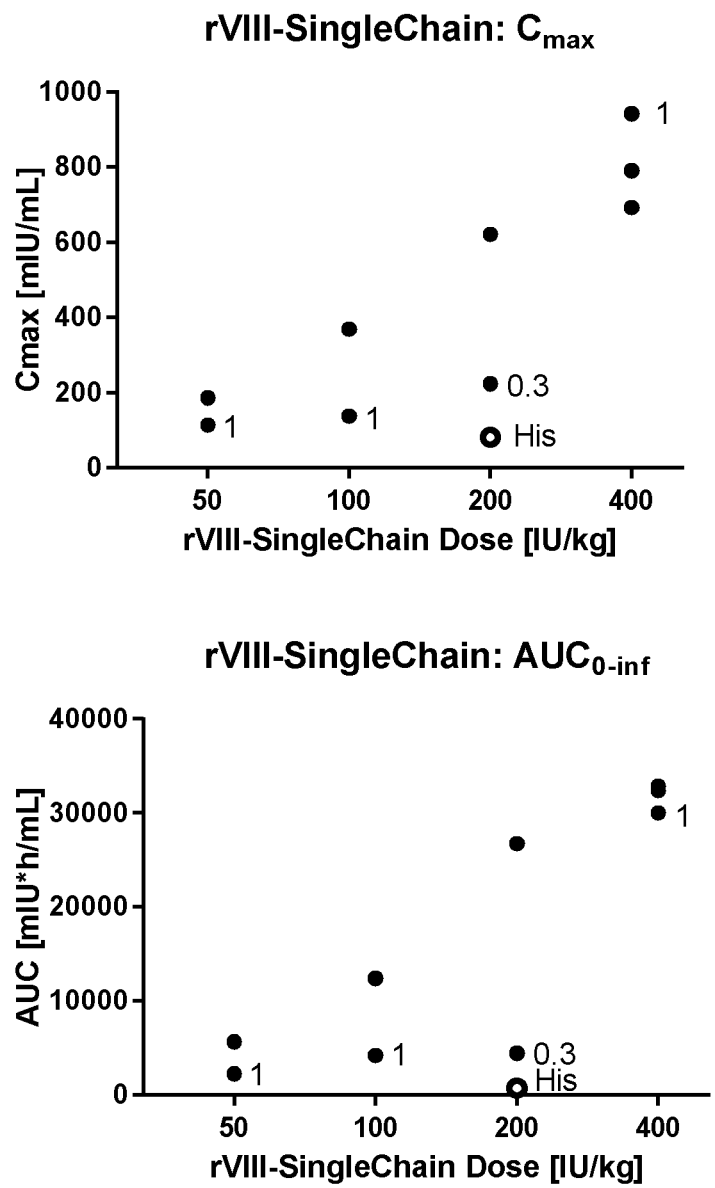
FIG. 5 shows maximal concentration and AUC of FVIII activity plasma levels after subcutaneous administration of rD'D3-FP or rD'D3-His with or without recombinant FVIII in FVIII ko mice. FVIII was quantified as chromogenic FVIII activity. Data is given as mean±SD for n=2-3 mice per timepoint. Estimation of $C_{max}$ and $AUC_{0-inf}$ was done by two-compartmental-resorption modelling.

$C_{max}$ and $AUC_{0-inf}$ showed dose-dependency in the tested range of 0.3-10 mg/kg rD'D3-FP and 0-400 IU/kg rVIII-SingleChain, independent of the coadministered rD'D3-FP, while exposure was much lower when rD'D3-His was given (Table 5, FIG. 5).

When rD'D3-FP and rVIII-SingleChain were given at a molar ratio >50, CL for rVIII-SingleChain ranged from 7.5-23.7 mL/kg/h, and was thus lower than that for 0.3 mg/kg rD'D3-FP & 200 IU/kg rVIII-SingleChain s.c. (ratio 45) or rD'D3-His co-administration. In line with this, MRT and $t_{1/2}$ for rVIII-SingleChain were higher for rD'D3-FP and rVIII-SingleChain given at a ratio >50 as compared to rD'D3-His, except for the very low dose of rVIII-SingleChain of 50 IU/kg (range MRT: 24-37 h, range $t_{1/2}$: 8-20 h). For comparison, rVIII-SingleChain administered i.v. without rD'D3-FP was shown to have a CL of ~2-3 mL/kg/h, a MRT of 18 h and a $t_{1/2}$ of 15 h in FVIII ko mice, and a CL of ~2-3 mL/kg/h, a MRT of ~20 h and a $t_{1/2}$ of ~14 h in man (data not presented herein). Thus, pharmacokinetic parameters after s.c. administration were variable, but roughly comparable to those after i.v. administration.

Figure 6:
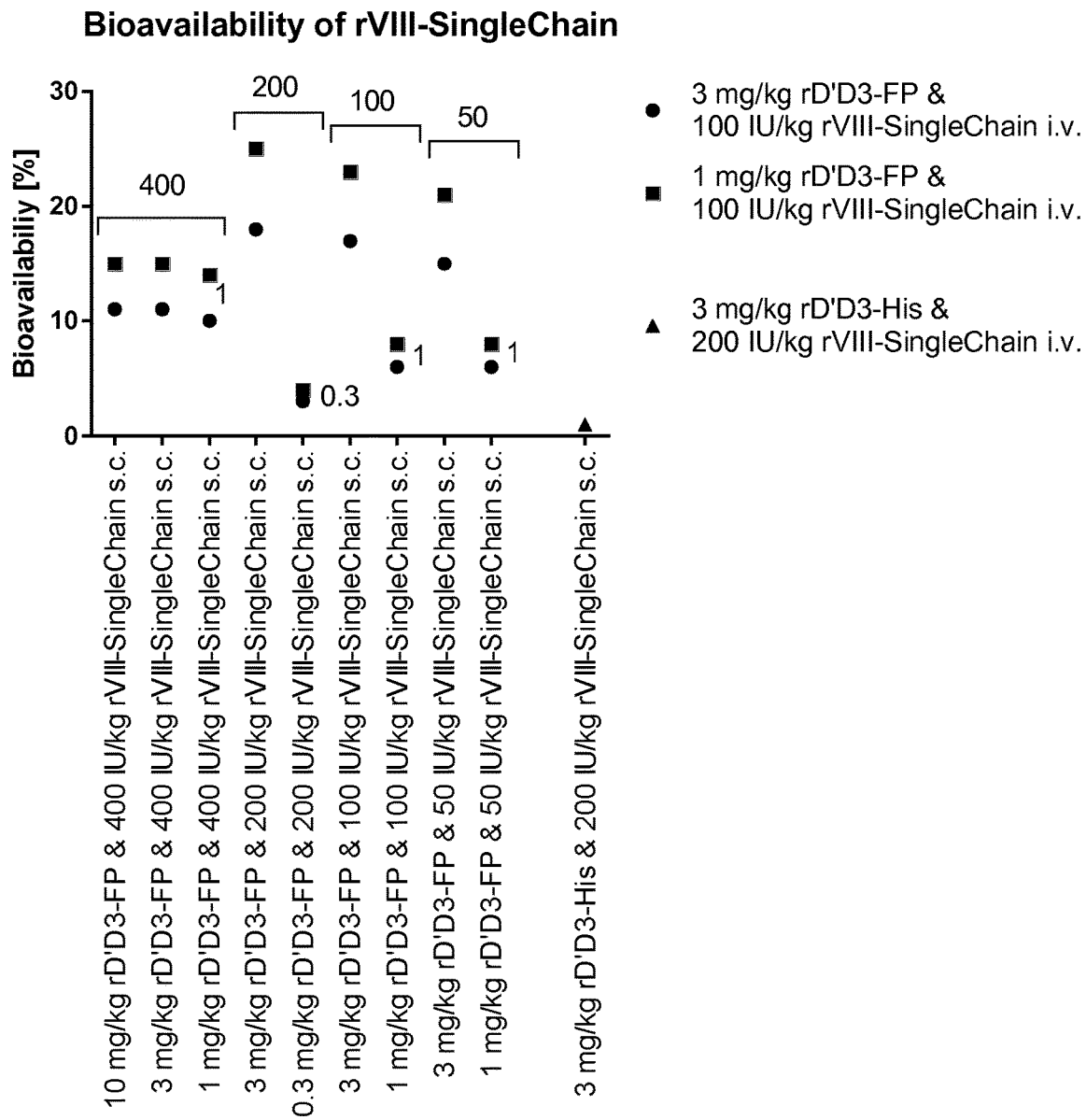
FIG. 6 shows bioavailability of chromogenic FVIII activity after subcutaneous administration of rD'D3-FP or rD'D3-His with recombinant FVIII in FVIII ko mice. Data was calculated from the mean $AUC_{0-inf}$ calculated from n=2-3 mice per timepoint. Estimation of $AUC_{0-inf}$ was done by two-compartmental-resorption modelling. Bioavailability was calculated as the percentage of the $AUC_{0-inf}$ after s.c. administration as compared to i.v. administration, in case of rD'D3-FP for the two different i.v. groups using rD'D3-FP at different doses with or without rFVIII. FVIII doses and selected rD'D3-FP doses are given as numbers in the graph.

Taken together, bioavailability of rVIII-SingleChain ranged from 11-25%, when given at a dose ≥3 mg/kg rD'D3-FP, between 6-14% when given at a dose of 1 mg/kg rD'D3-FP and ≤4% at a dose of 0.3 mg/kg rD'D3-FP (Table 6, FIG. 6). This bioavailability is dependent on the dose of rVIII-SingleChain in that sense that a potential saturation was observed at the highest tested dose of 400 UI/kg, which may be related to the available absorption area. Further, the rD'D3-FP dose limited availability of rVIII-SingleChain, i.e. the higher the rD'D3-FP dose, the better the rVIII-SingleChain availability. This can be transformed to relevant rD'D3-FP over rVIII-SingleChain tested ratios of at least 447 (≥3 mg/kg rD'D3-FP; excluding the 400 IU/kg rVIII-SingleChain dose with saturation), acceptable ratios in the tested range of 74-596 (1 mg/kg rD'D3-FP) and an unfavourable tested ratio of 45 (0.3 mg/kg rD'D3-FP). It was thus concluded that ratios <50 have shown an unfavourable bioavailability of FVIII, while those above 50 are favourable.

The bioavailability of rVIII-SingleChain was unproportionally lower when co-administered with rD'D3-His, i.e. 1% at a dose of 3 mg/kg rD'D3-His & 200 IU/kg rVIII-SingleChain, suggesting an advantage of the albumin fusion of rD'D3 for bioavailability of rVIIII-SingleChain.

Additionally time to trough was calculated for s.c. and i.v. administrations (Table 7). As for bioavailability, higher doses of rD'D3-FP and/or FVIII showed favourable trough levels, and within a constant FVIII or rD'D3-FP dose, an increase of the rD'D3-FP:rVIII-SingleChain ratio resulted in more favourable time to trough levels.

TABLE 5

Pharmacokinetic parameters of FVIII chromogenic activity after s.c. or i.v. administration of rD'D3-FP and rVIII-SingleChain in FVIII ko mice

| Treatment | $C_{max}$, extrap. mIU/mL | Clearance FVIII:activity mL/kg/h | MRT h | Half-life, terminal H | $AUC_{0-inf}$ mIU * h/mL |
|---|---|---|---|---|---|
| 10 mg/kg rD'D3-FP & 400 IU/kg rVIII-SingleChain s.c. | 692 | 12.2 | 37 | 17 | 32848 |
| 3 mg/kg rD'D3-FP & 400 IU/kg rVIII-SingleChain s.c. | 790 | 12.4 | 37 | 20 | 32387 |
| 3 mg/kg rD'D3-FP & 200 IU/kg rVIII-SingleChain s.c. | 621 | 7.5 | 32 | 11 | 26741 |
| 3 mg/kg rD'D3-FP & 100 IU/kg rVIII-SingleChain s.c. | 369 | 8.1 | 25 | 8 | 12409 |
| 3 mg/kg rD'D3-FP & 50 IU/kg rVIII-SingleChain s.c. | 186 | 8.8 | 24 | 6 | 5652 |
| 1 mg/kg rD'D3-FP & 400 IU/kg rVIII-SingleChain s.c. | 942 | 13.3 | 26 | 8 | 30028 |
| 1 mg/kg rD'D3-FP & 100 IU/kg rVIII-SingleChain s.c. | 138 | 23.7 | 27 | 16 | 4222 |
| 1 mg/kg rD'D3-FP & 50 IU/kg rVIII-SingleChain s.c. | 114 | 22.3 | 16 | 7 | 2243 |
| 0.3 mg/kg rD'D3-FP & 200 IU/kg rVIII-SingleChain s.c. | 224 | 44.9 | 17 | 9 | 4454 |
| 3 mg/kg rD'D3-His & 200 IU/kg rVIII-SingleChain s.c. | (82)* 81 | (79.2)* 139.7 | (30)* 7 | (29)* 6 | (1262)* 716 |
| 3 mg/kg rD'D3-FP & 100 IU/kg rVIII-SingleChain i.v. | 2958 | 1.3 | 25 | 18 | 74850 |

TABLE 5-continued

Pharmacokinetic parameters of FVIII chromogenic activity after s.c. or i.v. administration of rD'D3-FP and rVIII-SingleChain in FVIII ko mice

| Treatment | $C_{max}$, extrap. mIU/mL | Clearance FVIII:activity mL/kg/h | MRT h | Half-life, terminal H | $AUC_{0-inf}$ mIU * h/mL |
|---|---|---|---|---|---|
| 1 mg/kg rD'D3-FP & 100 IU/kg rVIII-SingleChain i.v. | 2323 | 1.8 | 23 | 16 | 54060 |
| 3 mg/kg rD'D3-His & 200 IU/kg rVIII-SingleChain i.v. | 5974 | 3.8 | 13 | 9 | 52824 |

*High similarity in the last two measurement points leads to an artificial "flattening out" of the plasma concentration curve in the terminal phase; thereby estimation of clearance, MRT, $t_{1/2}$ and $AUC_{0-inf}$ was estimated extremely long when including the last point. Therefore, an additional calculation was done without the last timepoint in order to avoid an overestimation of bioavailability.

TABLE 6

Bioavailability of rVIII-SingleChain (FVIII chromogenic activity) after s.c. administration in FVIII ko mice calculated against i.v. reference treatments

| | Bioavailability [%] to i.v. reference treatments[§] | | |
|---|---|---|---|
| S.c. treatment | 3 mg/kg rD'D3-FP & 100 IU/kg rVIII-SingleChain i.v. | 1 mg/kg rD'D3-FP & 100 IU/kg rVIII-SingleChain i.v. | 3 mg/kg rD'D3-His & 200 IU/kg rVIII-SingleChain i.v. |
| 10 mg/kg rD'D3-FP & 400 IU/kg rVIII-SingleChain s.c. | 11 | 15 | n.a. |
| 3 mg/kg rD'D3-FP & 400 IU/kg rVIII-SingleChain s.c. | 11 | 15 | n.a. |
| 3 mg/kg rD'D3-FP & 200 IU/kg rVIII-SingleChain s.c. | 18 | 25 | n.a. |
| 3 mg/kg rD'D3-FP & 100 IU/kg rVIII-SingleChain s.c. | 17 | 23 | n.a. |
| 3 mg/kg rD'D3-FP & 50 IU/kg rVIII-SingleChain s.c. | 15 | 21 | n.a. |
| 1 mg/kg rD'D3-FP & 400 IU/kg rVIII-SingleChain s.c. | 10 | 14 | n.a. |
| 1 mg/kg rD'D3-FP & 100 IU/kg rVIII-SingleChain s.c. | 6 | 8 | n.a. |
| 1 mg/kg rD'D3-FP & 50 IU/kg rVIII-SingleChain s.c. | 6 | 8 | n.a. |
| 0.3 mg/kg rD'D3-FP & 200 IU/kg rVIII-SingleChain s.c. | 3 | 4 | n.a. |
| 3 mg/kg rD'D3-His & 200 IU/kg rVIII-SingleChain s.c. | n.a. | n.a. | 1* | n.a.—not applicable;
*lower confidence in AUC estimate of s.c. data (see above)
[§]reference group with same treatment is given in bold

TABLE 7

Time to trough levels of rVIII-SingleChain (FVIII chromogenic activity) after s.c. administration in FVIII ko mice

| Treatment | 1% trough [h] | Time to 5% trough [h] | 10% trough [h] |
|---|---|---|---|
| 10 mg/kg rD'D3-FP & 400 IU/kg rVIII-SingleChain s.c. | 133 | 97 | 80 |
| 3 mg/kg rD'D3-FP & 400 IU/kg rVIII-SingleChain s.c. | 145 | 99 | 78 |
| 3 mg/kg rD'D3-FP & 200 IU/kg rVIII-SingleChain s.c. | 111 | 82 | 68 |
| 3 mg/kg rD'D3-FP & 100 IU/kg rVIII-SingleChain s.c. | 76 | 55 | 45 |
| 3 mg/kg rD'D3-FP & 50 IU/kg rVIII-SingleChain s.c. | 62 | 43 | 33 |
| 1 mg/kg rD'D3-FP & 400 IU/kg rVIII-SingleChain s.c. | 90 | 69 | 59 |
| 1 mg/kg rD'D3-FP & 100 IU/kg rVIII-SingleChain s.c. | 69 | 34 | 18 |
| 1 mg/kg rD'D3-FP & 50 IU/kg rVIII-SingleChain s.c. | 38 | 22 | 6 |
| 0.3 mg/kg rD'D3-FP & 200 IU/kg rVIII-SingleChain s.c. | 50 | 29 | 20 |
| 3 mg/kg rD'D3-His & 200 IU/kg rVIII-SingleChain s.c. | 15 | 7 | 3 |
| 3 mg/kg rDD3-FP & 100 IU/kg rVIII-SingleChain i.v. | 127 | 87 | 69 |
| 1 mg/kg rDD3-FP & 100 IU/kg rVIII-SingleChain i.v. | 109 | 73 | 57 |
| 3 mg/kg rDD3-His & 200 IU/kg rVIII-SingleChain i.v. | 78 | 57 | 48 |

Example 1.2: Subcutaneous Bioavailability of Recombinant FVIII, rVIII-SingleChain, in the Presence of rD'D3-FP in Pigs Experimental Details The test articles were administered s.c. in the flanks or i.v. into the ear vein by a single injection, at a total volume ranging from 0.211 to 0.751 mL/kg. Administered dose levels and routes are given in Table 8.

TABLE 8

Treatment groups

| rD'D3-FP [mg albumin/kg] | rVIII-SingleChain [IU FVIII:C/kg] | Route and duration of observation | Ratio rD'D3-FP:rFVIII |
|---|---|---|---|
| 10 | 400 | sc (168 h) | 745 |
| 10 | 400 | iv (168 h) | 745 |
| 3 | 200 | sc (264 h) | 447 |
| 3 | 100 | sc (264 h) | 894 |
| 3 | — | sc (264 h) | — | rD'D3-FP was applied in a dose range from 3 to 10 mg/kg based on human albumin values, rVIII-SingleChain doses ranged from 100 to 400 μL/kg chromogenic FVIII activity. rVIII-SingleChain was reconstituted with water for injection, and rD'D3-FP thawed in a water bath.

Blood samples were taken from the ear or saphenous vein. Timepoints in the 10 mg/kg rD'D3-FP s.c. groups were pre-dose, 3, 12, 24, 32, 48, 72, 96, 120, 144 and 168 h p.a., and in the i.v. group pre-dose 5 min, 3, 12, 24, 32, 48, 72, 96, 120, 144 and 168 h p.a. Timepoints in the 3 mg/kg rD'D3-FP s.c. groups were pre-dose, 1, 3, 12, 24, 48, 72, 96, 120, 144, 168, 192, 216, 240 and 264 h p.a.

The PK profile was taken from individual animals. Blood samples were anticoagulated using sodium citrate (1 parts sodium citrate 3.13%+9 parts blood), processed to plasma and stored at −70° C. for the determination of FVIII antigen and albumin.

rD'D3-FP exposure was determined by measurement of the albumin part of the protein using a human albumin ELISA. Human FVIII:Ag plasma levels were determined with the FVIII Asserachrom ELISA.

Biostatistics

Estimation of the maximal concentration ($C_{max}$), the area under the concentration over time curve from t=0 to t=∞ ($AUC_{0-inf}$), mean residence time (MRT), clearance (CL) and terminal half-life ($t_{1/2}$) was done by two-compartmental modelling in the i.v. calculations, and by two-compartmental-resorption modelling in the s.c. calculations. For parameter estimation, a weighted least-squares cost function was applied. Bioavailability was calculated as the percentage of the $AUC_{0-inf}$ after s.c. administration as compared to i.v. administration. Time to 1, 5 and 10% trough levels was calculated by setting the model equation equal to 0.01, 0.05 or 0.1 IU/mL and solving for time.

Results

Figure 7:
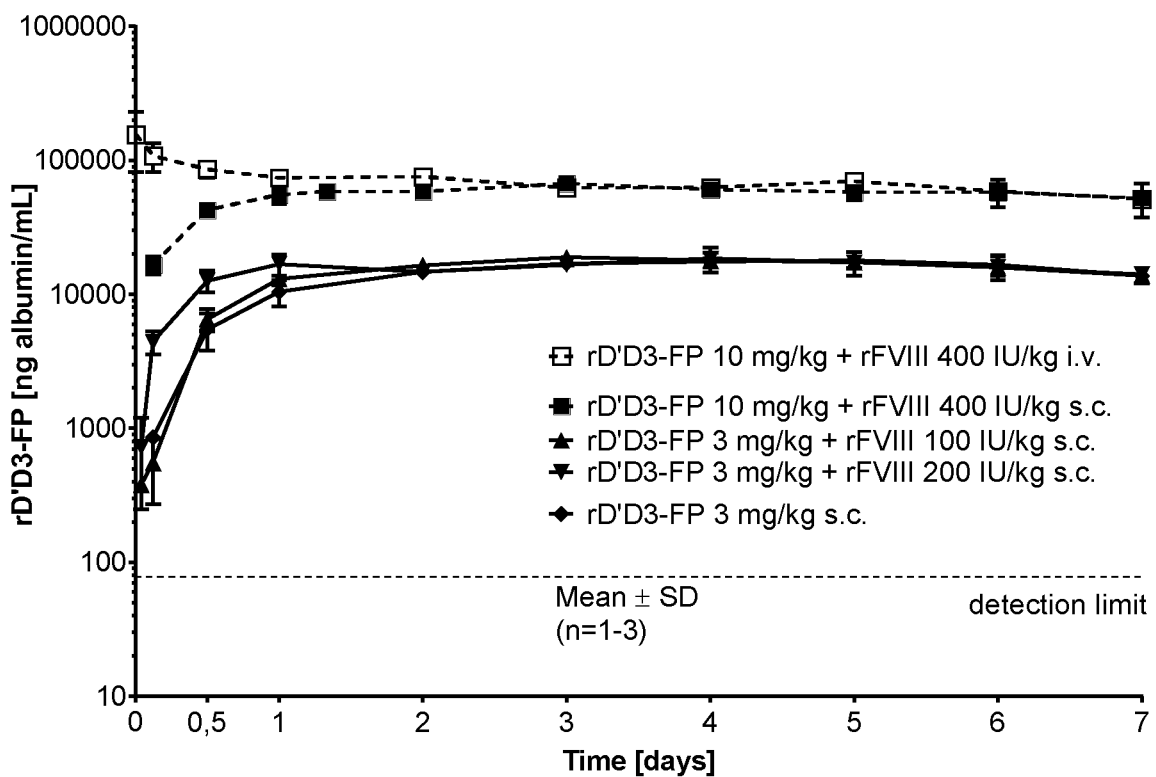
FIG. 7 shows recombinant polypeptide plasma levels after subcutaneous or intravenous administration of rD'D3-FP with or without recombinant FVIII in pigs. rD'D3-FP was quantified via its albumin component. Data is given as mean±SD for n=1-3 pigs per timepoint. Solid lines represent s.c. and dotted lines i.v. treatment. Abbreviation: s.c.: subcutaneous; i.v.: intravenous.

Evaluation of D'D3 Data rD'D3-FP was absorbed after s.c. administration and quantified over the whole period of observation of up to 168 h at 3 and 10 mg/kg; i.e. it remained above the detection limit of 23.4 ng/mL (FIG. 7).

$C_{max}$ and $AUC_{0-inf}$ showed dose-dependency in the tested range of 3-10 mg/kg rD'D3-FP (Table 9). $C_{max}$ was independent of the added rFVIII in the range of 0-400 IU/kg rVIII-SingleChain, while $AUC_{0-inf}$ of rD'D3-FP increased with the dose of the added rVIII-SingleChain. Clearance, MRT and $t_{1/2}$ showed a longer PK profile for rD'D3-FP for animals treated with 200 or 400 IU/kg rVIII-SingleChain as compared to 100 IU/kg or rVIII-SingleChain given alone (Table 9), i.e. rD'D3-FP loaded with FVIII remained longer in the system than without relevant amounts of FVIII.

In line with this, bioavailability of rD'D3-FP after subcutaneous administration ranges from 59-187% (Table 10), with higher values being reached with the highest co-administered FVIII doses. In conclusion, rVIII-SingleChain supported subcutaneous absorption of rD'D3-FP.

TABLE 9

Pharmacokinetic parameters of rD'D3-FP after s.c. or i.v. administration of rD'D3-FP and rVIII-SingleChain in pigs

| Treatment | $C_{max}$, extrap. [μg/mL] | Clearance Albumin [mL/kg/h] | MRT [h] | Half-life, terminal [h] | $AUC_{0-inf}$ [μg * h/mL] |
|---|---|---|---|---|---|
| 3 mg/kg rD'D3-FP s.c. | 17.6 | 0.5 | 271 | 154 | 5968 |
| 10 mg/kg rD'D3-FP & 400 IU/kg rVIII-SingleChain s.c. | 61.7 | 0.16 | 979 | 671 | 62813 |
| 3 mg/kg rD'D3-FP & 200 IU/kg rVIII-SingleChain s.c. | 17.4 | 0.18 | 939 | 644 | 16861 |
| 3 mg/kg rD'D3-FP & 100 IU/kg rVIII-SingleChain s.c. | 18.2 | 0.43 | 318 | 191 | 7013 |

TABLE 10

Bioavailability of rD'D3-FP after s.c. administration in pigs calculated against i.v. reference treatments

| S.c. treatment | Bioavailability [%] to i.v. reference treatment: 10 mg/kg rD'D3-FP & 400 IU/kg rVIII-SingleChain i.v.[§] |
|---|---|
| 3 mg/kg rD'D3-FP s.c. | 59 |
| 10 mg/kg rD'D3-FP & 400 IU/kg rVIII-SingleChain s.c. | 187 |
| 3 mg/kg rD'D3-FP & 200 IU/kg rVIII-SingleChain s.c. | 167 |
| 3 mg/kg rD'D3-FP & 100 IU/kg rVIII-SingleChain s.c. | 70 |

[§]reference group with same treatment is given in bold

Evaluation of FVIII Data

Figure 8:
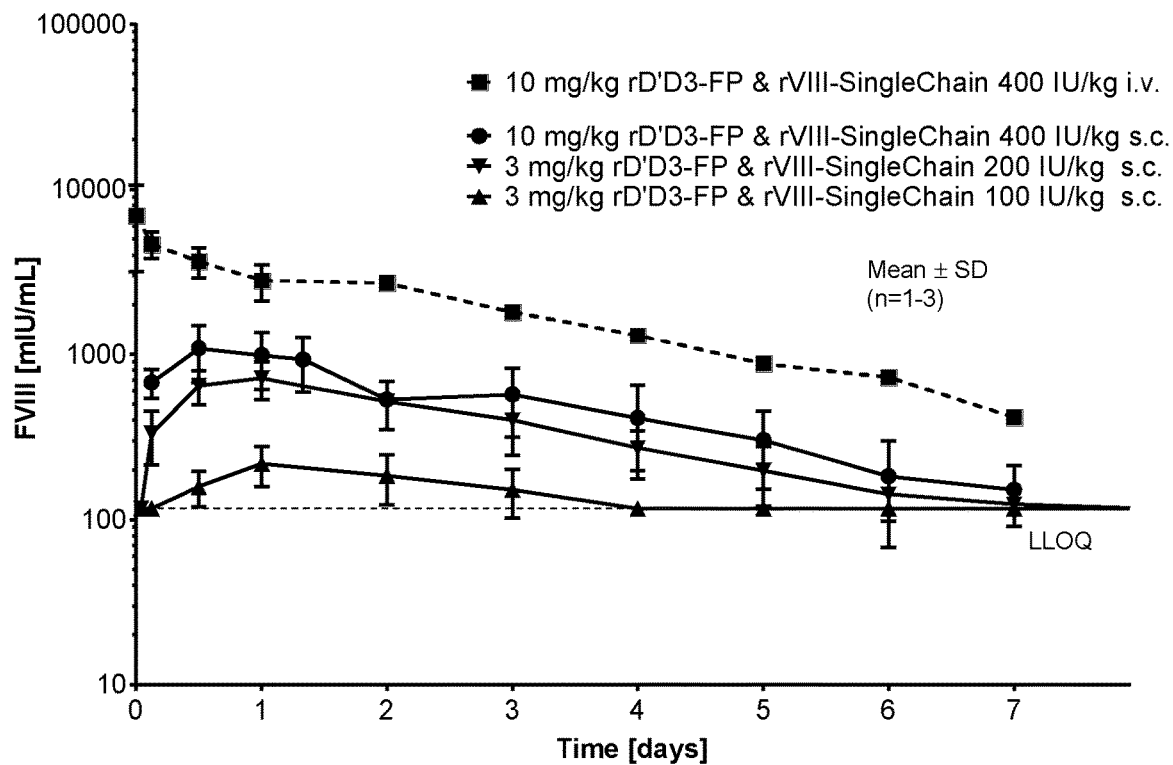
FIG. 8 shows FVIII activity plasma levels after subcutaneous or intravenous administration of rD'D3-FP with or without recombinant FVIII in pigs. FVIII was quantified as chromogenic FVIII activity. Data is given as mean±SD for n=1-3 pigs per timepoint. Solid lines represent s.c. and dotted lines i.v. treatment; Abbreviation: s.c.: subcutaneous; i.v.: intravenous.

FVIII was surprisingly absorbed when co-administered s.c. with rD'D3-FP and FVIII activity endured the absorption process (FIG. 8). Dependent on the FVIII dose, FVIII activity was quantified for at least 48 h (3 mg/kg rD'D3-FP & 100 IU/kg rVIII-SingleChain) and up to 168 h (e.g. any dose with 400 IU/kg rVIII-SingleChain and 3 or 10 mg/kg rD'D3-FP); i.e. it remained over the detection limit of 117 mIU/mL.

$C_{max}$ and $AUC_{0-inf}$ showed dose-dependency in the tested range of 100-400 IU/kg rVIII-SingleChain. Values were expectedly higher after i.v. administration of the drugs (Table 10).

Clearance of FVIII activity was higher (2.9-4.1 mL/kg/h) after s.c. than after i.v. (1.2 mL/kg/h) administration. Nevertheless, MRT and $t_{1/2}$ was comparable after s.c. and i.v. administration (82 & 85 h vs. 77 h and 52 & 59 h vs. 54 h, respectively) with higher rVIII-SingleChain doses of 200 or 400 UI/kg. At the lower dose of 100 IU/kg, MRT and $t_{1/2}$ were even longer for rVIII-SingleChain (130 and 83 h, respectively). Thus, pharmacokinetic parameters after s.c. administration were roughly comparable to those after i.v. administration with higher doses of rVIII-SingleChain, and superior at a dose of 100 IU/kg rVIII-SingleChain.

Bioavailability of rVIII-SingleChain ranged from 29-40%, increasing with the dose of rVIII-SingleChain and/or rD'D3-FP (Table 12).

Additionally time to trough was calculated for s.c. and i.v. administrations (Table 13). Time to 1% trough levels were comparable for all s.c. doses, while time to 5% or 10% trough was comparable for 200 and 400 UI/kg rVIII-SingleChain+3 or 10 mg/kg rD'D3-FP, and superior for 100 IU/kg rVIII-SingleChain+3 mg/kg rD'D3-FP.

TABLE 11

Pharmacokinetic parameters of FVIII activity after s.c. or i.v. administration of rD'D3-FP and rVIII-SingleChain in pigs

| Treatment | $C_{max}$, extrap. [IU/mL] | Clearance FVIII:activity [mL/kg/h] | MRT [h] | Half-life, terminal [h] | $AUC_{0\text{-}inf}$ [IU * h/mL] |
|---|---|---|---|---|---|
| 10 mg/kg rD'D3-FP & 400 IU/kg rVIII-SingleChain i.v. | 7.0 | 1.2 | 77 | 54 | 339 |
| 10 mg/kg rD'D3-FP & 400 IU/kg rVIII-SingleChain s.c. | 1.1 | 4.1 | 85 | 59 | 97 |
| 3 mg/kg rD'D3-FP & 200 IU/kg rVIII-SingleChain s.c. | 0.7 | 2.9 | 82 | 52 | 68 |
| 3 mg/kg rD'D3-FP & 100 IU/kg rVIII-SingleChain s.c. | 0.2 | 3.1 | 130 | 83 | 31 |

TABLE 12

Bioavailability of rVIII-SingleChain (FVIII activity) after s.c. administration in pigs calculated against i.v. reference treatments

| S.c. treatment | Bioavailability [%] to i.v. reference treatment: 10 mg/kg rD'D3-FP & 400 IU/kg rVIII-SingleChain i.v.[§] |
|---|---|
| 10 mg/kg rD'D3-FP & 400 IU/kg rVIII-SingleChain s.c. | 29 |
| 3 mg/kg rD'D3-FP & 200 IU/kg rVIII-SingleChain s.c. | 40 |
| 3 mg/kg rD'D3-FP & 100 IU/kg rVIII-SingleChain s.c. | 37 |

[§]reference group with same treatment is given in bold

TABLE 13

Time to trough levels of rVIII-SingleChain (FVIII antigen) after s.c. administration in pigs

| Treatment | 1% trough [h] | Time to 5% trough [h] | 10% trough [h] |
|---|---|---|---|
| 10 mg/kg rD'D3-FP & 400 IU/kg rVIII-SingleChain i.v. | 319 | 195 | 141 |
| 10 mg/kg rD'D3-FP & 400 IU/kg rVIII-SingleChain s.c. | 383 | 255 | 196 |
| 3 mg/kg rD'D3-FP & 200 IU/kg rVIII-SingleChain s.c. | 349 | 249 | 198 |
| 3 mg/kg rD'D3-FP & 100 IU/kg rVIII-SingleChain s.c. | 388 | 349 | 303 |

Example 1.3: Investigation of the Effect of rD'D3-FP on Different FVIII Products, Each Given Subcutaneously in a Mouse Hemophilia a Model, i.e. in FVIII Ko Mice Experimental Details The test articles were administered s.c. in the neck or i.v. into the lateral tail vein by a single injection, at a total volume of 5 mL/kg. Administered dose levels and routes are given in Table 14.

TABLE 14

Treatment groups

| rD'D3-FP [mg albumin/kg] | FVIII [IU FVIII:C/kg] | Route | Ratio rD'D3-FP:rFVIII |
|---|---|---|---|
| 3 | 200 Beriate ® | sc | 322 |
| 3 | 200 Beriate ® | iv | 322 |

TABLE 14-continued

Treatment groups

| rD'D3-FP [mg albumin/kg] | FVIII [IU FVIII:C/kg] | Route | Ratio rD'D3-FP:rFVIII |
|---|---|---|---|
| — | 200 Beriate ® | sc | — |
| 3 | 200 Advate ® | sc | 442 |
| 3 | 200 Advate ® | iv | 442 |
| — | 200 Advate ® | sc | — |
| 3 | 200 ReFacto AF ® | sc | 410 |
| 3 | 200 ReFacto AF ® | iv | 410 |
| — | 200 ReFacto AF ® | sc | — | rD'D3-FP was applied in a dose of 3 mg/kg based on human albumin values, and FVIII products at a dose of 200 IU/kg chromogenic FVIII activity (nominal: Advate® and ReFacto AF®, Certificate of Analysis: Beriate®). Advate® and ReFacto® AF were reconstituted according to the package insert. Beriate® was reconstituted with water for injection using a pipette. rD'D3-FP was thawed in a water bath and mixed with respective FVIII product. In every case, a dose volume of mL/kg was administered, dilution buffer for FVIII was used for all products.

It shall be mentioned that the ratio of rD'D3-FP:rFVIII was in a comparably high range from 322 to 442 for the four different products, based on their different molecular weights and specific activities.

Blood samples were taken retrobulbary under short term anaesthesia using an alternating sampling scheme. Timepoints in the s.c. groups were 3, 8, 16, 24, 32, 48, 72, and 96 h p.a., and in the i.v. groups 5 min, 3, 8, 16, 24, 48, 72, and 96 h p.a. The PK profile was taken from four cohorts of mice per group, and n=3 per timepoint. Blood samples were anticoagulated using sodium citrate (1 parts sodium citrate 3.13%+9 parts blood), processed to plasma and stored at −70° C. for the determination of chromogenic FVIII activity and albumin.

rD'D3-FP exposure was determined by measurement of the albumin part of the construct using a human albumin ELISA. Further, FVIII chromogenic activity measured.

Biostatistics

Estimation of the maximal concentration ($C_{max}$), the area under the concentration over time curve from t=0 to t=∞ ($AUC_{0-inf}$), mean residence time (MRT), clearance (CL) and terminal half-life ($t_{1/2}$) was done by two-compartmental modelling in the i.v. calculations, and by two-compartmental-resorption modelling in the s.c. calculations. For parameter estimation, a weighted least-squares cost function was applied. Bioavailability was calculated as the percentage of the $AUC_{0-inf}$ after s.c. administration as compared to i.v. administration. Time to 1, 5 and 10% trough levels was calculated by setting the model equation equal to 0.01, 0.05 or 0.1 IU/mL and solving for time.

Results

Evaluation of D'D3 Data

Figure 9:
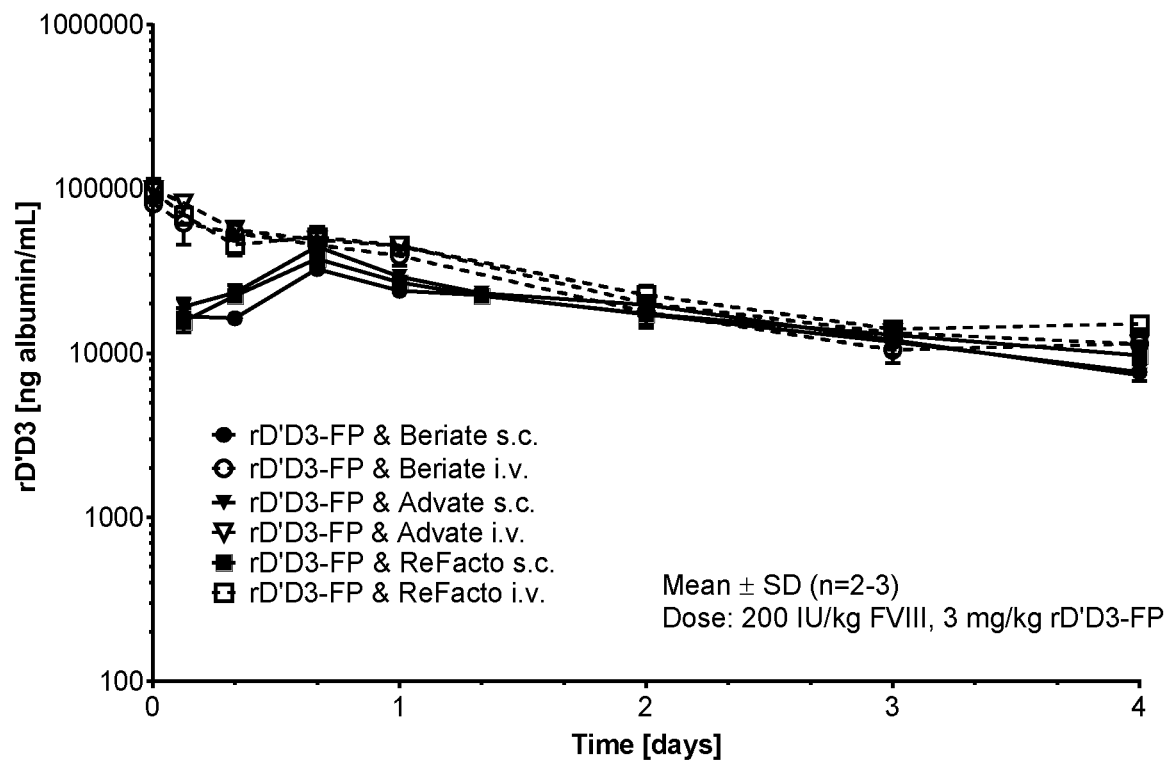
FIG. 9 shows recombinant polypeptide plasma levels after subcutaneous or intravenous administration of rD'D3-FP with or without different recombinant FVIII or a plasma derived FVIII in FVIII ko mice. rD'D3-FP was quantified via its albumin component. Data is given as mean±SD for n=2-3 mice per timepoint. Solid lines represent s.c. and dotted lines i.v. treatment. Abbreviation: s.c.: subcutaneous; i.v.: intravenous.

Independent of the co-administered FVIII product, rD'D3-FP was absorbed after s.c. administration. rD'D3-FP could be quantified over the whole period of observation of 96 h and remained above the detection limit of 23.4 ng/mL (FIG. 9).

There was no visible difference in the PK profiles of rD'D3-FP after i.v. or s.c. administration, respectively, in dependence of the co-administered FVIII. In line with this, the estimation of clearance, MRT, $t_{1/2}$ and $AUC_{0-inf}$ shows good agreement of the data for all s.c. or i.v. treatments, respectively (Table 15). In detail, clearance was in the range of 0.9 to 1.1 mL/kg for i.v. and was slightly higher after s.c. administration (1.0 to 1.5 mL/kg/h). In line with this, MRT and $t_{1/2}$ ranged between 40-56 h and 31-40 h for i.v and between 61-117 h and 35-89 h for s.c. treatment respectively; i.e. clearance was lower for i.v. but typically MRT and $t_{1/2}$ were nevertheless shorter for i.v. treatment.

Importantly, bioavailability of rD'D3-FP after subcutaneous administration ranges from 56-87% (Table 16), and does not differ relevantly between the different co-administered FVIII products. It is very comparable to that of rVIII-SingleChain (Table 4, range 40-79%).

TABLE 15

Pharmacokinetic parameters of rD'D3-FP after s.c. or i.v. administration of rD'D3-FP and different FVIIII products in FVIII ko mice

| Treatment | $C_{max}$, extrap. [μg/mL] | Clearance Albumin [mL/kg/h] | MRT [h] | Half-life, terminal [h] | $AUC_{0-inf}$ [μg * h/mL] |
|---|---|---|---|---|---|
| 3 mg/kg rD'D3-FP & 200 IU/kg Beriate ® s.c. | 26.2 | 1.5 | 61 | 35 | 1940 |
| 3 mg/kg rD'D3-FP & 200 IU/kg Beriate ® i.v. | 74.3 | 1.1 | 40 | 31 | 2667 |
| 3 mg/kg rD'D3-FP & 200 IU/kg Advate ® s.c. | 35.4 | 1.1 | 85 | 71 | 2624 |
| 3 mg/kg rD'D3-FP & 200 IU/kg Advate ® i.v. | 101.3 | 0.9 | 46 | 33 | 3268 |
| 3 mg/kg rD'D3-FP & 200 IU/kg ReFacto ® AF s.c. | 30.3 | 1.0 | 117 | 89 | 2987 |
| 3 mg/kg rD'D3-FP & 200 IU/kg ReFacto ® AF i.v. | 99.4 | 0.9 | 56 | 40 | 3488 |

TABLE 16

Bioavailability of rD'D3-FP after s.c. administration in FVIII ko mice calculated against i.v. reference treatments

| S.c. treatment | Bioavailability [%] to i.v. reference treatments: rD'D3-FP with respective FVIII product i.v. |
|---|---|
| 3 mg/kg rD'D3-FP & 200 IU/kg Beriate ® s.c. | 56 |
| 3 mg/kg rD'D3-FP & 200 IU/kg Advate ® s.c. | 80 |
| 3 mg/kg rD'D3-FP & 200 IU/kg ReFacto ® AF s.c. | 87 |

Evaluation of FVIII Data

Figure 10A:
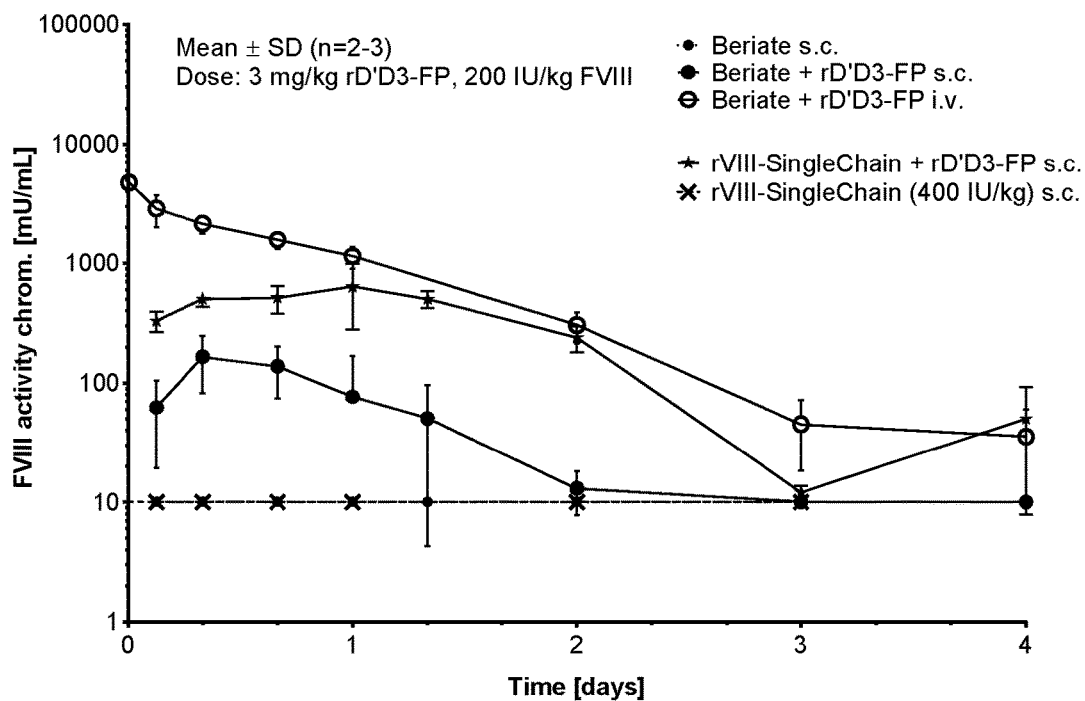
FIGS. 10A, 10B, and 10C show FVIII activity plasma levels after subcutaneous or intravenous administration of rD'D3-FP with or without different recombinant FVIII or a plasma derived FVIII in FVIII ko mice (FIG. 10A Beriate®, FIG. 10B Advate® and FIG. 10C ReFacto AF®). FVIII was quantified as chromogenic FVIII activity. Data is given as mean±SD for n=2-3 mice per timepoint. Solid lines represent s.c. and dotted lines i.v. treatment; Abbreviation: s.c.: subcutaneous; i.v.: intravenous.
Figure 10B:
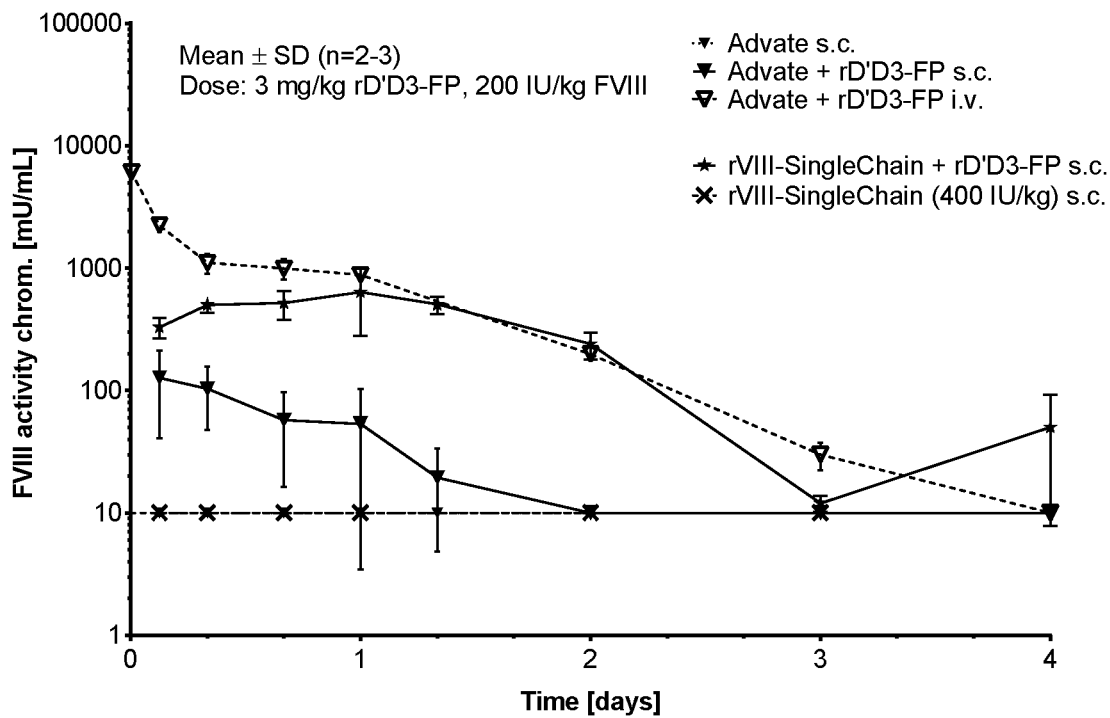
Figure 10C:
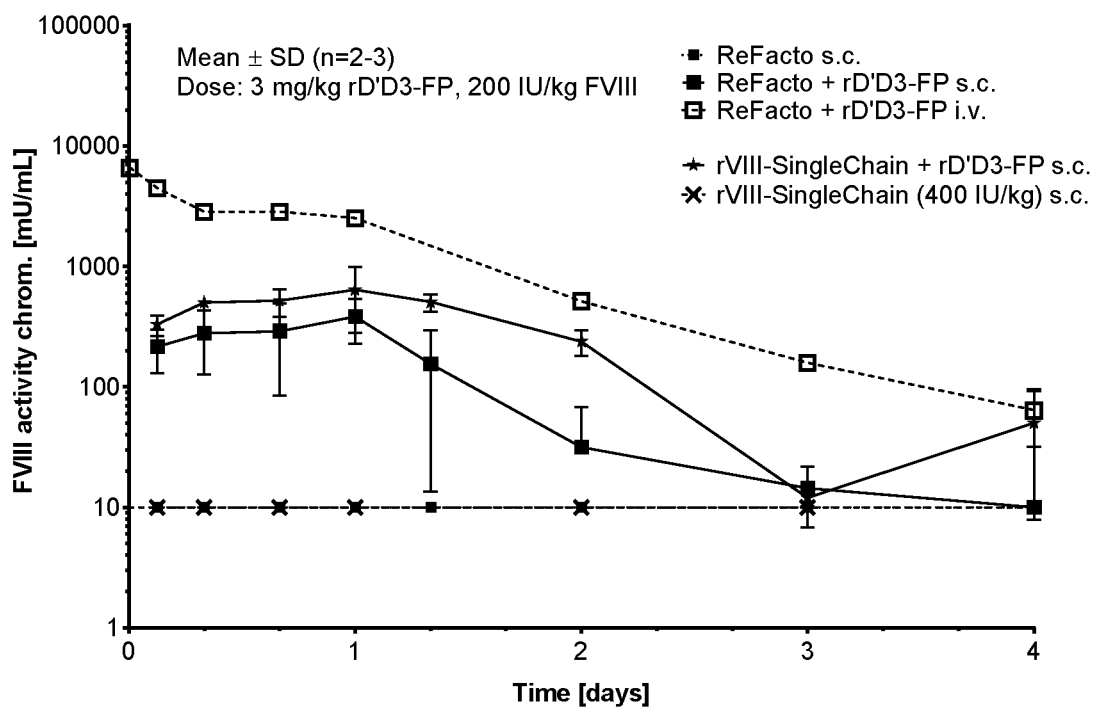

All of the FVIII products were absorbed when co-administered s.c. with rD'D3-FP and FVIII activity endured the absorption process (FIGS. 10A, 10B, 10C). In contrast, none of the products showed relevant s.c. bioavailability when given alone.

Data from estimation of $C_{max}$, $AUC_{0-inf}$ clearance, MRT and $t_{1/2}$ is given in Table 17. While the different FVIII products showed different PK profiles when given alone, clearance was always increased after s.c. administration as compared to i.v. administration, i.e. from 3.1 to 51.5 mL/kg/h for Beriate®, from 4.4 to 78.5 mL/kg/h for Advate® and from 1.7 to 16.2 mL/kg/h for ReFacto AF®. MRT was about comparable between s.c. and i.v. administration (Beriate® and Advate®: range 17-19 h; ReFacto AF®: range 21-28 h), in line with the results from co-administration of rVIII-SingleChain (see Table 11). For these other FVIII products, $t_{1/2}$ tended to be longer after i.v. administration as compared to s.c. administration (Beriate: 8 h s.c. to 13 h i.v.; Advate®: 12 h s.c. to 14 h i.v.; ReFacto AF®: 11 h s.c. to 15 h i.v.).

Subcutaneous bioavailability of the different FVIII products co-administered with rD'D3-FP ranged from 6-11%, suggesting no relevant difference between the FVIII products (Table 18). This is slightly less as compared with the observed 20% when co-administering rD'D3-FP with rVIII-SingleChain (see Table 12); nevertheless all bioavailabilities of FVIII products were within an acceptable range. This indicates that rD'D3-FP plays the key role for FVIII resorption after subcutaneous administration. However, a combination of a rD'D3-FP with rVIII-SingleChain may further improve bioavailability of FVIII.

Additionally time to trough was calculated for s.c. and i.v. administrations (Table 19). For 1% trough levels, data were about comparable after i.v. and s.c. administration (Beriate® 60 and 79 h, Advate® 66 and 68 h, ReFacto® AF 98 and 104 h). Time to trough for 5% or 10% levels was superior after s.c. as compared to i.v. administration: Beriate showed superiority of s.c. over i.v. by 4% (5% trough) and 17% (10% trough), Advate® by 29% (5% trough) and 50% (10% trough) and ReFacto® AF by 50% (5% trough) and 28% (10% trough), respectively.

TABLE 17

Pharmacokinetic parameters of FVIII antigen after s.c. or i.v. administration of rD'D3-FP and different FVIIII products in FVIII ko mice

| Treatment | $C_{max}$, extrap. [IU/mL] | Clearance FVIII antigen [mL/kg/h] | MRT [h] | Half-life, terminal [h] | $AUC_{0-inf}$ [IU * h/mL] |
|---|---|---|---|---|---|
| 200 IU/kg Beriate ® s.c. | n.a. | n.a. | n.a. | n.a. | n.a. |
| 3 mg/kg rD'D3-FP & 200 IU/kg Beriate ® s.c. | 0.17 | 51.5 | 18 | 8 | 4 |

TABLE 17-continued

Pharmacokinetic parameters of FVIII antigen after s.c. or i.v. administration of rD'D3-FP and different FVIII products in FVIII ko mice

| Treatment | $C_{max}$, extrap. [IU/mL] | Clearance FVIII antigen [mL/kg/h] | MRT [h] | Half-life, terminal [h] | $AUC_{0-inf}$ [IU * h/mL] |
|---|---|---|---|---|---|
| 3 mg/kg rD'D3-FP & 200 IU/kg Beriate ® i.v. | 5.31 | 3.1 | 19 | 13 | 66 |
| 200 IU/kg Advate ® s.c. | n.a. | n.a. | n.a. | n.a. | n.a. |
| 3 mg/kg rD'D3-FP & 200 IU/kg Advate ® s.c. | 0.13 | 78.5 | 19 | 12 | 3 |
| 3 mg/kg rD'D3-FP & 200 IU/kg Advate ® i.v. | 6.37 | 4.4 | 17 | 14 | 45 |
| 200 IU/kg ReFacto ® AF s.c. | n.a. | n.a. | n.a. | n.a. | n.a. |
| 3 mg/kg rD'D3-FP & 200 IU/kg ReFacto ® AF s.c. | 0.32 | 16.2 | 28 | 11 | 12 |
| 3 mg/kg rD'D3-FP & 200 IU/kg ReFacto ® AF i.v. | 5.46 | 1.7 | 21 | 15 | 116 | n.a.: modelling not applicable (data below detection limit)

TABLE 18

Bioavailability of different FVIII products (FVIII antigen) after s.c. administration in FVIII ko mice calculated against i.v. reference treatments

| S.c. treatment | Bioavailability [%] to i.v. reference treatments: rD'D3-FP with respective FVIII product i.v. |
|---|---|
| 200 IU/kg Beriate ® s.c. | n.a. |
| 3 mg/kg rD'D3-FP & 200 IU/kg Beriate ® s.c. | 6 |
| 200 IU/kg Advate ® s.c. | n.a. |
| 3 mg/kg rD'D3-FP & 200 IU/kg Advate ® s.c. | 6 |
| 200 IU/kg ReFacto ® AF s.c. | n.a. |
| 3 mg/kg rD'D3-FP & 200 IU/kg ReFacto ® AF s.c. | 11 | n.a.—not applicable

TABLE 19

Time to trough levels of different FVIII products (FVIII antigen) after s.c. or i.v. administration in FVIII ko mice

| Treatment | 1% trough [h] | Time to 5% trough [h] | 10% trough [h] |
|---|---|---|---|
| 200 IU/kg Beriate ® s.c. | n.a. | n.a. | n.a. |
| 3 mg/kg rD'D3-FP & 200 IU/kg Beriate ® s.c. | 60 | 50 | 42 |
| 3 mg/kg rD'D3-FP & 200 IU/kg Beriate ® i.v. | 79 | 48 | 35 |
| 200 IU/kg Advate ® s.c. | n.a. | n.a. | n.a. |
| 3 mg/kg rD'D3-FP & 200 IU/kg Advate ® s.c. | 66 | 51 | 44 |
| 3 mg/kg rD'D3-FP & 200 IU/kg Advate ® i.v. | 68 | 36 | 22 |
| 200 IU/kg ReFacto AF ® s.c. | n.a. | n.a. | n.a. |
| 3 mg/kg rD'D3-FP & 200 IU/kg ReFacto ® AF s.c. | 104 | 80 | 68 |
| 3 mg/kg rD'D3-FP & 200 IU/kg ReFacto ® AF i.v. | 98 | 64 | 49 | n.a.: modelling not applicable (data below detection limit)

Example 1.4: Investigation of the Effect of a rD'D3-FP Affinity Variant, a rD'D3 Molecule with Non-Albumin HELP and rVIII-SingleChain Given Both Subcutaneously in a Mouse Hemophilia a Model, i.e. in FVIII Ko Mice Experimental Details The test articles were administered s.c. in the neck or i.v. into the lateral tail vein by a single injection, at a total volume of 5 mL/kg. Administered dose levels and routes are given in Table 20.

TABLE 20

Treatment groups

| rD'D3 variant [mg/kg] | rVIII-SingleChain [IU FVIII:C/kg] | Route | Ratio rD'D3-FP:rFVIII |
|---|---|---|---|
| 3 rD'D3-FP EYA | 200 | sc | 447 |
| 3 rD'D3-FP EYA | 200 | iv | 447 |
| 4.29 rD'D3-CTP | 200 | sc | 608 |
| 4.29 rD'D3-CTP | 200 | iv | 608 | rD'D3-FP EYA was applied at a dose of 3 mg/kg based on human albumin values, rD'D3-CTP at a dose of 4.29 mg/kg based on protein content (leading both to high rD'D3 variant: rVIII-SingleChain doses, Table 20), and FVIII products at a dose of 200 IU/kg chromogenic FVIII activity. rVIII-SingleChain was reconstituted with water for injection, and rD'D3-FP EYA as well as rD'D3-CTP was thawed in a water bath. In every case, a dose volume of 5 mUkg was administered, using dilution buffer for FVIII for dilution.

Blood samples were taken retrobulbary under short term anaesthesia using an alternating sampling scheme. Timepoints in the s.c. groups were 3, 8, 16, 24, 32, 48, 72, and 96 h p.a., and in the i.v. groups 5 min, 3, 8, 16, 24, 48, 72, and 96 h p.a. The PK profile was taken from four cohorts of mice per group, and n=3 per timepoint. Blood samples were anticoagulated using sodium citrate (1 parts sodium citrate 3.13%+9 parts blood), processed to plasma and stored at −70° C. for the determination of FVIII activity, albumin and/or rD'D3-CTP.

rD'D3-FP EYA exposure was determined by measurement of the albumin part of the construct using a human albumin ELISA. rD'D3-CTP was measured by an ELISA technique using antibodies against anti-human D'D3. Further, FVIII chromogenic activity was measured.

Biostatistics

Estimation of the maximal concentration ($C_{max}$), the area under the concentration over time curve from t=0 to t=∞ ($AUC_{0-inf}$), mean residence time (MRT), clearance (CL) and terminal half-life ($t_{1/2}$) was done by two-compartmental modelling in the i.v. calculations, and by two-compartmental-resorption modelling in the s.c. calculations. For parameter estimation, a weighted least-squares cost function was applied. Bioavailability was calculated as the percentage of the $AUC_{0-inf}$ after s.c. administration as compared to i.v. administration. Time to 1, 5 and 10% trough levels was calculated by setting the model equation equal to 0.01, 0.05 or 0.1 IU/mL and solving for time.

Results

Evaluation of D'D3 Data

Figure 11:
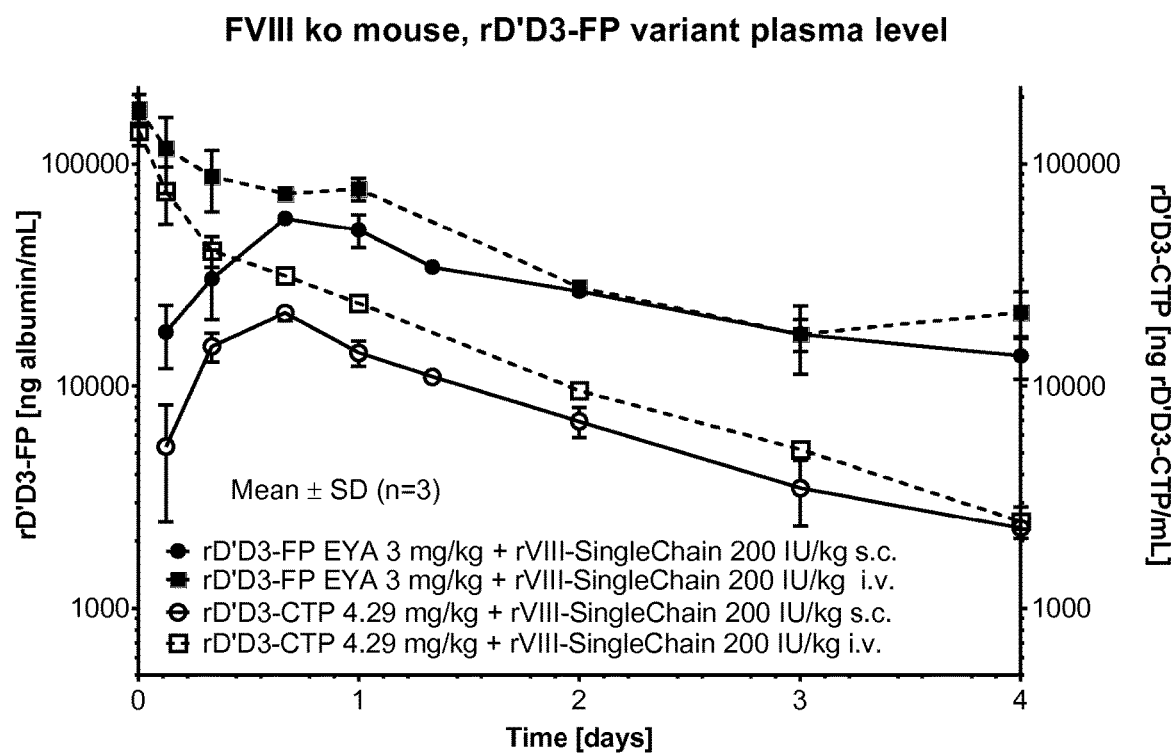
FIG. 11 shows recombinant polypeptide plasma levels after subcutaneous or intravenous administration of rD'D3-FP EYA or rD'D3-CTP with recombinant FVIII in FVIII ko mice. rD'D3-FP EYA was quantified via its albumin component and rD'D3-CTP via its D'D3 component. Data is given as mean±SD for n=3 mice per timepoint. Solid lines represent s.c. and dotted lines i.v. treatment. Abbreviation: s.c.: subcutaneous; i.v.: intravenous.

Both, rD'D3-FP EYA and rD'D3-CTP, were absorbed after s.c. administration, and could both be quantified over the whole period of observation of 96 h, i.e. remaining above the detection limit of 23.4 ng/mL (FIG. 11).

Estimation of clearance, MRT, $t_{1/2}$ and $AUC_{0-inf}$ is given in Table 21, showing longer $t_{1/2}$ and MRT for rD'D3-FP EYA as compared to rD'D3-CTP after i.v. as well as after s.c. administration ($t_{1/2}$: 30 h i.v. and 32 h s.c. for EYA longer than 22 h for CTP; MRT: 42 h i.v. and 57 h s.c. for EYA longer than 27 h i.v. and 40 h s.c. for CTP). These data also show that s.c administration was equal or superior over i.v. administration for both rD'D3-FP variants. $C_{max}$ was higher for rD'D3-CTP as compared to rD'D3-EYA, especially after i.v. administration. $AUC_{0-inf}$ was slightly higher for rD'D3-EYA as compared to rD'D3-CTP after s.c. administration (1094 and 825 μg*h/mL), but there was no major difference after i.v. administration (1669 and 1783 μg*h/mL). These data show that $AUC_{0-inf}$ is higher after i.v. administration, mostly due to the high initial values.

Bioavailability of rD'D3-FP EYA after subcutaneous administration was 66%, and of rD'D3-CTP was 47% (Table 22), and thus in the range of rD'D3-FP in FVIII ko mice (range 40-79%, Table 4).

TABLE 21

Pharmacokinetic parameters of rD'D3-FP EYA and rD'D3-CTP after s.c. or i.v. co-administration of rD'D3-FP EYA and rD'D3-CTP with rVIII-SingleChain in FVIII ko mice

| Treatment | $C_{max}$, extrap. [μg/mL] | Clearance [mL/kg/h] | MRT [h] | Half-life, terminal [h] | $AUC_{0-inf}$ [μg * h/mL] |
|---|---|---|---|---|---|
| 3 mg/kg rD'D3-FP EYA s.c. | 15.7 | 2.7 | 57 | 32 | 1094 |
| 3 mg/kg rD'D3-FP EYA i.v. | 62.8 | 1.8 | 42 | 30 | 1669 |
| 4.29 mg/kg rD'D3-CTP s.c. | 16.5 | 5.2 | 40 | 22 | 825 |
| 4.29 mg/kg rD'D3-CTP i.v. | 144.1 | 2.4 | 27 | 22 | 1783 |

TABLE 22

Bioavailability of rD'D3 variants after s.c. administration in FVIII ko mice calculated against i.v. reference treatments calculated against i.v. reference treatments

| S.c. treatment | Bioavailability [%] to respective i.v. reference treatment with rD'D3 variant |
|---|---|
| 3 mg/kg rD'D3-FP EYA s.c. | 66 |
| 4.29 rD'D3-CTP s.c. | 47 |

Evaluation of FVIII Data

Figure 12:
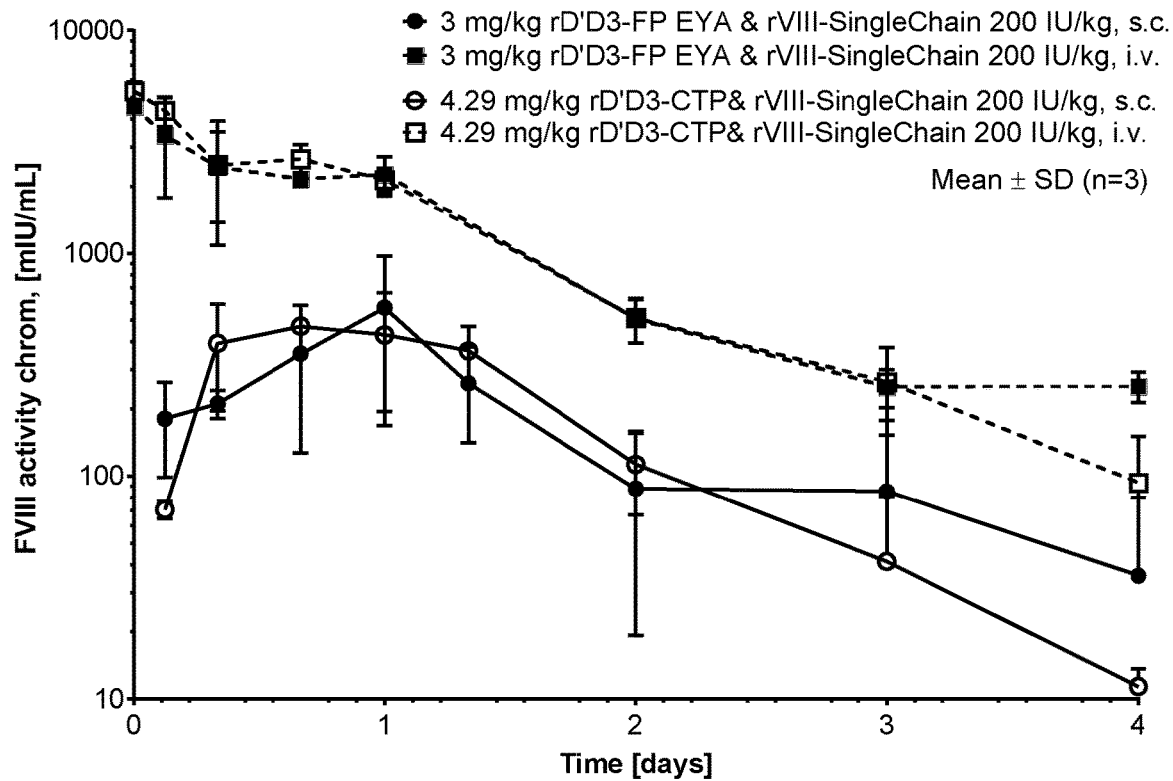
FIG. 12 shows FVIII activity plasma levels after subcutaneous or intravenous administration of rD'D3-FP EYA or rD'D3-CTP with recombinant FVIII in FVIII ko mice. FVIII was quantified as chromogenic FVIII activity. Data is given as mean±SD for n=3 mice per timepoint. Solid lines represent s.c. and dotted lines i.v. treatment; Abbreviation: s.c.: subcutaneous; i.v.: intravenous.

FVIII was absorbed when co-administered s.c. with rD'D3-FP EYA or rD'D3-CTP and FVIII activity endured the absorption process (FIG. 12). FVIII activity was quantified over the whole observation period of 96 h.

Estimation of clearance, MRT, $t_{1/2}$ and $AUC_{0-inf}$ is given in Table 23, showing comparable MRT and $t_{1/2}$ for rD'D3-FP EYA as compared to rD'D3-CTP after s.c. administration (MRT: 27 and 29 h, $t_{1/2}$ 13 and 12 h) and slightly higher MRT and $t_{1/2}$ for rD'D3-FP EYA after i.v. administration (MRT: 30 and 25 h, $t_{1/2}$ 21 and 18 h). No difference was observed for $AUC_{0-inf}$ for the two variants per route of administration (16 and 18 IU*h/mL for s.c. and 111 and 110 IU*h/mL for i.v.). $C_{max}$ was lower for rD'D3-FP EYA compared to rD'D3-CTP after both, i.v. and s.c. administration (0.46 vs. 0.51 IU/mL after s.c. and 4.63 vs. 5.49 after i.v).

Bioavailability of rVIII-SingleChain was 14% for rD'D3-FP EYA and 16% for rD'D3-CTP (Table 24).

Additionally time to trough was calculated for s.c. administration, which showed comparable results for rD'D3-FP EYA and rD'D3-CTP at 1% (105 and 104 h) and 5% (76 and 78 h) trough, and a very slight advantage for rD'D3-FP EYA over rD'D3-CTP at 10% (64 vs. 52 h) trough levels (Table 25). Together, these data demonstrate that the rD'D3 variant is responsible for the improved pharmacokinetics of FVIII, not primarily the type of the half-life extending principle attached to the rD'D3 variant. However, a rD'D3 polypeptide, which does not contain any HELP, is not capable of improving pharmacokinetics of FVIII or at least only with impaired efficacy (see Tables 5 and 7).

TABLE 23

Pharmacokinetic parameters of FVIII antigen after s.c. or i.v. administration of rD'D3-FP EYA or rD'D3-CTP and rVIII-SingleChain in FVIII ko mice

| Treatment | $C_{max}$, extrap. [IU/mL] | Clearance FVIII antigen [mL/kg/h] | MRT [h] | Half-life, terminal [h] | $AUC_{0-inf}$ [IU * h/mL] |
|---|---|---|---|---|---|
| 3 mg/kg rD'D3-FP EYA s.c. | 0.46 | 12.8 | 27 | 13 | 16 |
| 3 mg/kg rD'D3-FP EYA i.v. | 4.63 | 1.8 | 30 | 21 | 111 |
| 4.29 mg/kg rD'D3-CTP s.c. | 0.51 | 11.4 | 29 | 12 | 18 |
| 4.29 mg/kg rD'D3-CTP i.v. | 5.49 | 1.8 | 25 | 18 | 110 |

TABLE 24

Bioavailability of rVIII-SingleChain (FVIII antigen) after s.c. administration in FVIII ko mice calculated against i.v. reference treatments

| S.c. treatment | Bioavailability [%] to respective i.v. reference treatment with rD'D3 variant & 200 IU/kg rVIII-SingleChain |
|---|---|
| 3 mg/kg rD'D3-FP EYA s.c. | 14 |
| 4.29 mg/kg rD'D3-CTP s.c. | 16 |

TABLE 25

Time to trough levels of rVIII-SingleChain (FVIII antigen) after s.c. administration in FVIII ko mice

| Treatment | 1% trough [h] | Time to 5% trough [h] | 10% trough [h] |
|---|---|---|---|
| 3 mg/kg rD'D3-FP EYA s.c. | 105 | 76 | 64 |
| 4.29 mg/kg rD'D3-CTP s.c. | 104 | 78 | 52 |

Conclusion from In Vivo Experiments

The invention demonstrates subcutaneous bioavailability of rD'D3-FP in different species (Table 26), and relevant bioavailability of a recombinant FVIII product, i.e. rVIII-SingleChain, Advate®, ReFacto AF® or Beriate®, when co-administered subcutaneously with rD'D3-FP (Table 27).

TABLE 26

Bioavailability of rD'D3-FP in different species

| Treatment | Bioavailability Mouse, FVIII ko | Pig |
|---|---|---|
| rD'D3-FP alone | 43-50% | 59% |
| rD'D3-FP with FVIII | 40-87% | 70-187% |
| rD'D3-His | 34% | n.d. |
| rD'D3-CTP | 47% | n.d. |
| rD'D3-FP EYA | 66% | n.d. |

TABLE 27

Bioavailability of FVIII in different species

| Treatment | Bioavailability Mouse, FVIII ko | Pig |
|---|---|---|
| rD'D3-FP | 3-25% | 29-40% |
| rD'D3-His | 1% | n.d. |
| rD'D3-CTP | 16% | n.d. |
| rD'D3-FP EYA | 14% | n.d. | n.d.—not determined

In fact, present results demonstrate that subcutaneous administration of rD'D3-FP together with FVIII allows for extravascular administration of a recombinant FVIII product, i.e. rVIII-SingleChain or other FVIII products, e.g. Beriate®, Advate® or ReFacto AF®, associated with unprecedented absorption of FVIII into the bloodstream (bioavailability range from 3-40% with rVIII-SingleChain), resulting in FVIII activity levels significantly above the detection limit. rD'D3-CTP and rD'D3-FP EYA showed roughly comparable data to rD'D3-FP. Said resulting FVIII activity levels are suitable for therapeutic application.

rD'D3-FP or variants thereof are favourable over rD'D3-His, not only for the longer half-life of the rD'D3-FP, increasing maintenance of FVIII in plasma once it reached this compartment, but also for the unproportionally high increase in bioavailability of rVIII-SingleChain, when co-administered with rD'D3-FP or variants thereof as compared to rD'D3-His. This supports that half-life prolongation using albumin or other HLEP is a favourable approach.

Example 2: Determination of FVIII Affinity to VWF Fragment Dimer and Monomer A VWF fragment (1-1242) albumin fusion (D'D3-FP) was expressed in a bioreactor; after purification as described above and isolation of monomer and dimer, the affinity of FVIII to these preparations was assessed through surface plasmon resonance via a Biacore instrument (T200, GE Healthcare).

An anti-albumin antibody (MA1-20124, Thermo Scientific) was covalently coupled via its N-terminus to an activated CM 3 chip by NHS (N-Hydroxysuccinimide) and EDC (Ethanolamine hydrochloride), both contained in the amine coupling kit (BR1000-50) from GE Healthcare. For immobilization 3 µg/mL of the antibody were diluted in sodium acetate buffer (10 mM, pH 5.0) and the antibody solution was flown over the chip for 7 min. at a flow rate of 10 µL/min. After the immobilization procedure non-coupled dextran filaments were saturated by flowing ethanolamine solution (1 M, pH 8.3) over the chip for 5 min (at a flow rate of 10 µL/min). The aim of saturating the flow cell was to minimize unspecific binding of the analytes to the chip. A reference flow cell was set up by saturating an empty flow cell with ethanolamine by using the same procedure as above.

Dimeric and monomeric D'D3-FP proteins, respectively, were immobilized to the covalently coupled anti-albumin antibody by a flow of the D'D3-FP proteins (5 µg/mL) over the chip for 3 min (flow rate of 10 µL/min).

To create binding curves for FVIII, each D'D3-FP protein preparation was diluted in running buffer (HBS-P+: 0.1 M HEPES, 1.5 M NaCl and 0.5% v/v Surfactant P20, pH 7.4; product code BR100671, GE Healthcare) to concentrations of 0.25 nM, 0.5 nM, 1 nM, 3 nM and 4 nM. By performing a single cycle kinetic, samples with ascending concentrations of each dilution were flown over the chip for 2 min (flow rate 30 µL/min.), followed by a dissociation time of 10 min. with running buffer HBS-P+. All measurements were performed twice. The temperature for the measuring procedure was adjusted to +25° C.

Binding parameters were calculated using BiaEvaluation Software. The curve fitting methods were based on Langmuir equations. The input data for calculations were the molar mass of the analyte FVIII (rVIII-SingleChain), other parameters like max. RU and slopes were automatically extracted out of the fitted association and dissociation curves. The outputs of BiaEvaluation Software are the association rate constants and the dissociation rate constants, from which the affinity constants were calculated. The results are shown in Table 28.

TABLE 28 rFVIII-SingleChain affinity data for D'D3-FP dimer and monomer

| D'D3-FP preparation | ka [1/Ms] | kd [1/s] | KD [M] |
|---|---|---|---|
| D'D3-FP Dimer | $4.5 \times 10^7$ | $1.5 \times 10^{-3}$ | $3.4 \times 10^{-11}$ |
| D'D3-FP Monomer | $9.9 \times 10^5$ | $3.0 \times 10^{-2}$ | $3.0 \times 10^{-8}$ |

The dimeric D'D3-FP shows a significantly ($K_D$=34 pM) increased affinity to FVIII compared to the D'D3-FP monomer ($K_D$=30 nM) which results both from a faster association and a slower dissociation of rVIII-SingleChain.

The invention claimed is:

1. A method for the treatment of a blood coagulation disorder, comprising administering an effective amount of (i) a recombinant polypeptide consisting of (a) a truncated von Willebrand Factor (VWF) and (b) at least one non-VWF sequence, and (ii) a Factor VIII protein (FVIII) to a subject having a blood coagulation disorder,
wherein at least one of the non-VWF sequences is a half-life extending moiety (HLEM),
wherein the truncated VWF has a sequence identity of at least 90% to amino acids 764 to 1242 of SEQ ID NO:4,
wherein at least one of the recombinant polypeptide and the FVIII is administered extravascularly,
wherein the recombinant polypeptide is present as a dimer and wherein the ratio of dimer:monomer of the recombinant polypeptide is at least 1.5,
wherein said dimeric recombinant polypeptide is capable of binding to said FVIII and has a FVIII binding affinity characterized by a dissociation constant $K_D$ of less than 1 nM, and
wherein the molar ratio of the recombinant polypeptide to the FVIII is higher than 50.

2. The method of claim 1, wherein the subject is a human subject.

3. The method of claim 1, wherein the dimer binds to FVIII with a dissociation constant $K_D$ of less than 80 pM.

4. The method of claim 1, wherein the recombinant polypeptide is administered subcutaneously, intradermally, or intramuscularly.

5. The method of claim 1, wherein the truncated VWF consists of (a) amino acids 764 to 1242 of SEQ ID NO:4.

6. The method of claim 1, wherein the HLEM is a heterologous amino acid sequence that is fused to the truncated VWF.

7. The method of claim 6, wherein said heterologous amino acid sequence comprises a polypeptide selected from the group consisting of albumin or fragments thereof, transferrin or fragments thereof, the C-terminal peptide of human chorionic gonadotropin, an XTEN sequence, homo-amino acid repeats (HAP), proline-alanine-serine repeats (PAS), afamin, alpha-fetoprotein, Vitamin D binding protein, polypeptides capable of binding under physiological conditions to albumin or to immunoglobulin constant regions, polypeptides capable of binding to the neonatal Fc receptor (FcRn), and combinations thereof.

8. The method of claim 1, wherein the HLEM is conjugated to the recombinant polypeptide.

9. The method of claim 8, wherein said HLEM is selected from the group consisting of hydroxyethyl starch (HES), polyethylene glycol (PEG), polysialic acids (PSAs), elastin-like polypeptides, heparosan polymers, hyaluronic acid, and albumin binding ligands, and combinations thereof.

10. The method of claim 1, wherein the time period for reaching a 1% trough level of the administered FVIII is prolonged compared to a reference treatment in which the FVIII is administered with a recombinant polypeptide that does not comprise said HLEM.

11. The method of claim 1, wherein the plasma half-life of the recombinant polypeptide is increased compared to that of endogenous VWF and/or VWF of normal human plasma (NHP), wherein the plasma half-life of the recombinant polypeptide is at least 100% higher than that of endogenous VWF and/or VWF of normal human plasma (NHP).

12. The method of claim 1, wherein the blood coagulation disorder is hemophilia A or von-Willebrand disease.

13. The method of claim 1, wherein co-administration of the recombinant polypeptide and the FVIII is achieved either (i) by administration of a single composition comprising the recombinant polypeptide and the FVIII, or (ii) by administration of the recombinant polypeptide (first compound) and the FVIII (second compound) each provided in separate compositions, wherein the first compound is administered before, after, or concurrently with the second compound.

14. The method of claim 1, wherein the FVIII is a plasma-derived protein or a recombinant protein.

15. The method of claim 1, wherein the FVIII is administered extravascularly, and wherein, following co-administration of the recombinant polypeptide and the FVIII, the bioavailability of the administered FVIII is at least 2%.

16. The method of claim 1, wherein the bioavailability of the recombinant polypeptide is at least 30%.

17. The method of claim 1, wherein the dosage of the FVIII does not exceed 2500 IU/kg.

18. The method of claim 1, wherein, following co-administration of the recombinant polypeptide and the FVIII, the maximal concentration ($C_{max}$) of the FVIII is at least 10 mIU/mL.

19. The method of claim 1, wherein the molar ratio of the recombinant polypeptide to the FVIII is at least 75.

20. The method of claim 7, wherein polypeptides capable of binding to the neonatal Fc receptor (FcRn) comprise immunoglobulin constant regions and portions thereof.

21. The method of claim 20, wherein the immunoglobulin constant regions and portions thereof comprise the Fc portion of immunoglobulin, and combinations thereof.

22. The method of claim 1, wherein the molar ratio of the recombinant peptide to the FVIII is higher than 100.

23. The method of claim 1, wherein the recombinant polypeptide is administered subcutaneously.

* * * * *

SEQUENCE LISTING

<160> NUMBER OF SEQ ID NOS: 8

<210> SEQ ID NO 1
<211> LENGTH: 5616
<212> TYPE: DNA
<213> ORGANISM: Artificial Sequence
<220> FEATURE:
<223> OTHER INFORMATION: DNA encoding construct VWF fragment - G/S Linker - albumin

```
<220> FEATURE:
<221> NAME/KEY: misc_feature
<222> LOCATION: (1)..(6)
<223> OTHER INFORMATION: EcoRI restriction enzyme cleavage site
<220> FEATURE:
<221> NAME/KEY: misc_feature
<222> LOCATION: (32)..(3757)
<223> OTHER INFORMATION: coding sequence for VWF amino acids 1 to 1242
<220> FEATURE:
<221> NAME/KEY: misc_feature
<222> LOCATION: (3758)..(3850)
<223> OTHER INFORMATION: coding sequence for glycine/serine linker
<220> FEATURE:
<221> NAME/KEY: misc_feature
<222> LOCATION: (3851)..(5608)
<223> OTHER INFORMATION: coding sequence for human albumin
<220> FEATURE:
<221> NAME/KEY: misc_feature
<222> LOCATION: (5609)..(5616)
<223> OTHER INFORMATION: NotI restriction enzyme cleavage site

<400> SEQUENCE: 1
gaattcccgc agccctcatt tgcaggggaa gatgattcct gccagatttg ccggggtgct       60
gcttgctctg gccctcattt tgccagggac cctttgtgca aaggaactc gcggcaggtc      120 atccacggcc cgatgcagcc ttttcggaag tgacttcgtc aacacctttg atgggagcat      180
gtacagcttt gcgggatact gcagttacct cctggcaggg ggctgccaga acgctcctt      240 ctcgattatt ggggacttcc agaatggcaa gagagtgagc ctctccgtgt atcttgggga      300
attttttgac atccatttgt tgtcaatgg taccgtgaca caggggggacc aaagagtctc      360 catgccctat gcctccaaag ggctgtatct agaaactgag gctgggtact acaagctgtc      420
cggtgaggcc tatggctttg tggccaggat cgatggcagc ggcaactttc aagtcctgct      480
gtcagacaga tacttcaaca gacctgcgg gctgtgtggc aactttaaca tctttgctga      540
agatgacttt atgacccaag aagggacctt gacctcggac cctattgact tgccaactc      600 atgggctctg agcagtggag aacagtggtg tgaacgggca tcctctccca gcagctcatg      660
caacatctcc tctggggaaa tgcagaaggg cctgtgggag cagtgccagc ttctgaagag      720
cacctcggtg tttgcccgct gccaccctct ggtggacccc gagccttttg tggccctgtg      780
tgagaagact ttgtgtgagt gtgctggggg gctgagtgc gcctgccctg ccctcctgga      840
gtacgcccgg acctgtgccc aggagggaat ggtgctgtac ggctggaccg accacagcgc      900
gtgcagccca gtgtgccctg ctggtatgga gtataggcag tgtgtgtccc cttgcgccag      960
gacctgccag agcctgcaca tcaatgaaat gtgtcaggag cgatgcgtgg atggctgcag     1020 ctgcccctgag ggacagctcc tggatgaagg cctctgcgtg gagagcaccg agtgtccctg     1080
cgtgcattcc ggaaagcgct accctcccgg cacctcccctc tctcgagact gcaacacctg     1140
catttgccga aacagccagt ggatctgcag caatgaagaa tgtccagggg agtgccttgt     1200
cacaggtcaa tcacacttca agagctttga caacagatac ttcaccttca gtgggatctg     1260
ccagtacctg ctgccccggg attgccagga ccactccttc tccattgtca ttgagactgt     1320
ccagtgtgct gatgaccgcg acgctgtgtg cacccgctcc gtcaccgtcc ggctgcctgg     1380
cctgcacaac agccttgtga aactgaagca tggggcagga gttgccatgg atggccagga     1440
cgtccagctc ccctcctga aggtgacct ccgcatccag catacagtga cggcctccgt     1500
gcgcctcagc tacggggagg acctgcagat ggactggat ggccgcggga ggctgctggt     1560
gaagctgtcc cccgtctatg ccgggaagac ctgcggcctg tgtgggaatt acaatggcaa     1620
ccagggcgac gacttcctta ccccctctgg gctggcggag cccggggtgg aggacttcgg     1680
```

```
gaacgcctgg aagctgcacg gggactgcca ggacctgcag aagcagcaca gcgatccctg    1740
cgccctcaac ccgcgcatga ccaggttctc cgaggaggcg tgcgcggtcc tgacgtcccc    1800
cacattcgag gcctgccatc gtgccgtcag cccgctgccc tacctgcgga actgccgcta    1860
cgacgtgtgc tcctgctcgg acggccgcga gtgcctgtgc ggcgccctgg ccagctatgc    1920
cgcggcctgc gcggggagag gcgtgcgcgt cgcgtggcgc gagccaggcc gctgtgagct    1980
gaactgcccg aaaggccagg tgtacctgca gtgcgggacc ccctgcaacc tgacctgccg    2040
ctctctctct tacccggatg aggaatgcaa tgaggcctgc ctggagggct gcttctgccc    2100
cccagggctc tacatggatg agagggggga ctgcgtgccc aaggcccagt gcccctgtta    2160
ctatgacggt gagatcttcc agccagaaga catcttctca gaccatcaca ccatgtgcta    2220
ctgtgaggat ggcttcatgc actgtaccat gagtggagtc cccggaagct gctgcctga    2280 cgctgtcctc agcagtcccc tgtctcatcg cagcaaaagg agcctatcct gtcggccccc    2340
catggtcaag ctggtgtgtc ccgctgacaa cctgcgggct gaagggctcg agtgtaccaa    2400
aacgtgccag aactatgacc tggagtgcat gagcatgggc tgtgtctctg ctgcctctg    2460 cccccccggc atggtccggc atgagaacag atgtgtggcc ctggaaaggt gtccctgctt    2520
ccatcagggc aaggagtatg cccctggaga acagtgaag attggctgca acacttgtgt    2580
ctgtcgggac cggaagtgga actgcacaga ccatgtgtgt gatgccacgt gctccacgat    2640
cggcatggcc cactacctca ccttcgacgg gctcaaatac ctgttccccg ggagtgcca    2700 gtacgttctg gtgcaggatt actgcggcag taaccctggg acctttcgga tcctagtggg    2760
gaataaggga tgcagccacc cctcagtgaa atgcaagaaa cgggtcacca tcctggtgga    2820
gggaggagag attgagctgt ttgacgggga ggtgaatgtg aagaggccca tgaaggatga    2880
gactcacttt gaggtggtgg agtctggccg gtacatcatt ctgctgctgg gcaaagccct    2940
ctccgtggtc tgggaccgcc acctgagcat ctccgtggtc ctgaagcaga cataccagga    3000
gaaagtgtgt ggcctgtgtg ggaattttga tggcatccag aacaatgacc tcaccagcag    3060
caacctccaa gtggaggaag accctgtgga ctttgggaac tcctggaaag tgagctcgca    3120
gtgtgctgac accagaaaag tgcctctgga ctcatcccct gccacctgcc ataacaacat    3180
catgaagcag acgatggtgg attcctcctg tagaatcctt accagtgacg tcttccagga    3240
ctgcaacaag ctggtggacc ccgagccata tctggatgtc tgcatttacg acacctgctc    3300
ctgtgagtcc attggggact cgcctgcttt ctgcgacacc attgctgcct atgcccacgt    3360
gtgtgcccag catggcaagg tggtgacctg gaggacggcc acattgtgcc cccagagctg    3420
cgaggagagg aatctccggg agaacgggta tgagtgtgag tggcgctata acagctgtgc    3480
acctgcctgt caagtcacgt gtcagcaccc tgagccactg gcctgccctg tgcagtgtgt    3540
ggagggctgc catgcccact gccctccagg gaaaatcctg gatgagcttt tgcagacctg    3600
cgttgaccct gaagactgtc cagtgtgtga ggtggctggc cggcgttttg cctcaggaaa    3660
gaaagtcacc ttgaatccca gtgaccctga gcactgccag atttgccact gtgatgttgt    3720
caacctcacc tgtgaagcct gccaggagcc gggaggctcg agcggggat ctggcgggtc    3780 tggaggctct ggagggtcgg gaggctctgg aggctctggg ggatctggcg ggtctggagg    3840
gtcgggatcc gatgcacaca agagtgaggt tgctcatcgg tttaaagatt ggggagaaga    3900
aaatttcaaa gccttggtgt tgattgcctt tgctcagtat cttcagcagt gtccatttga    3960
agatcatgta aaattagtga atgaagtaac tgaatttgca aaaacatgtg ttgctgatga    4020
gtcagctgaa aattgtgaca aatcacttca taccctttt ggagacaaat tatgcacagt    4080
```

| | | |
|---|---|---|
| tgcaactctt cgtgaaacct atggtgaaat ggctgactgc tgtgcaaaac aagaacctga | 4140 |
| gagaaatgaa tgcttcttgc aacacaaaga tgacaaccca aacctccccc gattggtgag | 4200 |
| accagaggtt gatgtgatgt gcactgcttt tcatgacaat gaagagacat ttttgaaaaa | 4260 |
| atacttatat gaaattgcca gaagacatcc ttactttttat gccccggaac tccttttctt | 4320 |
| tgctaaaagg tataaagctg cttttacaga atgttgccaa gctgctgata aagctgcctg | 4380 |
| cctgttgcca aagctcgatg aacttcggga tgaagggaag gcttcgtctg ccaaacagag | 4440 |
| actcaagtgt gccagtctcc aaaaatttgg agaaagagct ttcaaagcat gggcagtagc | 4500 |
| tcgcctgagc cagagatttc ccaaagctga gtttgcagaa gtttccaagt tagtgacaga | 4560 |
| tcttaccaaa gtccacacgg aatgctgcca tggagatctg cttgaatgtg ctgatgacag | 4620 |
| ggcggacctt gccaagtata tctgtgaaaa tcaagattcg atctccagta aactgaagga | 4680 |
| atgctgtgaa aaacctctgt ggaaaaaatc ccactgcatt gccgaagtgg aaaatgatga | 4740 |
| gatgcctgct gacttgcctt cattagctgc tgattttgtt gaaagtaagg atgtttgcaa | 4800 |
| aaactatgct gaggcaaagg atgtcttcct gggcatgttt ttgtatgaat atgcaagaag | 4860 |
| gcatcctgat tactctgtcg tgctgctgct gagacttgcc aagacatatg aaaccactct | 4920 |
| agagaagtgc tgtgccgctg cagatcctca tgaatgctat gccaaagtgt tcgatgaatt | 4980 |
| taaacctctt gtggaagagc ctcagaattt aatcaaacaa aattgtgagc ttttgagca | 5040 |
| gcttggagag tacaaattcc agaatgcgct attagttcgt tacaccaaga agtaccccca | 5100 |
| agtgtcaact ccaactcttg tagaggtctc aagaaaccta ggaaagtgg gcagcaaatg | 5160 |
| ttgtaaacat cctgaagcaa aaagaatgcc ctgtgcagaa gactatctat ccgtggtcct | 5220 |
| gaaccagtta tgtgtgttgc atgagaaaac gccagtaagt gacagagtca ccaaatgctg | 5280 |
| cacagaatcc ttggtgaaca ggcgaccatg ctttcagct ctggaagtcg atgaaacata | 5340 |
| cgttcccaaa gagtttaatg ctgaaacatt caccttccat gcagatatat gcacactttc | 5400 |
| tgagaaggag agacaaatca gaaacaaac tgcacttgtt gagctcgtga acacaagcc | 5460 |
| caaggcaaca aaagagcaac tgaaagctgt tatggatgat ttcgcagctt ttgtagagaa | 5520 |
| gtgctgcaag gctgacgata aggagacctg ctttgccgag gagggtaaaa aacttgttgc | 5580 |
| tgcaagtcaa gctgccttag gcttataggc ggccgc | 5616 |

<210> SEQ ID NO 2
<211> LENGTH: 1095
<212> TYPE: PRT
<213> ORGANISM: Artificial Sequence
<220> FEATURE:
<223> OTHER INFORMATION: polypeptide encoded by SEQ ID NO:1
<220> FEATURE:
<221> NAME/KEY: MISC_FEATURE
<222> LOCATION: (1)..(479)
<223> OTHER INFORMATION: VWF D'D3 region (VWF amino acids 764 - 1242)
<220> FEATURE:
<221> NAME/KEY: MISC_FEATURE
<222> LOCATION: (480)..(510)
<223> OTHER INFORMATION: glycine/serine linker
<220> FEATURE:
<221> NAME/KEY: MISC_FEATURE
<222> LOCATION: (511)..(1095)
<223> OTHER INFORMATION: human albumin

<400> SEQUENCE: 2

Ser Leu Ser Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
            20                  25                  30

-continued

```
Asp Leu Glu Cys Met Ser Met Gly Cys Val Ser Gly Cys Leu Cys Pro
             35                  40                  45

Pro Gly Met Val Arg His Glu Asn Arg Cys Val Ala Leu Glu Arg Cys
 50                  55                  60

Pro Cys Phe His Gln Gly Lys Glu Tyr Ala Pro Gly Glu Thr Val Lys
 65                  70                  75                  80

Ile Gly Cys Asn Thr Cys Val Cys Arg Asp Arg Lys Trp Asn Cys Thr
                 85                  90                  95

Asp His Val Cys Asp Ala Thr Cys Ser Thr Ile Gly Met Ala His Tyr
                100                 105                 110

Leu Thr Phe Asp Gly Leu Lys Tyr Leu Phe Pro Gly Glu Cys Gln Tyr
            115                 120                 125

Val Leu Val Gln Asp Tyr Cys Gly Ser Asn Pro Gly Thr Phe Arg Ile
130                 135                 140

Leu Val Gly Asn Lys Gly Cys Ser His Pro Ser Val Lys Cys Lys Lys
145                 150                 155                 160

Arg Val Thr Ile Leu Val Glu Gly Gly Glu Ile Glu Leu Phe Asp Gly
                165                 170                 175

Glu Val Asn Val Lys Arg Pro Met Lys Asp Glu Thr His Phe Glu Val
            180                 185                 190

Val Glu Ser Gly Arg Tyr Ile Ile Leu Leu Leu Gly Lys Ala Leu Ser
            195                 200                 205

Val Val Trp Asp Arg His Leu Ser Ile Ser Val Leu Lys Gln Thr
            210                 215                 220

Tyr Gln Glu Lys Val Cys Gly Leu Cys Gly Asn Phe Asp Gly Ile Gln
225                 230                 235                 240

Asn Asn Asp Leu Thr Ser Ser Asn Leu Gln Val Glu Glu Asp Pro Val
                245                 250                 255

Asp Phe Gly Asn Ser Trp Lys Val Ser Ser Gln Cys Ala Asp Thr Arg
            260                 265                 270

Lys Val Pro Leu Asp Ser Ser Pro Ala Thr Cys His Asn Asn Ile Met
            275                 280                 285

Lys Gln Thr Met Val Asp Ser Ser Cys Arg Ile Leu Thr Ser Asp Val
            290                 295                 300

Phe Gln Asp Cys Asn Lys Leu Val Asp Pro Glu Pro Tyr Leu Asp Val
305                 310                 315                 320

Cys Ile Tyr Asp Thr Cys Ser Cys Glu Ser Ile Gly Asp Cys Ala Cys
                325                 330                 335

Phe Cys Asp Thr Ile Ala Ala Tyr Ala His Val Cys Ala Gln His Gly
            340                 345                 350

Lys Val Val Thr Trp Arg Thr Ala Thr Leu Cys Pro Gln Ser Cys Glu
            355                 360                 365

Glu Arg Asn Leu Arg Glu Asn Gly Tyr Glu Cys Glu Trp Arg Tyr Asn
            370                 375                 380

Ser Cys Ala Pro Ala Cys Gln Val Thr Cys Gln His Pro Glu Pro Leu
385                 390                 395                 400

Ala Cys Pro Val Gln Cys Val Glu Gly Cys His Ala His Cys Pro Pro
                405                 410                 415

Gly Lys Ile Leu Asp Glu Leu Leu Gln Thr Cys Val Asp Pro Glu Asp
            420                 425                 430

Cys Pro Val Cys Glu Val Ala Gly Arg Arg Phe Ala Ser Gly Lys Lys
            435                 440                 445
```

```
Val Thr Leu Asn Pro Ser Asp Pro Glu His Cys Gln Ile Cys His Cys
450                 455                 460
Asp Val Val Asn Leu Thr Cys Glu Ala Cys Gln Glu Pro Gly Gly Ser
465                 470                 475                 480
Ser Gly Gly Ser Gly Gly Ser Gly Gly Ser Gly Ser Gly Gly Ser
            485                 490                 495
Gly Gly Ser Gly Gly Ser Gly Gly Ser Gly Ser Gly Ser Asp Ala
            500                 505                 510
His Lys Ser Glu Val Ala His Arg Phe Lys Asp Leu Gly Glu Glu Asn
            515                 520                 525
Phe Lys Ala Leu Val Leu Ile Ala Phe Ala Gln Tyr Leu Gln Gln Cys
530                 535                 540
Pro Phe Glu Asp His Val Lys Leu Val Asn Glu Val Thr Glu Phe Ala
545                 550                 555                 560
Lys Thr Cys Val Ala Asp Glu Ser Ala Glu Asn Cys Asp Lys Ser Leu
                565                 570                 575
His Thr Leu Phe Gly Asp Lys Leu Cys Thr Val Ala Thr Leu Arg Glu
            580                 585                 590
Thr Tyr Gly Glu Met Ala Asp Cys Cys Ala Lys Gln Glu Pro Glu Arg
            595                 600                 605
Asn Glu Cys Phe Leu Gln His Lys Asp Asp Asn Pro Asn Leu Pro Arg
610                 615                 620
Leu Val Arg Pro Glu Val Asp Val Met Cys Thr Ala Phe His Asp Asn
625                 630                 635                 640
Glu Glu Thr Phe Leu Lys Lys Tyr Leu Tyr Glu Ile Ala Arg Arg His
                645                 650                 655
Pro Tyr Phe Tyr Ala Pro Glu Leu Leu Phe Phe Ala Lys Arg Tyr Lys
            660                 665                 670
Ala Ala Phe Thr Glu Cys Cys Gln Ala Ala Asp Lys Ala Ala Cys Leu
            675                 680                 685
Leu Pro Lys Leu Asp Glu Leu Arg Asp Glu Gly Lys Ala Ser Ser Ala
690                 695                 700
Lys Gln Arg Leu Lys Cys Ala Ser Leu Gln Lys Phe Gly Glu Arg Ala
705                 710                 715                 720
Phe Lys Ala Trp Ala Val Ala Arg Leu Ser Gln Arg Phe Pro Lys Ala
                725                 730                 735
Glu Phe Ala Glu Val Ser Lys Leu Val Thr Asp Leu Thr Lys Val His
            740                 745                 750
Thr Glu Cys Cys His Gly Asp Leu Leu Glu Cys Ala Asp Asp Arg Ala
            755                 760                 765
Asp Leu Ala Lys Tyr Ile Cys Glu Asn Gln Asp Ser Ile Ser Ser Lys
            770                 775                 780
Leu Lys Glu Cys Cys Glu Lys Pro Leu Leu Glu Lys Ser His Cys Ile
785                 790                 795                 800
Ala Glu Val Glu Asn Asp Glu Met Pro Ala Asp Leu Pro Ser Leu Ala
                805                 810                 815
Ala Asp Phe Val Glu Ser Lys Asp Val Cys Lys Asn Tyr Ala Glu Ala
            820                 825                 830
Lys Asp Val Phe Leu Gly Met Phe Leu Tyr Glu Tyr Ala Arg Arg His
            835                 840                 845
Pro Asp Tyr Ser Val Val Leu Leu Leu Arg Leu Ala Lys Thr Tyr Glu
850                 855                 860
```

| | | | | | | | | | | | | |
|---|---|---|---|---|---|---|---|---|---|---|---|---|
|Thr|Thr|Leu|Glu|Lys|Cys|Cys|Ala|Ala|Ala|Asp|Pro|His|Glu|Cys|Tyr|
|865| | | |870| | | |875| | | |880| | | |

Ala Lys Val Phe Asp Glu Phe Lys Pro Leu Val Glu Glu Pro Gln Asn
                885                 890                 895

Leu Ile Lys Gln Asn Cys Glu Leu Phe Glu Gln Leu Gly Glu Tyr Lys
        900                 905                 910

Phe Gln Asn Ala Leu Leu Val Arg Tyr Thr Lys Lys Val Pro Gln Val
            915                 920                 925

Ser Thr Pro Thr Leu Val Glu Val Ser Arg Asn Leu Gly Lys Val Gly
        930                 935                 940

Ser Lys Cys Cys Lys His Pro Glu Ala Lys Arg Met Pro Cys Ala Glu
945                 950                 955                 960

Asp Tyr Leu Ser Val Val Leu Asn Gln Leu Cys Val Leu His Glu Lys
            965                 970                 975

Thr Pro Val Ser Asp Arg Val Thr Lys Cys Cys Thr Glu Ser Leu Val
        980                 985                 990

Asn Arg Arg Pro Cys Phe Ser Ala Leu Glu Val Asp Glu Thr Tyr Val
            995                 1000                1005

Pro Lys Glu Phe Asn Ala Glu Thr Phe Thr Phe His Ala Asp Ile
    1010                1015                1020

Cys Thr Leu Ser Glu Lys Glu Arg Gln Ile Lys Lys Gln Thr Ala
    1025                1030                1035

Leu Val Glu Leu Val Lys His Lys Pro Lys Ala Thr Lys Glu Gln
    1040                1045                1050

Leu Lys Ala Val Met Asp Asp Phe Ala Ala Phe Val Glu Lys Cys
    1055                1060                1065

Cys Lys Ala Asp Asp Lys Glu Thr Cys Phe Ala Glu Glu Gly Lys
    1070                1075                1080

Lys Leu Val Ala Ala Ser Gln Ala Ala Leu Gly Leu
    1085                1090                1095

<210> SEQ ID NO 3
<211> LENGTH: 8442
<212> TYPE: DNA
<213> ORGANISM: Homo sapiens
<220> FEATURE:
<221> NAME/KEY: CDS
<222> LOCATION: (1)..(8442)

<400> SEQUENCE: 3

```
atg att cct gcc aga ttt gcc ggg gtg ctg ctt gct ctg gcc ctc att     48
Met Ile Pro Ala Arg Phe Ala Gly Val Leu Leu Ala Leu Ala Leu Ile
1               5                   10                  15 ttg cca ggg acc ctt tgt gca gaa gga act cgc ggc agg tca tcc acg     96
Leu Pro Gly Thr Leu Cys Ala Glu Gly Thr Arg Gly Arg Ser Ser Thr
            20                  25                  30 gcc cga tgc agc ctt ttc gga agt gac ttc gtc aac acc ttt gat ggg    144
Ala Arg Cys Ser Leu Phe Gly Ser Asp Phe Val Asn Thr Phe Asp Gly
        35                  40                  45 agc atg tac agc ttt gcg gga tac tgc agt tac ctc ctg gca ggg ggc    192
Ser Met Tyr Ser Phe Ala Gly Tyr Cys Ser Tyr Leu Leu Ala Gly Gly
    50                  55                  60 tgc cag aaa cgc tcc ttc tcg att att ggg gac ttc cag aat ggc aag    240
Cys Gln Lys Arg Ser Phe Ser Ile Ile Gly Asp Phe Gln Asn Gly Lys
65                  70                  75                  80 aga gtg agc ctc tcc gtg tat ctt ggg gaa ttt ttt gac atc cat ttg    288
Arg Val Ser Leu Ser Val Tyr Leu Gly Glu Phe Phe Asp Ile His Leu
                85                  90                  95
```

|     |     |     |     |     |     |     |     |     |     |     |     |     |     |     |     |     |
|---|---|---|---|---|---|---|---|---|---|---|---|---|---|---|---|---|
| ttt | gtc | aat | ggt | acc | gtg | aca | cag | ggg | gac | caa | aga | gtc | tcc | atg | ccc | 336 |
| Phe | Val | Asn | Gly | Thr | Val | Thr | Gln | Gly | Asp | Gln | Arg | Val | Ser | Met | Pro | |
| | | | 100 | | | | 105 | | | | | 110 | | | | |
| tat | gcc | tcc | aaa | ggg | ctg | tat | cta | gaa | act | gag | gct | ggg | tac | tac | aag | 384 |
| Tyr | Ala | Ser | Lys | Gly | Leu | Tyr | Leu | Glu | Thr | Glu | Ala | Gly | Tyr | Tyr | Lys | |
| | | 115 | | | | 120 | | | | | 125 | | | | | |
| ctg | tcc | ggt | gag | gcc | tat | ggc | ttt | gtg | gcc | agg | atc | gat | ggc | agc | ggc | 432 |
| Leu | Ser | Gly | Glu | Ala | Tyr | Gly | Phe | Val | Ala | Arg | Ile | Asp | Gly | Ser | Gly | |
| 130 | | | | | 135 | | | | | 140 | | | | | | |
| aac | ttt | caa | gtc | ctg | ctg | tca | gac | aga | tac | ttc | aac | aag | acc | tgc | ggg | 480 |
| Asn | Phe | Gln | Val | Leu | Leu | Ser | Asp | Arg | Tyr | Phe | Asn | Lys | Thr | Cys | Gly | |
| 145 | | | | 150 | | | | | 155 | | | | | 160 | | |
| ctg | tgt | ggc | aac | ttt | aac | atc | ttt | gct | gaa | gat | gac | ttt | atg | acc | caa | 528 |
| Leu | Cys | Gly | Asn | Phe | Asn | Ile | Phe | Ala | Glu | Asp | Asp | Phe | Met | Thr | Gln | |
| | | | 165 | | | | 170 | | | | | 175 | | | | |
| gaa | ggg | acc | ttg | acc | tcg | gac | cct | tat | gac | ttt | gcc | aac | tca | tgg | gct | 576 |
| Glu | Gly | Thr | Leu | Thr | Ser | Asp | Pro | Tyr | Asp | Phe | Ala | Asn | Ser | Trp | Ala | |
| | | | 180 | | | | 185 | | | | | 190 | | | | |
| ctg | agc | agt | gga | gaa | cag | tgg | tgt | gaa | cgg | gca | tct | cct | ccc | agc | agc | 624 |
| Leu | Ser | Ser | Gly | Glu | Gln | Trp | Cys | Glu | Arg | Ala | Ser | Pro | Pro | Ser | Ser | |
| | | 195 | | | | 200 | | | | | 205 | | | | | |
| tca | tgc | aac | atc | tcc | tct | ggg | gaa | atg | cag | aag | ggc | ctg | tgg | gag | cag | 672 |
| Ser | Cys | Asn | Ile | Ser | Ser | Gly | Glu | Met | Gln | Lys | Gly | Leu | Trp | Glu | Gln | |
| 210 | | | | 215 | | | | | 220 | | | | | | | |
| tgc | cag | ctt | ctg | aag | agc | acc | tcg | gtg | ttt | gcc | cgc | tgc | cac | cct | ctg | 720 |
| Cys | Gln | Leu | Leu | Lys | Ser | Thr | Ser | Val | Phe | Ala | Arg | Cys | His | Pro | Leu | |
| 225 | | | | 230 | | | | | 235 | | | | | 240 | | |
| gtg | gac | ccc | gag | cct | ttt | gtg | gcc | ctg | tgt | gag | aag | act | ttg | tgt | gag | 768 |
| Val | Asp | Pro | Glu | Pro | Phe | Val | Ala | Leu | Cys | Glu | Lys | Thr | Leu | Cys | Glu | |
| | | | 245 | | | | 250 | | | | | 255 | | | | |
| tgt | gct | ggg | ggg | ctg | gag | tgc | gcc | tgc | cct | gcc | ctc | ctg | gag | tac | gcc | 816 |
| Cys | Ala | Gly | Gly | Leu | Glu | Cys | Ala | Cys | Pro | Ala | Leu | Leu | Glu | Tyr | Ala | |
| | | | 260 | | | | 265 | | | | | 270 | | | | |
| cgg | acc | tgt | gcc | cag | gag | gga | atg | gtg | ctg | tac | ggc | tgg | acc | gac | cac | 864 |
| Arg | Thr | Cys | Ala | Gln | Glu | Gly | Met | Val | Leu | Tyr | Gly | Trp | Thr | Asp | His | |
| | | 275 | | | | 280 | | | | | 285 | | | | | |
| agc | gcg | tgc | agc | cca | gtg | tgc | cct | gct | ggt | atg | gag | tat | agg | cag | tgt | 912 |
| Ser | Ala | Cys | Ser | Pro | Val | Cys | Pro | Ala | Gly | Met | Glu | Tyr | Arg | Gln | Cys | |
| 290 | | | | 295 | | | | | 300 | | | | | | | |
| gtg | tcc | cct | tgc | gcc | agg | acc | tgc | cag | agc | ctg | cac | atc | aat | gaa | atg | 960 |
| Val | Ser | Pro | Cys | Ala | Arg | Thr | Cys | Gln | Ser | Leu | His | Ile | Asn | Glu | Met | |
| 305 | | | | 310 | | | | | 315 | | | | | 320 | | |
| tgt | cag | gag | cga | tgc | gtg | gat | ggc | tgc | agc | tgc | cct | gag | gga | cag | ctc | 1008 |
| Cys | Gln | Glu | Arg | Cys | Val | Asp | Gly | Cys | Ser | Cys | Pro | Glu | Gly | Gln | Leu | |
| | | | 325 | | | | 330 | | | | | 335 | | | | |
| ctg | gat | gaa | ggc | ctc | tgc | gtg | gag | agc | acc | gag | tgt | ccc | tgc | gtg | cat | 1056 |
| Leu | Asp | Glu | Gly | Leu | Cys | Val | Glu | Ser | Thr | Glu | Cys | Pro | Cys | Val | His | |
| | | | 340 | | | | 345 | | | | | 350 | | | | |
| tcc | gga | aag | cgc | tac | cct | ccc | ggc | acc | tcc | ctc | tct | cga | gac | tgc | aac | 1104 |
| Ser | Gly | Lys | Arg | Tyr | Pro | Pro | Gly | Thr | Ser | Leu | Ser | Arg | Asp | Cys | Asn | |
| | | 355 | | | | 360 | | | | | 365 | | | | | |
| acc | tgc | att | tgc | cga | aac | agc | cag | tgg | atc | tgc | agc | aat | gaa | gaa | tgt | 1152 |
| Thr | Cys | Ile | Cys | Arg | Asn | Ser | Gln | Trp | Ile | Cys | Ser | Asn | Glu | Glu | Cys | |
| 370 | | | | 375 | | | | | 380 | | | | | | | |
| cca | ggg | gag | tgc | ctt | gtc | aca | ggt | caa | tca | cac | ttc | aag | agc | ttt | gac | 1200 |
| Pro | Gly | Glu | Cys | Leu | Val | Thr | Gly | Gln | Ser | His | Phe | Lys | Ser | Phe | Asp | |
| 385 | | | | 390 | | | | | 395 | | | | | 400 | | |
| aac | aga | tac | ttc | acc | ttc | agt | ggg | atc | tgc | cag | tac | ctg | ctg | gcc | cgg | 1248 |
| Asn | Arg | Tyr | Phe | Thr | Phe | Ser | Gly | Ile | Cys | Gln | Tyr | Leu | Leu | Ala | Arg | |
| | | | 405 | | | | 410 | | | | | 415 | | | | |

-continued

| | |
|---|---|
| gat tgc cag gac cac tcc ttc tcc att gtc att gag act gtc cag tgt<br>Asp Cys Gln Asp His Ser Phe Ser Ile Val Ile Glu Thr Val Gln Cys<br>420            425             430 | 1296 |
| gct gat gac cgc gac gct gtg tgc acc cgc tcc gtc acc gtc cgg ctg<br>Ala Asp Asp Arg Asp Ala Val Cys Thr Arg Ser Val Thr Val Arg Leu<br>435            440             445 | 1344 |
| cct ggc ctg cac aac agc ctt gtg aaa ctg aag cat ggg gca gga gtt<br>Pro Gly Leu His Asn Ser Leu Val Lys Leu Lys His Gly Ala Gly Val<br>450            455             460 | 1392 |
| gcc atg gat ggc cag gac gtc cag ctc ccc ctc ctg aaa ggt gac ctc<br>Ala Met Asp Gly Gln Asp Val Gln Leu Pro Leu Leu Lys Gly Asp Leu<br>465            470             475             480 | 1440 |
| cgc atc cag cat aca gtg acg gcc tcc gtg cgc ctc agc tac ggg gag<br>Arg Ile Gln His Thr Val Thr Ala Ser Val Arg Leu Ser Tyr Gly Glu<br>485            490             495 | 1488 |
| gac ctg cag atg gac tgg gat ggc cgc ggg agg ctg ctg gtg aag ctg<br>Asp Leu Gln Met Asp Trp Asp Gly Arg Gly Arg Leu Leu Val Lys Leu<br>500            505             510 | 1536 |
| tcc ccc gtc tat gcc ggg aag acc tgc ggc ctg tgt ggg aat tac aat<br>Ser Pro Val Tyr Ala Gly Lys Thr Cys Gly Leu Cys Gly Asn Tyr Asn<br>515            520             525 | 1584 |
| ggc aac cag ggc gac gac ttc ctt acc ccc tct ggg ctg gcg gag ccc<br>Gly Asn Gln Gly Asp Asp Phe Leu Thr Pro Ser Gly Leu Ala Glu Pro<br>530            535             540 | 1632 |
| cgg gtg gag gac ttc ggg aac gcc tgg aag ctg cac ggg gac tgc cag<br>Arg Val Glu Asp Phe Gly Asn Ala Trp Lys Leu His Gly Asp Cys Gln<br>545            550             555             560 | 1680 |
| gac ctg cag aag cag cac agc gat ccc tgc gcc ctc aac ccg cgc atg<br>Asp Leu Gln Lys Gln His Ser Asp Pro Cys Ala Leu Asn Pro Arg Met<br>565            570             575 | 1728 |
| acc agg ttc tcc gag gag gcg tgc gcg gtc ctg acg tcc ccc aca ttc<br>Thr Arg Phe Ser Glu Glu Ala Cys Ala Val Leu Thr Ser Pro Thr Phe<br>580            585             590 | 1776 |
| gag gcc tgc cat cgt gcc gtc agc ccg ctg ccc tac ctg cgg aac tgc<br>Glu Ala Cys His Arg Ala Val Ser Pro Leu Pro Tyr Leu Arg Asn Cys<br>595            600             605 | 1824 |
| cgc tac gac gtg tgc tcc tgc tcg gac ggc cgc gag tgc ctg tgc ggc<br>Arg Tyr Asp Val Cys Ser Cys Ser Asp Gly Arg Glu Cys Leu Cys Gly<br>610            615             620 | 1872 |
| gcc ctg gcc agc tat gcc gcg gcc tgc gcg ggg aga ggc gtg cgc gtc<br>Ala Leu Ala Ser Tyr Ala Ala Ala Cys Ala Gly Arg Gly Val Arg Val<br>625            630             635             640 | 1920 |
| gcg tgg cgc gag cca ggc cgc tgt gag ctg aac tgc ccg aaa ggc cag<br>Ala Trp Arg Glu Pro Gly Arg Cys Glu Leu Asn Cys Pro Lys Gly Gln<br>645            650             655 | 1968 |
| gtg tac ctg cag tgc ggg acc ccc tgc aac ctg acc tgc cgc tct ctc<br>Val Tyr Leu Gln Cys Gly Thr Pro Cys Asn Leu Thr Cys Arg Ser Leu<br>660            665             670 | 2016 |
| tct tac ccg gat gag gaa tgc aat gag gcc tgc ctg gag ggc tgc ttc<br>Ser Tyr Pro Asp Glu Glu Cys Asn Glu Ala Cys Leu Glu Gly Cys Phe<br>675            680             685 | 2064 |
| tgc ccc cca ggg ctc tac atg gat gag agg ggg gac tgc gtg ccc aag<br>Cys Pro Pro Gly Leu Tyr Met Asp Glu Arg Gly Asp Cys Val Pro Lys<br>690            695             700 | 2112 |
| gcc cag tgc ccc tgt tac tat gac ggt gag atc ttc cag cca gaa gac<br>Ala Gln Cys Pro Cys Tyr Tyr Asp Gly Glu Ile Phe Gln Pro Glu Asp<br>705            710             715             720 | 2160 |
| atc ttc tca gac cat cac acc atg tgc tac tgt gag gat ggc ttc atg<br>Ile Phe Ser Asp His His Thr Met Cys Tyr Cys Glu Asp Gly Phe Met<br>725            730             735 | 2208 |

```
                                           -continued cac tgt acc atg agt gga gtc ccc gga agc ttg ctg cct gac gct gtc    2256
His Cys Thr Met Ser Gly Val Pro Gly Ser Leu Leu Pro Asp Ala Val
            740             745             750 ctc agc agt ccc ctg tct cat cgc agc aaa agg agc cta tcc tgt cgg    2304
Leu Ser Ser Pro Leu Ser His Arg Ser Lys Arg Ser Leu Ser Cys Arg
        755             760             765 ccc ccc atg gtc aag ctg gtg tgt ccc gct gac aac ctg cgg gct gaa    2352
Pro Pro Met Val Lys Leu Val Cys Pro Ala Asp Asn Leu Arg Ala Glu
    770             775             780 ggg ctc gag tgt acc aaa acg tgc cag aac tat gac ctg gag tgc atg    2400
Gly Leu Glu Cys Thr Lys Thr Cys Gln Asn Tyr Asp Leu Glu Cys Met
785             790             795             800 agc atg ggc tgt gtc tct ggc tgc ctc tgc ccc ccg ggc atg gtc cgg    2448
Ser Met Gly Cys Val Ser Gly Cys Leu Cys Pro Pro Gly Met Val Arg
            805             810             815 cat gag aac aga tgt gtg gcc ctg gaa agg tgt ccc tgc ttc cat cag    2496
His Glu Asn Arg Cys Val Ala Leu Glu Arg Cys Pro Cys Phe His Gln
        820             825             830 ggc aag gag tat gcc cct gga gaa aca gtg aag att ggc tgc aac act    2544
Gly Lys Glu Tyr Ala Pro Gly Glu Thr Val Lys Ile Gly Cys Asn Thr
    835             840             845 tgt gtc tgt cgg gac cgg aag tgg aac tgc aca gac cat gtg tgt gat    2592
Cys Val Cys Arg Asp Arg Lys Trp Asn Cys Thr Asp His Val Cys Asp
850             855             860 gcc acg tgc tcc acg atc ggc atg gcc cac tac ctc acc ttc gac ggg    2640
Ala Thr Cys Ser Thr Ile Gly Met Ala His Tyr Leu Thr Phe Asp Gly
865             870             875             880 ctc aaa tac ctg ttc ccc ggg gag tgc cag tac gtt ctg gtg cag gat    2688
Leu Lys Tyr Leu Phe Pro Gly Glu Cys Gln Tyr Val Leu Val Gln Asp
            885             890             895 tac tgc ggc agt aac cct ggg acc ttt cgg atc cta gtg ggg aat aag    2736
Tyr Cys Gly Ser Asn Pro Gly Thr Phe Arg Ile Leu Val Gly Asn Lys
        900             905             910 gga tgc agc cac ccc tca gtg aaa tgc aag aaa cgg gtc acc atc ctg    2784
Gly Cys Ser His Pro Ser Val Lys Cys Lys Lys Arg Val Thr Ile Leu
    915             920             925 gtg gag gga gga gag att gag ctg ttt gac ggg gag gtg aat gtg aag    2832
Val Glu Gly Gly Glu Ile Glu Leu Phe Asp Gly Glu Val Asn Val Lys
930             935             940 agg ccc atg aag gat gag act cac ttt gag gtg gtg gag tct ggc cgg    2880
Arg Pro Met Lys Asp Glu Thr His Phe Glu Val Val Glu Ser Gly Arg
945             950             955             960 tac atc att ctg ctg ctg ggc aaa gcc ctc tcc gtg gtc tgg gac cgc    2928
Tyr Ile Ile Leu Leu Leu Gly Lys Ala Leu Ser Val Val Trp Asp Arg
            965             970             975 cac ctg agc atc tcc gtg gtc ctg aag cag aca tac cag gag aaa gtg    2976
His Leu Ser Ile Ser Val Val Leu Lys Gln Thr Tyr Gln Glu Lys Val
        980             985             990 tgt ggc ctg tgt ggg aat ttt gat ggc atc cag aac aat gac ctc acc    3024
Cys Gly Leu Cys Gly Asn Phe Asp Gly Ile Gln Asn Asn Asp Leu Thr
    995             1000            1005 agc agc aac ctc caa gtg gag gaa gac cct gtg gac ttt ggg aac        3069
Ser Ser Asn Leu Gln Val Glu Glu Asp Pro Val Asp Phe Gly Asn
    1010            1015            1020 tcc tgg aaa gtg agc tcg cag tgt gct gac acc aga aaa gtg cct        3114
Ser Trp Lys Val Ser Ser Gln Cys Ala Asp Thr Arg Lys Val Pro
    1025            1030            1035 ctg gac tca tcc cct gcc acc tgc cat aac aac atc atg aag cag        3159
Leu Asp Ser Ser Pro Ala Thr Cys His Asn Asn Ile Met Lys Gln
    1040            1045            1050
```

```
acg atg gtg gat tcc tcc tgt aga atc ctt acc agt gac gtc ttc     3204
Thr Met Val Asp Ser Ser Cys Arg Ile Leu Thr Ser Asp Val Phe
1055            1060                1065 cag gac tgc aac aag ctg gtg gac ccc gag cca tat ctg gat gtc     3249
Gln Asp Cys Asn Lys Leu Val Asp Pro Glu Pro Tyr Leu Asp Val
1070            1075                1080 tgc att tac gac acc tgc tcc tgt gag tcc att ggg gac tgc gcc     3294
Cys Ile Tyr Asp Thr Cys Ser Cys Glu Ser Ile Gly Asp Cys Ala
1085            1090                1095 tgc ttc tgc gac acc att gct gcc tat gcc cac gtg tgt gcc cag     3339
Cys Phe Cys Asp Thr Ile Ala Ala Tyr Ala His Val Cys Ala Gln
1100            1105                1110 cat ggc aag gtg gtg acc tgg agg acg gcc aca ttg tgc ccc cag     3384
His Gly Lys Val Val Thr Trp Arg Thr Ala Thr Leu Cys Pro Gln
1115            1120                1125 agc tgc gag gag agg aat ctc cgg gag aac ggg tat gag tgt gag     3429
Ser Cys Glu Glu Arg Asn Leu Arg Glu Asn Gly Tyr Glu Cys Glu
1130            1135                1140 tgg cgc tat aac agc tgt gca cct gcc tgt caa gtc acg tgt cag     3474
Trp Arg Tyr Asn Ser Cys Ala Pro Ala Cys Gln Val Thr Cys Gln
1145            1150                1155 cac cct gag cca ctg gcc tgc cct gtg cag tgt gtg gag ggc tgc     3519
His Pro Glu Pro Leu Ala Cys Pro Val Gln Cys Val Glu Gly Cys
1160            1165                1170 cat gcc cac tgc cct cca ggg aaa atc ctg gat gag ctt ttg cag     3564
His Ala His Cys Pro Pro Gly Lys Ile Leu Asp Glu Leu Leu Gln
1175            1180                1185 acc tgc gtt gac cct gaa gac tgt cca gtg tgt gag gtg gct ggc     3609
Thr Cys Val Asp Pro Glu Asp Cys Pro Val Cys Glu Val Ala Gly
1190            1195                1200 cgg cgt ttt gcc tca gga aag aaa gtc acc ttg aat ccc agt gac     3654
Arg Arg Phe Ala Ser Gly Lys Lys Val Thr Leu Asn Pro Ser Asp
1205            1210                1215 cct gag cac tgc cag att tgc cac tgt gat gtt gtc aac ctc acc     3699
Pro Glu His Cys Gln Ile Cys His Cys Asp Val Val Asn Leu Thr
1220            1225                1230 tgt gaa gcc tgc cag gag ccg gga ggc ctg gtg gtg cct ccc aca     3744
Cys Glu Ala Cys Gln Glu Pro Gly Gly Leu Val Val Pro Pro Thr
1235            1240                1245 gat gcc ccg gtg agc ccc acc act ctg tat gtg gag gac atc tcg     3789
Asp Ala Pro Val Ser Pro Thr Thr Leu Tyr Val Glu Asp Ile Ser
1250            1255                1260 gaa ccg ccg ttg cac gat ttc tac tgc agc agg cta ctg gac ctg     3834
Glu Pro Pro Leu His Asp Phe Tyr Cys Ser Arg Leu Leu Asp Leu
1265            1270                1275 gtc ttc ctg ctg gat ggc tcc tcc agg ctg tcc gag gct gag ttt     3879
Val Phe Leu Leu Asp Gly Ser Ser Arg Leu Ser Glu Ala Glu Phe
1280            1285                1290 gaa gtg ctg aag gcc ttt gtg gtg gac atg atg gag cgg ctg cgc     3924
Glu Val Leu Lys Ala Phe Val Val Asp Met Met Glu Arg Leu Arg
1295            1300                1305 atc tcc cag aag tgg gtc cgc gtg gcc gtg gtg gag tac cac gac     3969
Ile Ser Gln Lys Trp Val Arg Val Ala Val Val Glu Tyr His Asp
1310            1315                1320 ggc tcc cac gcc tac atc ggg ctc aag gac cgg aag cga ccg tca     4014
Gly Ser His Ala Tyr Ile Gly Leu Lys Asp Arg Lys Arg Pro Ser
1325            1330                1335 gag ctg cgg cgc att gcc agc cag gtg aag tat gcg ggc agc cag     4059
Glu Leu Arg Arg Ile Ala Ser Gln Val Lys Tyr Ala Gly Ser Gln
1340            1345                1350
```

| | | | | | | | | | | | |
|---|---|---|---|---|---|---|---|---|---|---|---|
| gtg | gcc | tcc | acc | agc | gag | gtc | ttg | aaa | tac | aca | ctg | ttc | caa | atc | 4104 |
| Val | Ala | Ser | Thr | Ser | Glu | Val | Leu | Lys | Tyr | Thr | Leu | Phe | Gln | Ile | |
| | 1355 | | | | 1360 | | | | 1365 | | | | | | | ttc agc aag atc gac cgc cct gaa gcc tcc cgc atc gcc ctg ctc    4149
Phe Ser Lys Ile Asp Arg Pro Glu Ala Ser Arg Ile Ala Leu Leu
    1370            1375            1380 ctg atg gcc agc cag gag ccc caa cgg atg tcc cgg aac ttt gtc    4194
Leu Met Ala Ser Gln Glu Pro Gln Arg Met Ser Arg Asn Phe Val
1385            1390            1395 cgc tac gtc cag ggc ctg aag aag aag aag gtc att gtg atc ccg    4239
Arg Tyr Val Gln Gly Leu Lys Lys Lys Lys Val Ile Val Ile Pro
    1400            1405            1410 gtg ggc att ggg ccc cat gcc aac ctc aag cag atc cgc ctc atc    4284
Val Gly Ile Gly Pro His Ala Asn Leu Lys Gln Ile Arg Leu Ile
1415            1420            1425 gag aag cag gcc cct gag aac aag gcc ttc gtg ctg agc agt gtg    4329
Glu Lys Gln Ala Pro Glu Asn Lys Ala Phe Val Leu Ser Ser Val
    1430            1435            1440 gat gag ctg gag cag caa agg gac gag atc gtt agc tac ctc tgt    4374
Asp Glu Leu Glu Gln Gln Arg Asp Glu Ile Val Ser Tyr Leu Cys
1445            1450            1455 gac ctt gcc cct gaa gcc cct cct cct act ctg ccc ccc cac atg    4419
Asp Leu Ala Pro Glu Ala Pro Pro Pro Thr Leu Pro Pro His Met
    1460            1465            1470 gca caa gtc act gtg ggc ccg ggg ctc ttg ggg gtt tcg acc ctg    4464
Ala Gln Val Thr Val Gly Pro Gly Leu Leu Gly Val Ser Thr Leu
1475            1480            1485 ggg ccc aag agg aac tcc atg gtt ctg gat gtg gcg ttc gtc ctg    4509
Gly Pro Lys Arg Asn Ser Met Val Leu Asp Val Ala Phe Val Leu
    1490            1495            1500 gaa gga tcg gac aaa att ggt gaa gcc gac ttc aac agg agc aag    4554
Glu Gly Ser Asp Lys Ile Gly Glu Ala Asp Phe Asn Arg Ser Lys
1505            1510            1515 gag ttc atg gag gag gtg att cag cgg atg gat gtg ggc cag gac    4599
Glu Phe Met Glu Glu Val Ile Gln Arg Met Asp Val Gly Gln Asp
    1520            1525            1530 agc atc cac gtc acg gtg ctc cag tac tcc tac atg gtg acc gtg    4644
Ser Ile His Val Thr Val Leu Gln Tyr Ser Tyr Met Val Thr Val
1535            1540            1545 gag tac ccc ttc agc gag gca cag tcc aaa ggg gac atc ctg cag    4689
Glu Tyr Pro Phe Ser Glu Ala Gln Ser Lys Gly Asp Ile Leu Gln
    1550            1555            1560 cgg gtg cga gag atc cgc tac cag ggc ggc aac agg acc aac act    4734
Arg Val Arg Glu Ile Arg Tyr Gln Gly Gly Asn Arg Thr Asn Thr
1565            1570            1575 ggg ctg gcc ctg cgg tac ctc tct gac cac agc ttc ttg gtc agc    4779
Gly Leu Ala Leu Arg Tyr Leu Ser Asp His Ser Phe Leu Val Ser
    1580            1585            1590 cag ggt gac cgg gag cag gcg ccc aac ctg gtc tac atg gtc acc    4824
Gln Gly Asp Arg Glu Gln Ala Pro Asn Leu Val Tyr Met Val Thr
1595            1600            1605 gga aat cct gcc tct gat gag atc aag agg ctg cct gga gac atc    4869
Gly Asn Pro Ala Ser Asp Glu Ile Lys Arg Leu Pro Gly Asp Ile
    1610            1615            1620 cag gtg gtg ccc att gga gtg ggc cct aat gcc aac gtg cag gag    4914
Gln Val Val Pro Ile Gly Val Gly Pro Asn Ala Asn Val Gln Glu
1625            1630            1635 ctg gag agg att ggc tgg ccc aat gcc cct atc ctc atc cag gac    4959
Leu Glu Arg Ile Gly Trp Pro Asn Ala Pro Ile Leu Ile Gln Asp
    1640            1645            1650

-continued

| | | |
|---|---|---|
| ttt gag acg ctc ccc cga gag gct cct gac ctg gtg ctg cag agg<br>Phe Glu Thr Leu Pro Arg Glu Ala Pro Asp Leu Val Leu Gln Arg<br>1655                         1660                     1665 | 5004 |
| tgc tgc tcc gga gag ggg ctg cag atc ccc acc ctc tcc cct gca<br>Cys Cys Ser Gly Glu Gly Leu Gln Ile Pro Thr Leu Ser Pro Ala<br>1670                         1675                     1680 | 5049 |
| cct gac tgc agc cag ccc ctg gac gtg atc ctt ctc ctg gat ggc<br>Pro Asp Cys Ser Gln Pro Leu Asp Val Ile Leu Leu Leu Asp Gly<br>1685                         1690                     1695 | 5094 |
| tcc tcc agt ttc cca gct tct tat ttt gat gaa atg aag agt ttc<br>Ser Ser Ser Phe Pro Ala Ser Tyr Phe Asp Glu Met Lys Ser Phe<br>1700                         1705                     1710 | 5139 |
| gcc aag gct ttc att tca aaa gcc aat ata ggg cct cgt ctc act<br>Ala Lys Ala Phe Ile Ser Lys Ala Asn Ile Gly Pro Arg Leu Thr<br>1715                         1720                     1725 | 5184 |
| cag gtg tca gtg ctg cag tat gga agc atc acc acc att gac gtg<br>Gln Val Ser Val Leu Gln Tyr Gly Ser Ile Thr Thr Ile Asp Val<br>1730                         1735                     1740 | 5229 |
| cca tgg aac gtg gtc ccg gag aaa gcc cat ttg ctg agc ctt gtg<br>Pro Trp Asn Val Val Pro Glu Lys Ala His Leu Leu Ser Leu Val<br>1745                         1750                     1755 | 5274 |
| gac gtc atg cag cgg gag gga ggc ccc agc caa atc ggg gat gcc<br>Asp Val Met Gln Arg Glu Gly Gly Pro Ser Gln Ile Gly Asp Ala<br>1760                         1765                     1770 | 5319 |
| ttg ggc ttt gct gtg cga tac ttg act tca gaa atg cat ggg gcg<br>Leu Gly Phe Ala Val Arg Tyr Leu Thr Ser Glu Met His Gly Ala<br>1775                         1780                     1785 | 5364 |
| cgc ccg gga gcc tca aag gcg gtc gtc atc ctg gtc acg gac gtc<br>Arg Pro Gly Ala Ser Lys Ala Val Val Ile Leu Val Thr Asp Val<br>1790                         1795                     1800 | 5409 |
| tct gtg gat tca gtg gat gca gca gct gat gcc gcc agg tcc aac<br>Ser Val Asp Ser Val Asp Ala Ala Ala Asp Ala Ala Arg Ser Asn<br>1805                         1810                     1815 | 5454 |
| aga gtg aca gtg ttc cct att gga att gga gat cgc tac gat gca<br>Arg Val Thr Val Phe Pro Ile Gly Ile Gly Asp Arg Tyr Asp Ala<br>1820                         1825                     1830 | 5499 |
| gcc cag cta cgg atc ttg gca ggc cca gca ggc gac tcc aac gtg<br>Ala Gln Leu Arg Ile Leu Ala Gly Pro Ala Gly Asp Ser Asn Val<br>1835                         1840                     1845 | 5544 |
| gtg aag ctc cag cga atc gaa gac ctc cct acc atg gtc acc ttg<br>Val Lys Leu Gln Arg Ile Glu Asp Leu Pro Thr Met Val Thr Leu<br>1850                         1855                     1860 | 5589 |
| ggc aat tcc ttc ctc cac aaa ctg tgc tct gga ttt gtt agg att<br>Gly Asn Ser Phe Leu His Lys Leu Cys Ser Gly Phe Val Arg Ile<br>1865                         1870                     1875 | 5634 |
| tgc atg gat gag gat ggg aat gag aag agg ccc ggg gac gtc tgg<br>Cys Met Asp Glu Asp Gly Asn Glu Lys Arg Pro Gly Asp Val Trp<br>1880                         1885                     1890 | 5679 |
| acc ttg cca gac cag tgc cac acc gtg act tgc cag cca gat ggc<br>Thr Leu Pro Asp Gln Cys His Thr Val Thr Cys Gln Pro Asp Gly<br>1895                         1900                     1905 | 5724 |
| cag acc ttg ctg aag agt cat cgg gtc aac tgt gac cgg ggg ctg<br>Gln Thr Leu Leu Lys Ser His Arg Val Asn Cys Asp Arg Gly Leu<br>1910                         1915                     1920 | 5769 |
| agg cct tcg tgc cct aac agc cag tcc cct gtt aaa gtg gaa gag<br>Arg Pro Ser Cys Pro Asn Ser Gln Ser Pro Val Lys Val Glu Glu<br>1925                         1930                     1935 | 5814 |
| acc tgt ggc tgc cgc tgg acc tgc ccc tgc gtg tgc aca ggc agc<br>Thr Cys Gly Cys Arg Trp Thr Cys Pro Cys Val Cys Thr Gly Ser<br>1940                         1945                     1950 | 5859 |

| | | | | | | | | | | | | | | | |
|---|---|---|---|---|---|---|---|---|---|---|---|---|---|---|---|
| tcc | act | cgg | cac | atc | gtg | acc | ttt | gat | ggg | cag | aat | ttc | aag | ctg | 5904 |
| Ser | Thr | Arg | His | Ile | Val | Thr | Phe | Asp | Gly | Gln | Asn | Phe | Lys | Leu | |
| 1955 | | | | 1960 | | | | | 1965 | | | | | | |
| act | ggc | agc | tgt | tct | tat | gtc | cta | ttt | caa | aac | aag | gag | cag | gac | 5949 |
| Thr | Gly | Ser | Cys | Ser | Tyr | Val | Leu | Phe | Gln | Asn | Lys | Glu | Gln | Asp | |
| 1970 | | | | 1975 | | | | | 1980 | | | | | | |
| ctg | gag | gtg | att | ctc | cat | aat | ggt | gcc | tgc | agc | cct | gga | gca | agg | 5994 |
| Leu | Glu | Val | Ile | Leu | His | Asn | Gly | Ala | Cys | Ser | Pro | Gly | Ala | Arg | |
| 1985 | | | | 1990 | | | | | 1995 | | | | | | |
| cag | ggc | tgc | atg | aaa | tcc | atc | gag | gtg | aag | cac | agt | gcc | ctc | tcc | 6039 |
| Gln | Gly | Cys | Met | Lys | Ser | Ile | Glu | Val | Lys | His | Ser | Ala | Leu | Ser | |
| 2000 | | | | 2005 | | | | | 2010 | | | | | | |
| gtc | gag | ctg | cac | agt | gac | atg | gag | gtg | acg | gtg | aat | ggg | aga | ctg | 6084 |
| Val | Glu | Leu | His | Ser | Asp | Met | Glu | Val | Thr | Val | Asn | Gly | Arg | Leu | |
| 2015 | | | | 2020 | | | | | 2025 | | | | | | |
| gtc | tct | gtt | cct | tac | gtg | ggt | ggg | aac | atg | gaa | gtc | aac | gtt | tat | 6129 |
| Val | Ser | Val | Pro | Tyr | Val | Gly | Gly | Asn | Met | Glu | Val | Asn | Val | Tyr | |
| 2030 | | | | 2035 | | | | | 2040 | | | | | | |
| ggt | gcc | atc | atg | cat | gag | gtc | aga | ttc | aat | cac | ctt | ggt | cac | atc | 6174 |
| Gly | Ala | Ile | Met | His | Glu | Val | Arg | Phe | Asn | His | Leu | Gly | His | Ile | |
| 2045 | | | | 2050 | | | | | 2055 | | | | | | |
| ttc | aca | ttc | act | cca | caa | aac | aat | gag | ttc | caa | ctg | cag | ctc | agc | 6219 |
| Phe | Thr | Phe | Thr | Pro | Gln | Asn | Asn | Glu | Phe | Gln | Leu | Gln | Leu | Ser | |
| 2060 | | | | 2065 | | | | | 2070 | | | | | | |
| ccc | aag | act | ttt | gct | tca | aag | acg | tat | ggt | ctg | tgt | ggg | atc | tgt | 6264 |
| Pro | Lys | Thr | Phe | Ala | Ser | Lys | Thr | Tyr | Gly | Leu | Cys | Gly | Ile | Cys | |
| 2075 | | | | 2080 | | | | | 2085 | | | | | | |
| gat | gag | aac | gga | gcc | aat | gac | ttc | atg | ctg | agg | gat | ggc | aca | gtc | 6309 |
| Asp | Glu | Asn | Gly | Ala | Asn | Asp | Phe | Met | Leu | Arg | Asp | Gly | Thr | Val | |
| 2090 | | | | 2095 | | | | | 2100 | | | | | | |
| acc | aca | gac | tgg | aaa | aca | ctt | gtt | cag | gaa | tgg | act | gtg | cag | cgg | 6354 |
| Thr | Thr | Asp | Trp | Lys | Thr | Leu | Val | Gln | Glu | Trp | Thr | Val | Gln | Arg | |
| 2105 | | | | 2110 | | | | | 2115 | | | | | | |
| cca | ggg | cag | acg | tgc | cag | ccc | atc | ctg | gag | gag | cag | tgt | ctt | gtc | 6399 |
| Pro | Gly | Gln | Thr | Cys | Gln | Pro | Ile | Leu | Glu | Glu | Gln | Cys | Leu | Val | |
| 2120 | | | | 2125 | | | | | 2130 | | | | | | |
| ccc | gac | agc | tcc | cac | tgc | cag | gtc | ctc | ctc | tta | cca | ctg | ttt | gct | 6444 |
| Pro | Asp | Ser | Ser | His | Cys | Gln | Val | Leu | Leu | Leu | Pro | Leu | Phe | Ala | |
| 2135 | | | | 2140 | | | | | 2145 | | | | | | |
| gaa | tgc | cac | aag | gtc | ctg | gct | cca | gcc | aca | ttc | tat | gcc | atc | tgc | 6489 |
| Glu | Cys | His | Lys | Val | Leu | Ala | Pro | Ala | Thr | Phe | Tyr | Ala | Ile | Cys | |
| 2150 | | | | 2155 | | | | | 2160 | | | | | | |
| cag | cag | gac | agt | tgc | cac | cag | gag | caa | gtg | tgt | gag | gtg | atc | gcc | 6534 |
| Gln | Gln | Asp | Ser | Cys | His | Gln | Glu | Gln | Val | Cys | Glu | Val | Ile | Ala | |
| 2165 | | | | 2170 | | | | | 2175 | | | | | | |
| tct | tat | gcc | cac | ctc | tgt | cgg | acc | aac | ggg | gtc | tgc | gtt | gac | tgg | 6579 |
| Ser | Tyr | Ala | His | Leu | Cys | Arg | Thr | Asn | Gly | Val | Cys | Val | Asp | Trp | |
| 2180 | | | | 2185 | | | | | 2190 | | | | | | |
| agg | aca | cct | gat | ttc | tgt | gct | atg | tca | tgc | cca | cca | tct | ctg | gtt | 6624 |
| Arg | Thr | Pro | Asp | Phe | Cys | Ala | Met | Ser | Cys | Pro | Pro | Ser | Leu | Val | |
| 2195 | | | | 2200 | | | | | 2205 | | | | | | |
| tat | aac | cac | tgt | gag | cat | ggc | tgt | ccc | cgg | cac | tgt | gat | ggc | aac | 6669 |
| Tyr | Asn | His | Cys | Glu | His | Gly | Cys | Pro | Arg | His | Cys | Asp | Gly | Asn | |
| 2210 | | | | 2215 | | | | | 2220 | | | | | | |
| gtg | agc | tcc | tgt | ggg | gac | cat | ccc | tcc | gaa | ggc | tgt | ttc | tgc | cct | 6714 |
| Val | Ser | Ser | Cys | Gly | Asp | His | Pro | Ser | Glu | Gly | Cys | Phe | Cys | Pro | |
| 2225 | | | | 2230 | | | | | 2235 | | | | | | |
| cca | gat | aaa | gtc | atg | ttg | gaa | ggc | agc | tgt | gtc | cct | gaa | gag | gcc | 6759 |
| Pro | Asp | Lys | Val | Met | Leu | Glu | Gly | Ser | Cys | Val | Pro | Glu | Glu | Ala | |
| 2240 | | | | 2245 | | | | | 2250 | | | | | | |

| | | | | | | | | | | |
|---|---|---|---|---|---|---|---|---|---|---|
| tgc | act | cag | tgc | att | ggt | gag | gat | gga | gtc | cag | cac | cag | ttc | ctg | 6804 |
| Cys | Thr | Gln | Cys | Ile | Gly | Glu | Asp | Gly | Val | Gln | His | Gln | Phe | Leu | |
| | 2255 | | | | 2260 | | | | | 2265 | | | | | |

```
tgc act cag tgc att ggt gag gat gga gtc cag cac cag ttc ctg      6804
Cys Thr Gln Cys Ile Gly Glu Asp Gly Val Gln His Gln Phe Leu
    2255            2260                2265 gaa gcc tgg gtc ccg gac cac cag ccc tgt cag atc tgc aca tgc      6849
Glu Ala Trp Val Pro Asp His Gln Pro Cys Gln Ile Cys Thr Cys
    2270            2275                2280 ctc agc ggg cgg aag gtc aac tgc aca acg cag ccc tgc ccc acg      6894
Leu Ser Gly Arg Lys Val Asn Cys Thr Thr Gln Pro Cys Pro Thr
    2285            2290                2295 gcc aaa gct ccc acg tgt ggc ctg tgt gaa gta gcc cgc ctc cgc      6939
Ala Lys Ala Pro Thr Cys Gly Leu Cys Glu Val Ala Arg Leu Arg
    2300            2305                2310 cag aat gca gac cag tgc tgc ccc gag tat gag tgt gtg tgt gac      6984
Gln Asn Ala Asp Gln Cys Cys Pro Glu Tyr Glu Cys Val Cys Asp
    2315            2320                2325 cca gtg agc tgt gac ctg ccc cca gtg cct cac tgt gaa cgt ggc      7029
Pro Val Ser Cys Asp Leu Pro Pro Val Pro His Cys Glu Arg Gly
    2330            2335                2340 ctc cag ccc aca ctg acc aac cct ggc gag tgc aga ccc aac ttc      7074
Leu Gln Pro Thr Leu Thr Asn Pro Gly Glu Cys Arg Pro Asn Phe
    2345            2350                2355 acc tgc gcc tgc agg aag gag gag tgc aaa aga gtg tcc cca ccc      7119
Thr Cys Ala Cys Arg Lys Glu Glu Cys Lys Arg Val Ser Pro Pro
    2360            2365                2370 tcc tgc ccc ccg cac cgt ttg ccc acc ctt cgg aag acc cag tgc      7164
Ser Cys Pro Pro His Arg Leu Pro Thr Leu Arg Lys Thr Gln Cys
    2375            2380                2385 tgt gat gag tat gag tgt gcc tgc aac tgt gtc aac tcc aca gtg      7209
Cys Asp Glu Tyr Glu Cys Ala Cys Asn Cys Val Asn Ser Thr Val
    2390            2395                2400 agc tgt ccc ctt ggg tac ttg gcc tca acc gcc acc aat gac tgt      7254
Ser Cys Pro Leu Gly Tyr Leu Ala Ser Thr Ala Thr Asn Asp Cys
    2405            2410                2415 ggc tgt acc aca acc acc tgc ctt ccc gac aag gtg tgt gtc cac      7299
Gly Cys Thr Thr Thr Thr Cys Leu Pro Asp Lys Val Cys Val His
    2420            2425                2430 cga agc acc atc tac cct gtg ggc cag ttc tgg gag gag ggc tgc      7344
Arg Ser Thr Ile Tyr Pro Val Gly Gln Phe Trp Glu Glu Gly Cys
    2435            2440                2445 gat gtg tgc acc tgc acc gac atg gag gat gcc gtg atg ggc ctc      7389
Asp Val Cys Thr Cys Thr Asp Met Glu Asp Ala Val Met Gly Leu
    2450            2455                2460 cgc gtg gcc cag tgt tcc cag aag ccc tgt gag gac agc tgt cgg      7434
Arg Val Ala Gln Cys Ser Gln Lys Pro Cys Glu Asp Ser Cys Arg
    2465            2470                2475 tcg ggc ttc act tac gtt ctg cat gaa ggc gag tgc tgt gga agg      7479
Ser Gly Phe Thr Tyr Val Leu His Glu Gly Glu Cys Cys Gly Arg
    2480            2485                2490 tgc ctg cca tct gcc tgt gag gtg gtg act ggc tca ccg cgg ggg      7524
Cys Leu Pro Ser Ala Cys Glu Val Val Thr Gly Ser Pro Arg Gly
    2495            2500                2505 gac tcc cag tct tcc tgg aag agt gtc ggc tcc cag tgg gcc tcc      7569
Asp Ser Gln Ser Ser Trp Lys Ser Val Gly Ser Gln Trp Ala Ser
    2510            2515                2520 ccg gag aac ccc tgc ctc atc aat gag tgt gtc cga gtg aag gag      7614
Pro Glu Asn Pro Cys Leu Ile Asn Glu Cys Val Arg Val Lys Glu
    2525            2530                2535 gag gtc ttt ata caa caa agg aac gtc tcc tgc ccc cag ctg gag      7659
Glu Val Phe Ile Gln Gln Arg Asn Val Ser Cys Pro Gln Leu Glu
    2540            2545                2550
```

| | | | | | | | | | | | | | | |
|---|---|---|---|---|---|---|---|---|---|---|---|---|---|---|
| gtc | cct | gtc | tgc | ccc | tcg | ggc | ttt | cag | ctg | agc | tgt | aag | acc | tca | 7704 |
| Val | Pro | Val | Cys | Pro | Ser | Gly | Phe | Gln | Leu | Ser | Cys | Lys | Thr | Ser | |
| 2555 | | | | 2560 | | | | | 2565 | | | | | | |

| | | | | | | | | | | | | | | |
|---|---|---|---|---|---|---|---|---|---|---|---|---|---|---|
| gcg | tgc | tgc | cca | agc | tgt | cgc | tgt | gag | cgc | atg | gag | gcc | tgc | atg | 7749 |
| Ala | Cys | Cys | Pro | Ser | Cys | Arg | Cys | Glu | Arg | Met | Glu | Ala | Cys | Met | |
| 2570 | | | | 2575 | | | | | 2580 | | | | | | |

| | | | | | | | | | | | | | | |
|---|---|---|---|---|---|---|---|---|---|---|---|---|---|---|
| ctc | aat | ggc | act | gtc | att | ggg | ccc | ggg | aag | act | gtg | atg | atc | gat | 7794 |
| Leu | Asn | Gly | Thr | Val | Ile | Gly | Pro | Gly | Lys | Thr | Val | Met | Ile | Asp | |
| 2585 | | | | 2590 | | | | | 2595 | | | | | | |

| | | | | | | | | | | | | | | |
|---|---|---|---|---|---|---|---|---|---|---|---|---|---|---|
| gtg | tgc | acg | acc | tgc | cgc | tgc | atg | gtg | cag | gtg | ggg | gtc | atc | tct | 7839 |
| Val | Cys | Thr | Thr | Cys | Arg | Cys | Met | Val | Gln | Val | Gly | Val | Ile | Ser | |
| 2600 | | | | 2605 | | | | | 2610 | | | | | | |

| | | | | | | | | | | | | | | |
|---|---|---|---|---|---|---|---|---|---|---|---|---|---|---|
| gga | ttc | aag | ctg | gag | tgc | agg | aag | acc | acc | tgc | aac | ccc | tgc | ccc | 7884 |
| Gly | Phe | Lys | Leu | Glu | Cys | Arg | Lys | Thr | Thr | Cys | Asn | Pro | Cys | Pro | |
| 2615 | | | | 2620 | | | | | 2625 | | | | | | |

| | | | | | | | | | | | | | | |
|---|---|---|---|---|---|---|---|---|---|---|---|---|---|---|
| ctg | ggt | tac | aag | gaa | gaa | aat | aac | aca | ggt | gaa | tgt | tgt | ggg | aga | 7929 |
| Leu | Gly | Tyr | Lys | Glu | Glu | Asn | Asn | Thr | Gly | Glu | Cys | Cys | Gly | Arg | |
| 2630 | | | | 2635 | | | | | 2640 | | | | | | |

| | | | | | | | | | | | | | | |
|---|---|---|---|---|---|---|---|---|---|---|---|---|---|---|
| tgt | ttg | cct | acg | gct | tgc | acc | att | cag | cta | aga | gga | gga | cag | atc | 7974 |
| Cys | Leu | Pro | Thr | Ala | Cys | Thr | Ile | Gln | Leu | Arg | Gly | Gly | Gln | Ile | |
| 2645 | | | | 2650 | | | | | 2655 | | | | | | |

| | | | | | | | | | | | | | | |
|---|---|---|---|---|---|---|---|---|---|---|---|---|---|---|
| atg | aca | ctg | aag | cgt | gat | gag | acg | ctc | cag | gat | ggc | tgt | gat | act | 8019 |
| Met | Thr | Leu | Lys | Arg | Asp | Glu | Thr | Leu | Gln | Asp | Gly | Cys | Asp | Thr | |
| 2660 | | | | 2665 | | | | | 2670 | | | | | | |

| | | | | | | | | | | | | | | |
|---|---|---|---|---|---|---|---|---|---|---|---|---|---|---|
| cac | ttc | tgc | aag | gtc | aat | gag | aga | gga | gag | tac | ttc | tgg | gag | aag | 8064 |
| His | Phe | Cys | Lys | Val | Asn | Glu | Arg | Gly | Glu | Tyr | Phe | Trp | Glu | Lys | |
| 2675 | | | | 2680 | | | | | 2685 | | | | | | |

| | | | | | | | | | | | | | | |
|---|---|---|---|---|---|---|---|---|---|---|---|---|---|---|
| agg | gtc | aca | ggc | tgc | cca | ccc | ttt | gat | gaa | cac | aag | tgt | ctg | gct | 8109 |
| Arg | Val | Thr | Gly | Cys | Pro | Pro | Phe | Asp | Glu | His | Lys | Cys | Leu | Ala | |
| 2690 | | | | 2695 | | | | | 2700 | | | | | | |

| | | | | | | | | | | | | | | |
|---|---|---|---|---|---|---|---|---|---|---|---|---|---|---|
| gag | gga | ggt | aaa | att | atg | aaa | att | cca | ggc | acc | tgc | tgt | gac | aca | 8154 |
| Glu | Gly | Gly | Lys | Ile | Met | Lys | Ile | Pro | Gly | Thr | Cys | Cys | Asp | Thr | |
| 2705 | | | | 2710 | | | | | 2715 | | | | | | |

| | | | | | | | | | | | | | | |
|---|---|---|---|---|---|---|---|---|---|---|---|---|---|---|
| tgt | gag | gag | cct | gag | tgc | aac | gac | atc | act | gcc | agg | ctg | cag | tat | 8199 |
| Cys | Glu | Glu | Pro | Glu | Cys | Asn | Asp | Ile | Thr | Ala | Arg | Leu | Gln | Tyr | |
| 2720 | | | | 2725 | | | | | 2730 | | | | | | |

| | | | | | | | | | | | | | | |
|---|---|---|---|---|---|---|---|---|---|---|---|---|---|---|
| gtc | aag | gtg | gga | agc | tgt | aag | tct | gaa | gta | gag | gtg | gat | atc | cac | 8244 |
| Val | Lys | Val | Gly | Ser | Cys | Lys | Ser | Glu | Val | Glu | Val | Asp | Ile | His | |
| 2735 | | | | 2740 | | | | | 2745 | | | | | | |

| | | | | | | | | | | | | | | |
|---|---|---|---|---|---|---|---|---|---|---|---|---|---|---|
| tac | tgc | cag | ggc | aaa | tgt | gcc | agc | aaa | gcc | atg | tac | tcc | att | gac | 8289 |
| Tyr | Cys | Gln | Gly | Lys | Cys | Ala | Ser | Lys | Ala | Met | Tyr | Ser | Ile | Asp | |
| 2750 | | | | 2755 | | | | | 2760 | | | | | | |

| | | | | | | | | | | | | | | |
|---|---|---|---|---|---|---|---|---|---|---|---|---|---|---|
| atc | aac | gat | gtg | cag | gac | cag | tgc | tcc | tgc | tgt | tct | ccg | aca | cgg | 8334 |
| Ile | Asn | Asp | Val | Gln | Asp | Gln | Cys | Ser | Cys | Cys | Ser | Pro | Thr | Arg | |
| 2765 | | | | 2770 | | | | | 2775 | | | | | | |

| | | | | | | | | | | | | | | |
|---|---|---|---|---|---|---|---|---|---|---|---|---|---|---|
| acg | gag | ccc | atg | cag | gtg | gcc | ctg | cac | tgc | acc | aat | ggc | tct | gtt | 8379 |
| Thr | Glu | Pro | Met | Gln | Val | Ala | Leu | His | Cys | Thr | Asn | Gly | Ser | Val | |
| 2780 | | | | 2785 | | | | | 2790 | | | | | | |

| | | | | | | | | | | | | | | |
|---|---|---|---|---|---|---|---|---|---|---|---|---|---|---|
| gtg | tac | cat | gag | gtt | ctc | aat | gcc | atg | gag | tgc | aaa | tgc | tcc | ccc | 8424 |
| Val | Tyr | His | Glu | Val | Leu | Asn | Ala | Met | Glu | Cys | Lys | Cys | Ser | Pro | |
| 2795 | | | | 2800 | | | | | 2805 | | | | | | |

| | | | | |
|---|---|---|---|---|
| agg | aag | tgc | agc | aag | tga | 8442 |
| Arg | Lys | Cys | Ser | Lys | |
| 2810 | | | | | |

<210> SEQ ID NO 4
<211> LENGTH: 2813
<212> TYPE: PRT
<213> ORGANISM: Homo sapiens

<400> SEQUENCE: 4

```
Met Ile Pro Ala Arg Phe Ala Gly Val Leu Leu Ala Leu Ala Leu Ile
1               5                   10                  15
Leu Pro Gly Thr Leu Cys Ala Glu Gly Thr Arg Gly Arg Ser Ser Thr
            20                  25                  30
Ala Arg Cys Ser Leu Phe Gly Ser Asp Phe Val Asn Thr Phe Asp Gly
        35                  40                  45
Ser Met Tyr Ser Phe Ala Gly Tyr Cys Ser Tyr Leu Leu Ala Gly Gly
    50                  55                  60
Cys Gln Lys Arg Ser Phe Ser Ile Ile Gly Asp Phe Gln Asn Gly Lys
65                  70                  75                  80
Arg Val Ser Leu Ser Val Tyr Leu Gly Glu Phe Phe Asp Ile His Leu
                85                  90                  95
Phe Val Asn Gly Thr Val Thr Gln Gly Asp Gln Arg Val Ser Met Pro
            100                 105                 110
Tyr Ala Ser Lys Gly Leu Tyr Leu Glu Thr Glu Ala Gly Tyr Tyr Lys
        115                 120                 125
Leu Ser Gly Glu Ala Tyr Gly Phe Val Ala Arg Ile Asp Gly Ser Gly
    130                 135                 140
Asn Phe Gln Val Leu Leu Ser Asp Arg Tyr Phe Asn Lys Thr Cys Gly
145                 150                 155                 160
Leu Cys Gly Asn Phe Asn Ile Phe Ala Glu Asp Asp Phe Met Thr Gln
                165                 170                 175
Glu Gly Thr Leu Thr Ser Asp Pro Tyr Asp Phe Ala Asn Ser Trp Ala
            180                 185                 190
Leu Ser Ser Gly Glu Gln Trp Cys Glu Arg Ala Ser Pro Pro Ser Ser
        195                 200                 205
Ser Cys Asn Ile Ser Ser Gly Glu Met Gln Lys Gly Leu Trp Glu Gln
    210                 215                 220
Cys Gln Leu Leu Lys Ser Thr Ser Val Phe Ala Arg Cys His Pro Leu
225                 230                 235                 240
Val Asp Pro Glu Pro Phe Val Ala Leu Cys Glu Lys Thr Leu Cys Glu
                245                 250                 255
Cys Ala Gly Gly Leu Glu Cys Ala Cys Pro Ala Leu Leu Glu Tyr Ala
            260                 265                 270
Arg Thr Cys Ala Gln Glu Gly Met Val Leu Tyr Gly Trp Thr Asp His
        275                 280                 285
Ser Ala Cys Ser Pro Val Cys Pro Ala Gly Met Glu Tyr Arg Gln Cys
    290                 295                 300
Val Ser Pro Cys Ala Arg Thr Cys Gln Ser Leu His Ile Asn Glu Met
305                 310                 315                 320
Cys Gln Glu Arg Cys Val Asp Gly Cys Ser Cys Pro Glu Gly Gln Leu
                325                 330                 335
Leu Asp Glu Gly Leu Cys Val Glu Ser Thr Glu Cys Pro Cys Val His
            340                 345                 350
Ser Gly Lys Arg Tyr Pro Pro Gly Thr Ser Leu Ser Arg Asp Cys Asn
        355                 360                 365
Thr Cys Ile Cys Arg Asn Ser Gln Trp Ile Cys Ser Asn Glu Glu Cys
    370                 375                 380
Pro Gly Glu Cys Leu Val Thr Gly Gln Ser His Phe Lys Ser Phe Asp
385                 390                 395                 400
Asn Arg Tyr Phe Thr Phe Ser Gly Ile Cys Gln Tyr Leu Leu Ala Arg
                405                 410                 415
```

```
Asp Cys Gln Asp His Ser Phe Ser Ile Val Glu Thr Val Gln Cys
                420                 425                 430

Ala Asp Asp Arg Asp Ala Val Cys Thr Arg Ser Val Thr Val Arg Leu
            435                 440                 445

Pro Gly Leu His Asn Ser Leu Val Lys Leu Lys His Gly Ala Gly Val
450                 455                 460

Ala Met Asp Gly Gln Asp Val Gln Leu Pro Leu Leu Lys Gly Asp Leu
465                 470                 475                 480

Arg Ile Gln His Thr Val Thr Ala Ser Val Arg Leu Ser Tyr Gly Glu
                485                 490                 495

Asp Leu Gln Met Asp Trp Asp Gly Arg Gly Arg Leu Leu Val Lys Leu
                500                 505                 510

Ser Pro Val Tyr Ala Gly Lys Thr Cys Gly Leu Cys Gly Asn Tyr Asn
            515                 520                 525

Gly Asn Gln Gly Asp Asp Phe Leu Thr Pro Ser Gly Leu Ala Glu Pro
            530                 535                 540

Arg Val Glu Asp Phe Gly Asn Ala Trp Lys Leu His Gly Asp Cys Gln
545                 550                 555                 560

Asp Leu Gln Lys Gln His Ser Asp Pro Cys Ala Leu Asn Pro Arg Met
                565                 570                 575

Thr Arg Phe Ser Glu Glu Ala Cys Ala Val Leu Thr Ser Pro Thr Phe
            580                 585                 590

Glu Ala Cys His Arg Ala Val Ser Pro Leu Pro Tyr Leu Arg Asn Cys
                595                 600                 605

Arg Tyr Asp Val Cys Ser Cys Ser Asp Gly Arg Glu Cys Leu Cys Gly
610                 615                 620

Ala Leu Ala Ser Tyr Ala Ala Ala Cys Ala Gly Arg Gly Val Arg Val
625                 630                 635                 640

Ala Trp Arg Glu Pro Gly Arg Cys Glu Leu Asn Cys Pro Lys Gly Gln
                645                 650                 655

Val Tyr Leu Gln Cys Gly Thr Pro Cys Asn Leu Thr Cys Arg Ser Leu
            660                 665                 670

Ser Tyr Pro Asp Glu Glu Cys Asn Glu Ala Cys Leu Glu Gly Cys Phe
            675                 680                 685

Cys Pro Pro Gly Leu Tyr Met Asp Glu Arg Gly Asp Cys Val Pro Lys
690                 695                 700

Ala Gln Cys Pro Cys Tyr Tyr Asp Gly Glu Ile Phe Gln Pro Glu Asp
705                 710                 715                 720

Ile Phe Ser Asp His His Thr Met Cys Tyr Cys Glu Asp Gly Phe Met
                725                 730                 735

His Cys Thr Met Ser Gly Val Pro Gly Ser Leu Leu Pro Asp Ala Val
                740                 745                 750

Leu Ser Ser Pro Leu Ser His Arg Ser Lys Arg Ser Leu Ser Cys Arg
                755                 760                 765

Pro Pro Met Val Lys Leu Val Cys Pro Ala Asp Asn Leu Arg Ala Glu
            770                 775                 780

Gly Leu Glu Cys Thr Lys Thr Cys Gln Asn Tyr Asp Leu Glu Cys Met
785                 790                 795                 800

Ser Met Gly Cys Val Ser Gly Cys Leu Cys Pro Pro Gly Met Val Arg
                805                 810                 815

His Glu Asn Arg Cys Val Ala Leu Glu Arg Cys Pro Cys Phe His Gln
                820                 825                 830
```

```
Gly Lys Glu Tyr Ala Pro Gly Thr Val Lys Ile Gly Cys Asn Thr
            835                 840                 845

Cys Val Cys Arg Asp Arg Lys Trp Asn Cys Thr Asp His Val Cys Asp
    850                 855                 860

Ala Thr Cys Ser Thr Ile Gly Met Ala His Tyr Leu Thr Phe Asp Gly
865                 870                 875                 880

Leu Lys Tyr Leu Phe Pro Gly Glu Cys Gln Tyr Val Leu Val Gln Asp
                885                 890                 895

Tyr Cys Gly Ser Asn Pro Gly Thr Phe Arg Ile Leu Val Gly Asn Lys
            900                 905                 910

Gly Cys Ser His Pro Ser Val Lys Cys Lys Arg Val Thr Ile Leu
            915                 920                 925

Val Glu Gly Gly Glu Ile Glu Leu Phe Asp Gly Glu Val Asn Val Lys
930                 935                 940

Arg Pro Met Lys Asp Glu Thr His Phe Glu Val Val Glu Ser Gly Arg
945                 950                 955                 960

Tyr Ile Ile Leu Leu Leu Gly Lys Ala Leu Ser Val Val Trp Asp Arg
            965                 970                 975

His Leu Ser Ile Ser Val Val Leu Lys Gln Thr Tyr Gln Glu Lys Val
            980                 985                 990

Cys Gly Leu Cys Gly Asn Phe Asp  Gly Ile Gln Asn Asn  Asp Leu Thr
        995                 1000                1005

Ser Ser  Asn Leu Gln Val Glu  Glu Asp Pro Val Asp  Phe Gly Asn
    1010                 1015                1020

Ser Trp  Lys Val Ser Ser Gln  Cys Ala Asp Thr Arg  Lys Val Pro
    1025                 1030                1035

Leu Asp  Ser Ser Pro Ala Thr  Cys His Asn Asn Ile  Met Lys Gln
    1040                 1045                1050

Thr Met  Val Asp Ser Ser Cys  Arg Ile Leu Thr Ser  Asp Val Phe
    1055                 1060                1065

Gln Asp  Cys Asn Lys Leu Val  Asp Pro Glu Pro Tyr  Leu Asp Val
    1070                 1075                1080

Cys Ile  Tyr Asp Thr Cys Ser  Cys Glu Ser Ile Gly  Asp Cys Ala
    1085                 1090                1095

Cys Phe  Cys Asp Thr Ile Ala  Ala Tyr Ala His Val  Cys Ala Gln
    1100                 1105                1110

His Gly  Lys Val Val Thr Trp  Arg Thr Ala Thr Leu  Cys Pro Gln
    1115                 1120                1125

Ser Cys  Glu Glu Arg Asn Leu  Arg Glu Asn Gly Tyr  Glu Cys Glu
    1130                 1135                1140

Trp Arg  Tyr Asn Ser Cys Ala  Pro Ala Cys Gln Val  Thr Cys Gln
    1145                 1150                1155

His Pro  Glu Pro Leu Ala Cys  Pro Val Gln Cys Val  Glu Gly Cys
    1160                 1165                1170

His Ala  His Cys Pro Pro Gly  Lys Ile Leu Asp Glu  Leu Leu Gln
    1175                 1180                1185

Thr Cys  Val Asp Pro Glu Asp  Cys Pro Val Cys Glu  Val Ala Gly
    1190                 1195                1200

Arg Arg  Phe Ala Ser Gly Lys  Lys Val Thr Leu Asn  Pro Ser Asp
    1205                 1210                1215

Pro Glu  His Cys Gln Ile Cys  His Cys Asp Val Val  Asn Leu Thr
    1220                 1225                1230
```

```
Cys Glu Ala Cys Gln Glu Pro Gly Gly Leu Val Val Pro Pro Thr
1235                1240                1245

Asp Ala Pro Val Ser Pro Thr Thr Leu Tyr Val Glu Asp Ile Ser
1250                1255                1260

Glu Pro Pro Leu His Asp Phe Tyr Cys Ser Arg Leu Leu Asp Leu
1265                1270                1275

Val Phe Leu Leu Asp Gly Ser Ser Arg Leu Ser Glu Ala Glu Phe
1280                1285                1290

Glu Val Leu Lys Ala Phe Val Val Asp Met Met Glu Arg Leu Arg
1295                1300                1305

Ile Ser Gln Lys Trp Val Arg Val Ala Val Val Glu Tyr His Asp
1310                1315                1320

Gly Ser His Ala Tyr Ile Gly Leu Lys Asp Arg Lys Arg Pro Ser
1325                1330                1335

Glu Leu Arg Arg Ile Ala Ser Gln Val Lys Tyr Ala Gly Ser Gln
1340                1345                1350

Val Ala Ser Thr Ser Glu Val Leu Lys Tyr Thr Leu Phe Gln Ile
1355                1360                1365

Phe Ser Lys Ile Asp Arg Pro Glu Ala Ser Arg Ile Ala Leu Leu
1370                1375                1380

Leu Met Ala Ser Gln Glu Pro Gln Arg Met Ser Arg Asn Phe Val
1385                1390                1395

Arg Tyr Val Gln Gly Leu Lys Lys Lys Val Ile Val Ile Pro
1400                1405                1410

Val Gly Ile Gly Pro His Ala Asn Leu Lys Gln Ile Arg Leu Ile
1415                1420                1425

Glu Lys Gln Ala Pro Glu Asn Lys Ala Phe Val Leu Ser Ser Val
1430                1435                1440

Asp Glu Leu Glu Gln Gln Arg Asp Glu Ile Val Ser Tyr Leu Cys
1445                1450                1455

Asp Leu Ala Pro Glu Ala Pro Pro Pro Thr Leu Pro Pro His Met
1460                1465                1470

Ala Gln Val Thr Val Gly Pro Gly Leu Leu Gly Val Ser Thr Leu
1475                1480                1485

Gly Pro Lys Arg Asn Ser Met Val Leu Asp Val Ala Phe Val Leu
1490                1495                1500

Glu Gly Ser Asp Lys Ile Gly Glu Ala Asp Phe Asn Arg Ser Lys
1505                1510                1515

Glu Phe Met Glu Glu Val Ile Gln Arg Met Asp Val Gly Gln Asp
1520                1525                1530

Ser Ile His Val Thr Val Leu Gln Tyr Ser Tyr Met Val Thr Val
1535                1540                1545

Glu Tyr Pro Phe Ser Glu Ala Gln Ser Lys Gly Asp Ile Leu Gln
1550                1555                1560

Arg Val Arg Glu Ile Arg Tyr Gln Gly Gly Asn Arg Thr Asn Thr
1565                1570                1575

Gly Leu Ala Leu Arg Tyr Leu Ser Asp His Ser Phe Leu Val Ser
1580                1585                1590

Gln Gly Asp Arg Glu Gln Ala Pro Asn Leu Val Tyr Met Val Thr
1595                1600                1605

Gly Asn Pro Ala Ser Asp Glu Ile Lys Arg Leu Pro Gly Asp Ile
1610                1615                1620
```

Gln Val Val Pro Ile Gly Val Gly Pro Asn Ala Asn Val Gln Glu
    1625            1630            1635

Leu Glu Arg Ile Gly Trp Pro Asn Ala Pro Ile Leu Ile Gln Asp
    1640            1645            1650

Phe Glu Thr Leu Pro Arg Glu Ala Pro Asp Leu Val Leu Gln Arg
    1655            1660            1665

Cys Cys Ser Gly Glu Gly Leu Gln Ile Pro Thr Leu Ser Pro Ala
    1670            1675            1680

Pro Asp Cys Ser Gln Pro Leu Asp Val Ile Leu Leu Leu Asp Gly
    1685            1690            1695

Ser Ser Ser Phe Pro Ala Ser Tyr Phe Asp Glu Met Lys Ser Phe
    1700            1705            1710

Ala Lys Ala Phe Ile Ser Lys Ala Asn Ile Gly Pro Arg Leu Thr
    1715            1720            1725

Gln Val Ser Val Leu Gln Tyr Gly Ser Ile Thr Thr Ile Asp Val
    1730            1735            1740

Pro Trp Asn Val Val Pro Glu Lys Ala His Leu Leu Ser Leu Val
    1745            1750            1755

Asp Val Met Gln Arg Glu Gly Gly Pro Ser Gln Ile Gly Asp Ala
    1760            1765            1770

Leu Gly Phe Ala Val Arg Tyr Leu Thr Ser Glu Met His Gly Ala
    1775            1780            1785

Arg Pro Gly Ala Ser Lys Ala Val Val Ile Leu Val Thr Asp Val
    1790            1795            1800

Ser Val Asp Ser Val Asp Ala Ala Ala Asp Ala Ala Arg Ser Asn
    1805            1810            1815

Arg Val Thr Val Phe Pro Ile Gly Ile Gly Asp Arg Tyr Asp Ala
    1820            1825            1830

Ala Gln Leu Arg Ile Leu Ala Gly Pro Ala Gly Asp Ser Asn Val
    1835            1840            1845

Val Lys Leu Gln Arg Ile Glu Asp Leu Pro Thr Met Val Thr Leu
    1850            1855            1860

Gly Asn Ser Phe Leu His Lys Leu Cys Ser Gly Phe Val Arg Ile
    1865            1870            1875

Cys Met Asp Glu Asp Gly Asn Glu Lys Arg Pro Gly Asp Val Trp
    1880            1885            1890

Thr Leu Pro Asp Gln Cys His Thr Val Thr Cys Gln Pro Asp Gly
    1895            1900            1905

Gln Thr Leu Leu Lys Ser His Arg Val Asn Cys Asp Arg Gly Leu
    1910            1915            1920

Arg Pro Ser Cys Pro Asn Ser Gln Ser Pro Val Lys Val Glu Glu
    1925            1930            1935

Thr Cys Gly Cys Arg Trp Thr Cys Pro Cys Val Cys Thr Gly Ser
    1940            1945            1950

Ser Thr Arg His Ile Val Thr Phe Asp Gly Gln Asn Phe Lys Leu
    1955            1960            1965

Thr Gly Ser Cys Ser Tyr Val Leu Phe Gln Asn Lys Glu Gln Asp
    1970            1975            1980

Leu Glu Val Ile Leu His Asn Gly Ala Cys Ser Pro Gly Ala Arg
    1985            1990            1995

Gln Gly Cys Met Lys Ser Ile Glu Val Lys His Ser Ala Leu Ser
    2000            2005            2010

```
Val Glu Leu His Ser Asp Met Glu Val Thr Val Asn Gly Arg Leu
2015                2020                2025

Val Ser Val Pro Tyr Val Gly Gly Asn Met Glu Val Asn Val Tyr
2030                2035                2040

Gly Ala Ile Met His Glu Val Arg Phe Asn His Leu Gly His Ile
2045                2050                2055

Phe Thr Phe Thr Pro Gln Asn Asn Glu Phe Gln Leu Gln Leu Ser
2060                2065                2070

Pro Lys Thr Phe Ala Ser Lys Thr Tyr Gly Leu Cys Gly Ile Cys
2075                2080                2085

Asp Glu Asn Gly Ala Asn Asp Phe Met Leu Arg Asp Gly Thr Val
2090                2095                2100

Thr Thr Asp Trp Lys Thr Leu Val Gln Glu Trp Thr Val Gln Arg
2105                2110                2115

Pro Gly Gln Thr Cys Gln Pro Ile Leu Glu Glu Gln Cys Leu Val
2120                2125                2130

Pro Asp Ser Ser His Cys Gln Val Leu Leu Leu Pro Leu Phe Ala
2135                2140                2145

Glu Cys His Lys Val Leu Ala Pro Ala Thr Phe Tyr Ala Ile Cys
2150                2155                2160

Gln Gln Asp Ser Cys His Gln Glu Gln Val Cys Glu Val Ile Ala
2165                2170                2175

Ser Tyr Ala His Leu Cys Arg Thr Asn Gly Val Cys Val Asp Trp
2180                2185                2190

Arg Thr Pro Asp Phe Cys Ala Met Ser Cys Pro Pro Ser Leu Val
2195                2200                2205

Tyr Asn His Cys Glu His Gly Cys Pro Arg His Cys Asp Gly Asn
2210                2215                2220

Val Ser Ser Cys Gly Asp His Pro Ser Glu Gly Cys Phe Cys Pro
2225                2230                2235

Pro Asp Lys Val Met Leu Glu Gly Ser Cys Val Pro Glu Glu Ala
2240                2245                2250

Cys Thr Gln Cys Ile Gly Glu Asp Gly Val Gln His Gln Phe Leu
2255                2260                2265

Glu Ala Trp Val Pro Asp His Gln Pro Cys Gln Ile Cys Thr Cys
2270                2275                2280

Leu Ser Gly Arg Lys Val Asn Cys Thr Thr Gln Pro Cys Pro Thr
2285                2290                2295

Ala Lys Ala Pro Thr Cys Gly Leu Cys Glu Val Ala Arg Leu Arg
2300                2305                2310

Gln Asn Ala Asp Gln Cys Cys Pro Glu Tyr Glu Cys Val Cys Asp
2315                2320                2325

Pro Val Ser Cys Asp Leu Pro Pro Val Pro His Cys Glu Arg Gly
2330                2335                2340

Leu Gln Pro Thr Leu Thr Asn Pro Gly Glu Cys Arg Pro Asn Phe
2345                2350                2355

Thr Cys Ala Cys Arg Lys Glu Glu Cys Lys Arg Val Ser Pro Pro
2360                2365                2370

Ser Cys Pro Pro His Arg Leu Pro Thr Leu Arg Lys Thr Gln Cys
2375                2380                2385

Cys Asp Glu Tyr Glu Cys Ala Cys Asn Cys Val Asn Ser Thr Val
2390                2395                2400
```

-continued

```
Ser Cys Pro Leu Gly Tyr Leu Ala Ser Thr Ala Thr Asn Asp Cys
    2405                2410                2415

Gly Cys Thr Thr Thr Thr Cys Leu Pro Asp Lys Val Cys Val His
    2420                2425                2430

Arg Ser Thr Ile Tyr Pro Val Gly Gln Phe Trp Glu Glu Gly Cys
    2435                2440                2445

Asp Val Cys Thr Cys Thr Asp Met Glu Asp Ala Val Met Gly Leu
    2450                2455                2460

Arg Val Ala Gln Cys Ser Gln Lys Pro Cys Glu Asp Ser Cys Arg
    2465                2470                2475

Ser Gly Phe Thr Tyr Val Leu His Glu Gly Glu Cys Cys Gly Arg
    2480                2485                2490

Cys Leu Pro Ser Ala Cys Glu Val Val Thr Gly Ser Pro Arg Gly
    2495                2500                2505

Asp Ser Gln Ser Ser Trp Lys Ser Val Gly Ser Gln Trp Ala Ser
    2510                2515                2520

Pro Glu Asn Pro Cys Leu Ile Asn Glu Cys Val Arg Val Lys Glu
    2525                2530                2535

Glu Val Phe Ile Gln Gln Arg Asn Val Ser Cys Pro Gln Leu Glu
    2540                2545                2550

Val Pro Val Cys Pro Ser Gly Phe Gln Leu Ser Cys Lys Thr Ser
    2555                2560                2565

Ala Cys Cys Pro Ser Cys Arg Cys Glu Arg Met Glu Ala Cys Met
    2570                2575                2580

Leu Asn Gly Thr Val Ile Gly Pro Gly Lys Thr Val Met Ile Asp
    2585                2590                2595

Val Cys Thr Thr Cys Arg Cys Met Val Gln Val Gly Val Ile Ser
    2600                2605                2610

Gly Phe Lys Leu Glu Cys Arg Lys Thr Thr Cys Asn Pro Cys Pro
    2615                2620                2625

Leu Gly Tyr Lys Glu Glu Asn Asn Thr Gly Glu Cys Cys Gly Arg
    2630                2635                2640

Cys Leu Pro Thr Ala Cys Thr Ile Gln Leu Arg Gly Gly Gln Ile
    2645                2650                2655

Met Thr Leu Lys Arg Asp Glu Thr Leu Gln Asp Gly Cys Asp Thr
    2660                2665                2670

His Phe Cys Lys Val Asn Glu Arg Gly Glu Tyr Phe Trp Glu Lys
    2675                2680                2685

Arg Val Thr Gly Cys Pro Pro Phe Asp Glu His Lys Cys Leu Ala
    2690                2695                2700

Glu Gly Gly Lys Ile Met Lys Ile Pro Gly Thr Cys Cys Asp Thr
    2705                2710                2715

Cys Glu Glu Pro Glu Cys Asn Asp Ile Thr Ala Arg Leu Gln Tyr
    2720                2725                2730

Val Lys Val Gly Ser Cys Lys Ser Glu Val Glu Val Asp Ile His
    2735                2740                2745

Tyr Cys Gln Gly Lys Cys Ala Ser Lys Ala Met Tyr Ser Ile Asp
    2750                2755                2760

Ile Asn Asp Val Gln Asp Gln Cys Ser Cys Cys Ser Pro Thr Arg
    2765                2770                2775

Thr Glu Pro Met Gln Val Ala Leu His Cys Thr Asn Gly Ser Val
    2780                2785                2790
```

```
Val Tyr His Glu Val Leu Asn Ala Met Glu Cys Lys Cys Ser Pro
    2795                2800                2805

Arg Lys Cys Ser Lys
    2810

<210> SEQ ID NO 5
<211> LENGTH: 1444
<212> TYPE: PRT
<213> ORGANISM: Artificial Sequence
<220> FEATURE:
<223> OTHER INFORMATION: amino acid sequence of a single chain factor
      viii molecule

<400> SEQUENCE: 5

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335
```

```
Met Lys Asn Asn Glu Glu Ala Glu Asp Tyr Asp Asp Leu Thr Asp
            340                 345                 350

Ser Glu Met Asp Val Val Arg Phe Asp Asp Asn Ser Pro Ser Phe
            355                 360                 365

Ile Gln Ile Arg Ser Val Ala Lys Lys His Pro Lys Thr Trp Val His
    370                 375                 380

Tyr Ile Ala Ala Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
            405                 410                 415

Gln Arg Ile Gly Arg Lys Tyr Lys Val Arg Phe Met Ala Tyr Thr
            420                 425                 430

Asp Glu Thr Phe Lys Thr Arg Glu Ala Ile Gln His Glu Ser Gly Ile
            435                 440                 445

Leu Gly Pro Leu Leu Tyr Gly Glu Val Gly Asp Thr Leu Leu Ile Ile
            450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
            485                 490                 495

His Leu Lys Asp Phe Pro Ile Leu Pro Gly Glu Ile Phe Lys Tyr Lys
            500                 505                 510

Trp Thr Val Thr Val Glu Asp Gly Pro Thr Lys Ser Asp Pro Arg Cys
            515                 520                 525

Leu Thr Arg Tyr Tyr Ser Ser Phe Val Asn Met Glu Arg Asp Leu Ala
            530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
            565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
            595                 600                 605

Gln Ala Ser Asn Ile Met His Ser Ile Asn Gly Tyr Val Phe Asp Ser
            610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
            645                 650                 655

Thr Phe Lys His Lys Met Val Tyr Glu Asp Thr Leu Thr Leu Phe Pro
            660                 665                 670

Phe Ser Gly Glu Thr Val Phe Met Ser Met Glu Asn Pro Gly Leu Trp
            675                 680                 685

Ile Leu Gly Cys His Asn Ser Asp Phe Arg Asn Arg Gly Met Thr Ala
            690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
            725                 730                 735

Ile Glu Pro Arg Ser Phe Ser Gln Asn Ser Arg His Pro Ser Thr Arg
            740                 745                 750
```

-continued

Gln Lys Gln Phe Asn Ala Thr Thr Ile Pro Glu Asn Thr Leu Gln
            755                 760                 765

Ser Asp Gln Glu Glu Ile Asp Tyr Asp Thr Ile Ser Val Glu Met
    770                 775                 780

Lys Lys Glu Asp Phe Asp Ile Tyr Asp Glu Asp Asn Gln Ser Pro
785                 790                 795                 800

Arg Ser Phe Gln Lys Lys Thr Arg His Tyr Phe Ile Ala Ala Val Glu
            805                 810                 815

Arg Leu Trp Asp Tyr Gly Met Ser Ser Pro His Val Leu Arg Asn
            820                 825                 830

Arg Ala Gln Ser Gly Ser Val Pro Gln Phe Lys Lys Val Val Phe Gln
            835                 840                 845

Glu Phe Thr Asp Gly Ser Phe Thr Gln Pro Leu Tyr Arg Gly Glu Leu
            850                 855                 860

Asn Glu His Leu Gly Leu Leu Gly Pro Tyr Ile Arg Ala Glu Val Glu
865                 870                 875                 880

Asp Asn Ile Met Val Thr Phe Arg Asn Gln Ala Ser Arg Pro Tyr Ser
                885                 890                 895

Phe Tyr Ser Ser Leu Ile Ser Tyr Glu Glu Asp Gln Arg Gln Gly Ala
            900                 905                 910

Glu Pro Arg Lys Asn Phe Val Lys Pro Asn Glu Thr Lys Thr Tyr Phe
            915                 920                 925

Trp Lys Val Gln His His Met Ala Pro Thr Lys Asp Glu Phe Asp Cys
            930                 935                 940

Lys Ala Trp Ala Tyr Phe Ser Asp Val Asp Leu Glu Lys Asp Val His
945                 950                 955                 960

Ser Gly Leu Ile Gly Pro Leu Leu Val Cys His Thr Asn Thr Leu Asn
                965                 970                 975

Pro Ala His Gly Arg Gln Val Thr Val Gln Glu Phe Ala Leu Phe Phe
                980                 985                 990

Thr Ile Phe Asp Glu Thr Lys Ser Trp Tyr Phe Thr Glu Asn Met Glu
        995                 1000                1005

Arg Asn Cys Arg Ala Pro Cys Asn Ile Gln Met Glu Asp Pro Thr
    1010                1015                1020

Phe Lys Glu Asn Tyr Arg Phe His Ala Ile Asn Gly Tyr Ile Met
    1025                1030                1035

Asp Thr Leu Pro Gly Leu Val Met Ala Gln Asp Gln Arg Ile Arg
    1040                1045                1050

Trp Tyr Leu Leu Ser Met Gly Ser Asn Glu Asn Ile His Ser Ile
    1055                1060                1065

His Phe Ser Gly His Val Phe Thr Val Arg Lys Lys Glu Glu Tyr
    1070                1075                1080

Lys Met Ala Leu Tyr Asn Leu Tyr Pro Gly Val Phe Glu Thr Val
    1085                1090                1095

Glu Met Leu Pro Ser Lys Ala Gly Ile Trp Arg Val Glu Cys Leu
    1100                1105                1110

Ile Gly Glu His Leu His Ala Gly Met Ser Thr Leu Phe Leu Val
    1115                1120                1125

Tyr Ser Asn Lys Cys Gln Thr Pro Leu Gly Met Ala Ser Gly His
    1130                1135                1140

Ile Arg Asp Phe Gln Ile Thr Ala Ser Gly Gln Tyr Gly Gln Trp
    1145                1150                1155

```
Ala Pro Lys Leu Ala Arg Leu His Tyr Ser Gly Ser Ile Asn Ala
    1160                1165                1170

Trp Ser Thr Lys Glu Pro Phe Ser Trp Ile Lys Val Asp Leu Leu
    1175                1180                1185

Ala Pro Met Ile Ile His Gly Ile Lys Thr Gln Gly Ala Arg Gln
    1190                1195                1200

Lys Phe Ser Ser Leu Tyr Ile Ser Gln Phe Ile Ile Met Tyr Ser
    1205                1210                1215

Leu Asp Gly Lys Lys Trp Gln Thr Tyr Arg Gly Asn Ser Thr Gly
    1220                1225                1230

Thr Leu Met Val Phe Phe Gly Asn Val Asp Ser Ser Gly Ile Lys
    1235                1240                1245

His Asn Ile Phe Asn Pro Pro Ile Ile Ala Arg Tyr Ile Arg Leu
    1250                1255                1260

His Pro Thr His Tyr Ser Ile Arg Ser Thr Leu Arg Met Glu Leu
    1265                1270                1275

Met Gly Cys Asp Leu Asn Ser Cys Ser Met Pro Leu Gly Met Glu
    1280                1285                1290

Ser Lys Ala Ile Ser Asp Ala Gln Ile Thr Ala Ser Ser Tyr Phe
    1295                1300                1305

Thr Asn Met Phe Ala Thr Trp Ser Pro Ser Lys Ala Arg Leu His
    1310                1315                1320

Leu Gln Gly Arg Ser Asn Ala Trp Arg Pro Gln Val Asn Asn Pro
    1325                1330                1335

Lys Glu Trp Leu Gln Val Asp Phe Gln Lys Thr Met Lys Val Thr
    1340                1345                1350

Gly Val Thr Thr Gln Gly Val Lys Ser Leu Leu Thr Ser Met Tyr
    1355                1360                1365

Val Lys Glu Phe Leu Ile Ser Ser Ser Gln Asp Gly His Gln Trp
    1370                1375                1380

Thr Leu Phe Phe Gln Asn Gly Lys Val Lys Val Phe Gln Gly Asn
    1385                1390                1395

Gln Asp Ser Phe Thr Pro Val Val Asn Ser Leu Asp Pro Pro Leu
    1400                1405                1410

Leu Thr Arg Tyr Leu Arg Ile His Pro Gln Ser Trp Val His Gln
    1415                1420                1425

Ile Ala Leu Arg Met Glu Val Leu Gly Cys Glu Ala Gln Asp Leu
    1430                1435                1440

Tyr

<210> SEQ ID NO 6
<211> LENGTH: 585
<212> TYPE: PRT
<213> ORGANISM: Homo sapiens

<400> SEQUENCE: 6

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
        50                  55                  60
```

```
Ser Leu His Thr Leu Phe Gly Asp Lys Leu Cys Thr Val Ala Thr Leu
 65                  70                  75                  80

Arg Glu Thr Tyr Gly Glu Met Ala Asp Cys Cys Ala Lys Gln Glu Pro
                 85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480
```

```
Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 7
<211> LENGTH: 519
<212> TYPE: PRT
<213> ORGANISM: Artificial Sequence
<220> FEATURE:
<223> OTHER INFORMATION: His-tagged D'D3
<220> FEATURE:
<221> NAME/KEY: MISC_FEATURE
<222> LOCATION: (1)..(479)
<223> OTHER INFORMATION: Amino acid sequence of D'D3 - His8
<220> FEATURE:
<221> NAME/KEY: MISC_FEATURE
<222> LOCATION: (1)..(479)
<223> OTHER INFORMATION: VWF D'D3 region (VWF amino acids 764 - 1242)
<220> FEATURE:
<221> NAME/KEY: MISC_FEATURE
<222> LOCATION: (480)..(511)
<223> OTHER INFORMATION: glycine / serine linker
<220> FEATURE:
<221> NAME/KEY: MISC_FEATURE
<222> LOCATION: (512)..(519)
<223> OTHER INFORMATION: polyhistidine tag

<400> SEQUENCE: 7

Ser Leu Ser Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
            20                  25                  30

Asp Leu Glu Cys Met Ser Met Gly Cys Val Ser Gly Cys Leu Cys Pro
        35                  40                  45

Pro Gly Met Val Arg His Glu Asn Arg Cys Val Ala Leu Glu Arg Cys
    50                  55                  60

Pro Cys Phe His Gln Gly Lys Glu Tyr Ala Pro Gly Glu Thr Val Lys
65                  70                  75                  80

Ile Gly Cys Asn Thr Cys Val Cys Arg Asp Arg Lys Trp Asn Cys Thr
                85                  90                  95

Asp His Val Cys Asp Ala Thr Cys Ser Thr Ile Gly Met Ala His Tyr
            100                 105                 110

Leu Thr Phe Asp Gly Leu Lys Tyr Leu Phe Pro Gly Glu Cys Gln Tyr
        115                 120                 125

Val Leu Val Gln Asp Tyr Cys Gly Ser Asn Pro Gly Thr Phe Arg Ile
    130                 135                 140

Leu Val Gly Asn Lys Gly Cys Ser His Pro Ser Val Lys Cys Lys Lys
145                 150                 155                 160

Arg Val Thr Ile Leu Val Glu Gly Gly Glu Ile Glu Leu Phe Asp Gly
                165                 170                 175
```

```
Glu Val Asn Val Lys Arg Pro Met Lys Asp Glu Thr His Phe Glu Val
                180                 185                 190

Val Glu Ser Gly Arg Tyr Ile Ile Leu Leu Gly Lys Ala Leu Ser
            195                 200                 205

Val Val Trp Asp Arg His Leu Ser Ile Ser Val Leu Lys Gln Thr
210                 215                 220

Tyr Gln Glu Lys Val Cys Gly Leu Cys Gly Asn Phe Asp Gly Ile Gln
225                 230                 235                 240

Asn Asn Asp Leu Thr Ser Ser Asn Leu Gln Val Glu Glu Asp Pro Val
                245                 250                 255

Asp Phe Gly Asn Ser Trp Lys Val Ser Ser Gln Cys Ala Asp Thr Arg
            260                 265                 270

Lys Val Pro Leu Asp Ser Ser Pro Ala Thr Cys His Asn Asn Ile Met
        275                 280                 285

Lys Gln Thr Met Val Asp Ser Ser Cys Arg Ile Leu Thr Ser Asp Val
    290                 295                 300

Phe Gln Asp Cys Asn Lys Leu Val Asp Pro Glu Pro Tyr Leu Asp Val
305                 310                 315                 320

Cys Ile Tyr Asp Thr Cys Ser Cys Glu Ser Ile Gly Asp Cys Ala Cys
                325                 330                 335

Phe Cys Asp Thr Ile Ala Ala Tyr Ala His Val Cys Ala Gln His Gly
            340                 345                 350

Lys Val Thr Trp Arg Thr Ala Thr Leu Cys Pro Gln Ser Cys Glu
        355                 360                 365

Glu Arg Asn Leu Arg Glu Asn Gly Tyr Glu Cys Glu Trp Arg Tyr Asn
    370                 375                 380

Ser Cys Ala Pro Ala Cys Gln Val Thr Cys Gln His Pro Glu Pro Leu
385                 390                 395                 400

Ala Cys Pro Val Gln Cys Val Glu Gly Cys His Ala His Cys Pro Pro
                405                 410                 415

Gly Lys Ile Leu Asp Glu Leu Leu Gln Thr Cys Val Asp Pro Glu Asp
            420                 425                 430

Cys Pro Val Cys Glu Val Ala Gly Arg Arg Phe Ala Ser Gly Lys Lys
        435                 440                 445

Val Thr Leu Asn Pro Ser Asp Pro Glu His Cys Gln Ile Cys His Cys
    450                 455                 460

Asp Val Val Asn Leu Thr Cys Glu Ala Cys Gln Glu Pro Gly Gly Ser
465                 470                 475                 480

Ser Gly Gly Ser Gly Gly Ser Gly Gly Ser Gly Gly Ser Gly Gly Ser
                485                 490                 495

Gly Gly Ser Gly Gly Ser Gly Gly Ser Gly Gly Ser Gly Gly Ser His
            500                 505                 510

His His His His His His
        515

<210> SEQ ID NO 8
<211> LENGTH: 584
<212> TYPE: PRT
<213> ORGANISM: Artificial sequence
<220> FEATURE:
<223> OTHER INFORMATION: His-tagged CTP fusion protein
<220> FEATURE:
<221> NAME/KEY: MISC_FEATURE
<222> LOCATION: (1)..(479)
<223> OTHER INFORMATION: VWF D'D3 region (VWF amino acids 764 - 1242)
```

```
<220> FEATURE:
<221> NAME/KEY: MISC_FEATURE
<222> LOCATION: (480)..(511)
<223> OTHER INFORMATION: glycine / serine linker
<220> FEATURE:
<221> NAME/KEY: MISC_FEATURE
<222> LOCATION: (512)..(576)
<223> OTHER INFORMATION: C-terminal peptide of human chorionic
      gonadotropin beta subunit
<220> FEATURE:
<221> NAME/KEY: MISC_FEATURE
<222> LOCATION: (577)..(584)
<223> OTHER INFORMATION: Polyhistidine tag

<400> SEQUENCE: 8
```

Ser Leu Ser Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
            20                  25                  30

Asp Leu Glu Cys Met Ser Met Gly Cys Val Ser Gly Cys Leu Cys Pro
        35                  40                  45

Pro Gly Met Val Arg His Glu Asn Arg Cys Val Ala Leu Glu Arg Cys
    50                  55                  60

Pro Cys Phe His Gln Gly Lys Glu Tyr Ala Pro Gly Glu Thr Val Lys
65                  70                  75                  80

Ile Gly Cys Asn Thr Cys Val Cys Arg Asp Arg Lys Trp Asn Cys Thr
                85                  90                  95

Asp His Val Cys Asp Ala Thr Cys Ser Thr Ile Gly Met Ala His Tyr
            100                 105                 110

Leu Thr Phe Asp Gly Leu Lys Tyr Leu Phe Pro Gly Glu Cys Gln Tyr
        115                 120                 125

Val Leu Val Gln Asp Tyr Cys Gly Ser Asn Pro Gly Thr Phe Arg Ile
    130                 135                 140

Leu Val Gly Asn Lys Gly Cys Ser His Pro Ser Val Lys Cys Lys Lys
145                 150                 155                 160

Arg Val Thr Ile Leu Val Glu Gly Gly Glu Ile Glu Leu Phe Asp Gly
                165                 170                 175

Glu Val Asn Val Lys Arg Pro Met Lys Asp Glu Thr His Phe Glu Val
            180                 185                 190

Val Glu Ser Gly Arg Tyr Ile Ile Leu Leu Leu Gly Lys Ala Leu Ser
        195                 200                 205

Val Val Trp Asp Arg His Leu Ser Ile Ser Val Val Leu Lys Gln Thr
    210                 215                 220

Tyr Gln Glu Lys Val Cys Gly Leu Cys Gly Asn Phe Asp Gly Ile Gln
225                 230                 235                 240

Asn Asn Asp Leu Thr Ser Ser Asn Leu Gln Val Glu Glu Asp Pro Val
                245                 250                 255

Asp Phe Gly Asn Ser Trp Lys Val Ser Ser Gln Cys Ala Asp Thr Arg
            260                 265                 270

Lys Val Pro Leu Asp Ser Ser Pro Ala Thr Cys His Asn Asn Ile Met
        275                 280                 285

Lys Gln Thr Met Val Asp Ser Ser Cys Arg Ile Leu Thr Ser Asp Val
    290                 295                 300

Phe Gln Asp Cys Asn Lys Leu Val Asp Pro Glu Pro Tyr Leu Asp Val
305                 310                 315                 320

Cys Ile Tyr Asp Thr Cys Ser Cys Glu Ser Ile Gly Asp Cys Ala Cys
                325                 330                 335

-continued

```
Phe Cys Asp Thr Ile Ala Ala Tyr Ala His Val Cys Ala Gln His Gly
            340                 345                 350

Lys Val Val Thr Trp Arg Thr Ala Thr Leu Cys Pro Gln Ser Cys Glu
        355                 360                 365

Glu Arg Asn Leu Arg Glu Asn Gly Tyr Glu Cys Glu Trp Arg Tyr Asn
    370                 375                 380

Ser Cys Ala Pro Ala Cys Gln Val Thr Cys Gln His Pro Glu Pro Leu
385                 390                 395                 400

Ala Cys Pro Val Gln Cys Val Glu Gly Cys His Ala His Cys Pro Pro
                405                 410                 415

Gly Lys Ile Leu Asp Glu Leu Leu Gln Thr Cys Val Asp Pro Glu Asp
            420                 425                 430

Cys Pro Val Cys Glu Val Ala Gly Arg Arg Phe Ala Ser Gly Lys Lys
        435                 440                 445

Val Thr Leu Asn Pro Ser Asp Pro Glu His Cys Gln Ile Cys His Cys
    450                 455                 460

Asp Val Val Asn Leu Thr Cys Glu Ala Cys Gln Glu Pro Gly Gly Ser
465                 470                 475                 480

Gly Gly Ser Gly Gly Ser Gly Gly Ser Gly Gly Ser Gly Gly Ser Gly
                485                 490                 495

Gly Ser Gly Gly Ser Gly Gly Gly Ser Gly Gly Ser Gly Ser Ser Ala
                500                 505                 510

Ser Ser Ser Ser Lys Ala Pro Pro Pro Ser Leu Pro Ser Pro Ser Arg
            515                 520                 525

Leu Pro Gly Pro Ser Asp Thr Pro Ile Leu Pro Gln Ala Ser Ser Ser
    530                 535                 540

Ser Lys Ala Pro Pro Pro Ser Leu Pro Ser Pro Ser Arg Leu Pro Gly
545                 550                 555                 560

Pro Ser Asp Thr Pro Ile Leu Pro Gln Ala Gly Gly Ser Gly Gly Ser
                565                 570                 575

His His His His His His His
            580
```